(12) United States Patent
Lee

(10) Patent No.: US 11,298,314 B2
(45) Date of Patent: Apr. 12, 2022

(54) INJECTABLE COMPOSITION FOR LOCALIZED FAT REDUCTION WITHOUT PAIN, EDEMA, AND SIDE EFFECTS, AND METHOD FOR PREPARING SAME

(71) Applicant: AMI PHARM CO., LTD., Gyeonggi-do (KR)

(72) Inventor: Ki Taek Lee, Seoul (KR)

(73) Assignee: AMI PHARM CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/311,960

(22) PCT Filed: Apr. 20, 2018

(86) PCT No.: PCT/KR2018/004642
§ 371 (c)(1),
(2) Date: Dec. 20, 2018

(87) PCT Pub. No.: WO2018/194427
PCT Pub. Date: Oct. 25, 2018

(65) Prior Publication Data
US 2019/0201328 A1    Jul. 4, 2019

(30) Foreign Application Priority Data

Apr. 21, 2017  (KR) .................. 10-2017-0051868
Nov. 3, 2017  (KR) .................. 10-2017-0146264

(51) Int. Cl.
| | |
|---|---|
| *A61K 9/00* | (2006.01) |
| *A61K 47/28* | (2006.01) |
| *A61K 47/10* | (2017.01) |
| *A61K 31/685* | (2006.01) |
| *A61P 3/04* | (2006.01) |
| *A61K 31/575* | (2006.01) |

(52) U.S. Cl.
CPC .......... *A61K 9/0019* (2013.01); *A61K 31/575* (2013.01); *A61K 31/685* (2013.01); *A61K 47/10* (2013.01); *A61K 47/28* (2013.01); *A61P 3/04* (2018.01)

(58) Field of Classification Search
CPC .... A61K 9/0019; A61K 31/575; A61K 47/28; A61K 47/10; A61K 31/685; A61P 3/04
See application file for complete search history.

(56) References Cited

U.S. PATENT DOCUMENTS

| | | | | |
|---|---|---|---|---|
| 6,663,885 | B1 * | 12/2003 | Hager | ............ A61K 8/14 424/450 |
| 7,622,130 | B2 | 11/2009 | Kolodney et al. | |
| 2005/0089555 | A1 | 4/2005 | Boderke et al. | |
| 2005/0143347 | A1 | 6/2005 | Boderke et al. | |
| 2009/0221528 | A1 * | 9/2009 | Denney | ............ A61K 9/0019 514/75 |
| 2014/0113883 | A1 | 4/2014 | DeLuze | |
| 2016/0058780 | A1 | 3/2016 | Lee | |

FOREIGN PATENT DOCUMENTS

| | | |
|---|---|---|
| AU | 2004308072 A1 | 6/2006 |
| CA | 2543187 A1 | 5/2005 |
| CA | 2551 474 A1 | 7/2005 |
| CA | 2551474 A1 | 7/2005 |
| CN | 101152189 A | 4/2008 |
| DE | 103 61 067 A1 | 7/2005 |
| DE | 10361067 | 7/2005 |
| DE | 10361067 A1 | 7/2005 |
| JP | 2007-509085 A | 4/2007 |
| JP | 2007-515439 A | 6/2007 |
| JP | 2007-538104 A | 12/2007 |
| JP | 2007-509085 A | 4/2008 |
| KR | 10-2006-0117914 A | 11/2006 |
| KR | 10-2011-0127425 A | 11/2011 |
| RU | 2500686 C2 | 12/2013 |
| WO | WO 2005/041919 A2 | 5/2005 |

(Continued)

OTHER PUBLICATIONS

Communication pursuant to Rule 114(2) EPC in the corresponding European Patent Application No. 18787918.4, dated Oct. 28, 2019.
M. C. Carey, et al., "Micelle Formation by Bile Salts. Physical-Chemical and Thermodynamic Considerations," Arch Intern Med., Oct. 1972, vol. 130, pp. 506-527.
International Search Report in corresponding PCT Application No. PCT/KR2018/004642, dated Aug. 7, 2018.
Extended European Search Report in corresponding European Application No. EP 18 78 7918, dated Jul. 26, 2019.
Russian Office Action in corresponding Russian Application No. 2019112583/04(024387), dated May 20, 2020.
Australian Examination Report in corresponding Australian Application No. 2018256263, dated Sep. 4, 2020.

(Continued)

*Primary Examiner* — Sahar Javanmard
(74) *Attorney, Agent, or Firm* — Leason Ellis LLP

(57) ABSTRACT

The present invention relates to a composition comprising glycocholic acid or taurocholic acid and phosphatidylcholine at a particular mixing ratio for reducing localized fat without side effects such as a pain, edema, necrosis of muscle cells, fibroblasts and vascular endothelial cells other than adipocytes, anesthesia of administration sites, extensive swelling, erythema, induration, paresthesia, nodule, pruritus, burning sensation, nerve injury, and dysphagia, and a method for preparing the same.

The inventor has found that the effect of PPC injectable composition on fat reduction may be reduced or enhanced during its subcutaneous administration, depending on the types of solubilizing agents, especially the types of bile acids, which are combined so as to prepare a safe and stable PPC injection using insoluble PPC.

The PPC injectable composition solubilized with GCA or TCA selectively reduces adipocytes without inducing necrosis of fibroblasts, muscle cells and vascular endothelial cells, thereby alleviating the known clinical side effects.

8 Claims, 41 Drawing Sheets
(32 of 41 Drawing Sheet(s) Filed in Color)

(56) References Cited

FOREIGN PATENT DOCUMENTS

| WO | WO 2005/063169 A2 | 7/2005 |
|---|---|---|
| WO | WO 2005/112942 A1 | 12/2005 |
| WO | WO 2018/194427 A1 | 10/2018 |

OTHER PUBLICATIONS

Hexsel, D, "Phosphatidylcholine in the Treatment of Localized Fat" J. Drugs in Dermatology 2003, vol. 2 No 5, p. 511-518.
Young V "Lipostabil: Effect of Phosphatidylcholine on Subcutaneous Fat" Aesthetic Surgery Journal, 2003, vol. 23, p. 413-417.
Rittes P G: "The Use of Phosphatidylcholine for the Correction of Localized Fat Deposits" Aesthetic Plastic Surgery 2003 vol. 27 No. 4 p. 315-318.
Canadian Examiner's Report in corresponding Canadian Application No. 3,031,678, dated Sep. 1, 2020.
Taiwan Examination Report in corresponding Taiwan Application No. 107138940 dated Sep. 14, 2020.
Office Action in corresponding Japanese Application No. 2019-547440 dated Oct. 6, 2020 (English translation attached hereto).

\* cited by examiner

PPC 5.0% injectable compositions solubilized with DCA of various concentrations immediately after preparation | 30 days after preparation PPC 5.0% injectable compositions solubilized with GCA of various concentrations immediately after preparation | 30 days after preparation and 0.2 μm filtration PPC 5.0% injectable compositions solubilized with TCA of various concentrations PPC 5.0% injectable compositions solubilized with CA of various concentrations PPC 5.0% injectable compositions solubilized with CDCA of various concentrations PPC 5.0% injectable compositions solubilized with UDCA of various concentrations PPC 5.0% injectable compositions solubilized with GDCA of various concentrations immediately after preparation 30 days after preparation PPC 5.0% injectable compositions solubilized with TDCA of various concentrations immediately after preparation 30 days after preparation PPC 5.0% injectable compositions solubilized with HDCA of various concentrations immediately after preparation 30 days after preparation PPC 5.0% injectable compositions solubilized with TUDCA of various concentrations immediately after preparation 30 days after preparation PPC 5.0% injectable compositions solubilized with LCA PPC 5.0% injectable compositions solubilized with DHCA of various concentrations immediately after preparation 30 days after preparation

| PPC 5.0%+DCA 2.2% | PPC 5.0%+HDCA 2.5% | PPC 5.0%+UDCA 3.0% |
|---|---|---|
| PPC 5.0%+TDCA 2.5% | PPC 5.0%+GDCA 2.5% | PPC 5.0%+CDCA 2.5% |
| PPC 5.0%+CA 2.5% | PPC 5.0%+GCA 2.5% | PPC 5.0%+TCA 2.5% |
| PPC 5.0%+TUDCA 4.0% | | |

After 24 hours

After 48 hours

After 72 hours

After 96 hours

After 48 hours

After 24 hours

FIG. 11B

| | 200x | 400x |
|---|---|---|
| PBS | | |
| Isuprel | | |
| DCA 1.0% | | |
| PPC 5.0% + DCA 2.2% | | |
| PPC 5.0% + CDCA 2.5% | | |
| PPC 5.0% + HDCA 2.5% | | |
| PPC 5.0% + UDCA 3.0% | | |

| | 200x | 400x |
|---|---|---|
| PPC 5.0% + GDCA 2.5% |  |  |
| PPC 5.0% + TDCA 2.5% |  |  |
| PPC 5.0% + CA 2.5% |  |  |
| PPC 5.0% + GCA 2.5% |  |  |
| PPC 5.0% + TCA 2.5% |  |  |
| PPC 5.0% + TUDCA 4.0% |  |  |

FIG. 11D

| | dermis | adipocytes |
|---|---|---|
| PBS (negative control) | | |
| PPC 5.0% | | |
| PPC 2.5% + GCA 1.25% | | |
| PPC 5.0% + GCA 2.5% | | |
| PPC 10.0% + GCA 5.0% | | |
| GCA 2.5% | | |

| GROUP | Low dose (female beagle) (PPC 90mg/kg+GCA 50.4mg/kg) | GROUP | Low dose (male beagle) (PPC 90mg/kg+GCA 50.4mg/kg) |
|---|---|---|---|
| 01 |  | 01 |  |
| 02 |  | 02 |  |

| GROUP | Medium dose (female beagle) (PPC 180mg/kg+GCA 100.8mg/kg) | GROUP | Medium dose (male beagle) (PPC 180mg/kg+GCA 100.8mg/kg) |
|---|---|---|---|
| 01 |  | 01 |  |
| 02 |  | 02 |  |

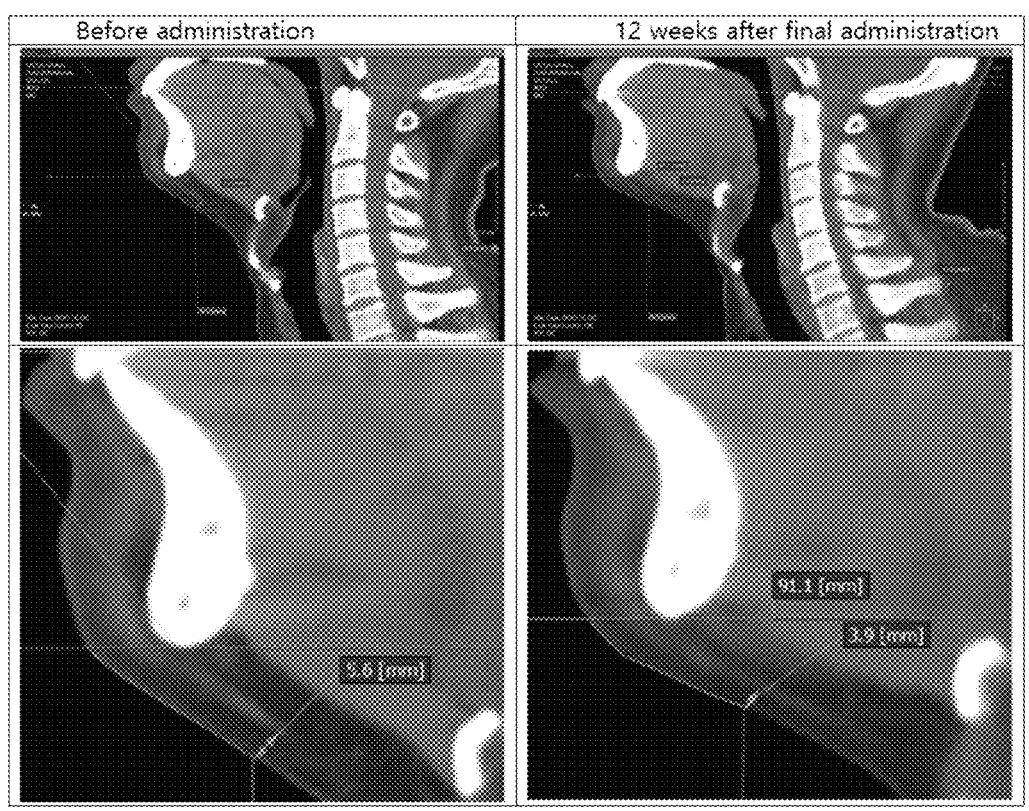
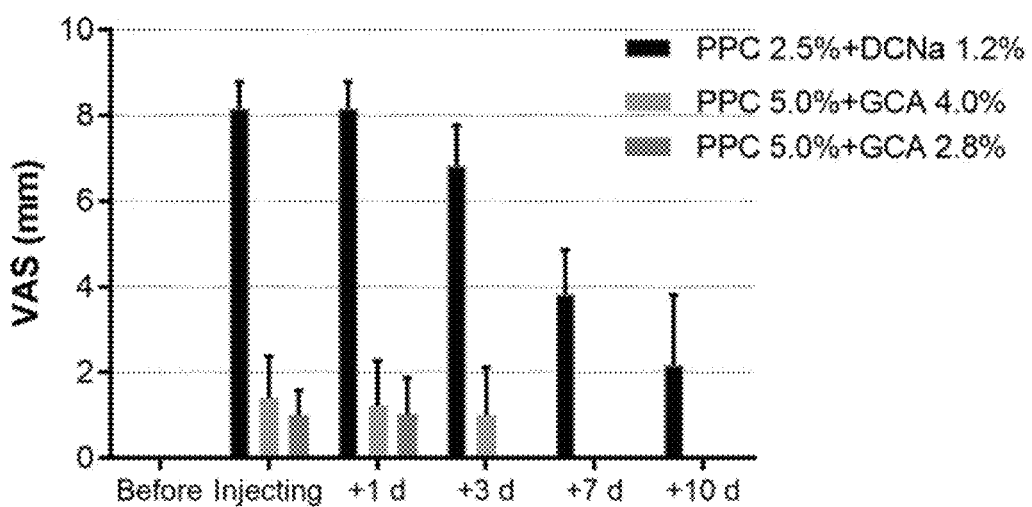

0: Absent, 1: Mild, 2: Moderate, 3: Serve, 4: Extreme

0: Absent, 1: Mild, 2: Moderate, 3: Serve, 4: Extreme

| | Before administration | 2 days after administration |
|---|---|---|
| PPC 2.5% solubilized with DCNa |  |  |
| PPC 5% solubilized with GCA |  |  |

INJECTABLE COMPOSITION FOR LOCALIZED FAT REDUCTION WITHOUT PAIN, EDEMA, AND SIDE EFFECTS, AND METHOD FOR PREPARING SAME

CROSS-REFERENCE TO RELATED PATENT APPLICATIONS

This application is a U.S. National Phase Application under 35 U.S.C. § 371 of International Patent Application No. PCT/KR2018/004642, filed Apr. 20, 2018 that claims priority to KR 10-2017-0146264, filed Nov. 3, 2017 and KR 10-2017-0051868, filed Apr. 20, 2017, all of which are incorporated by reference in their entireties. The International Application was published on Oct. 25, 2018 as International Publication No. WO 2018/194427 A1.

TECHNICAL FIELD

The present invention relates to a composition useful to reduce fat non-surgically without a pain, edema, and side effect in a subject having localized fat deposition using pharmaceutically active phosphatidylcholine and a method for preparing the same. More specifically, the present invention relates to a composition and preparation for reducing localized fat with a reduced pain and side effect (especially, necrosis of muscle cells, fibroblasts and vascular endothelial cells other than adipocytes; edema; anesthesia of administration sites; extensive swelling; erythema; induration; paresthesia; nodule; pruritus; burning sensation; nerve injury; or dysphagia), the composition comprising: (i) phosphatidylcholine; and (ii) at least one selected from the group consisting of glycocholic acid (GCA), taurocholic acid (TCA) and salt thereof, wherein a molar ratio of (ii) to (i) in the composition is in a range of 0.7 to 3.0, a kit comprising the same, a method for preparing the same, and a method for non-surgically removing localized fat deposition with a reduced pain and side effect using the composition or preparation.

BACKGROUND ART

The present application claims priorities from Korean Patent Application No. 10-2017-0051868 filed on Apr. 21, 2017, and Korean Patent Application No. 10-2017-0146264 file on Nov. 3, 2017, the entirety of them is incorporated herein by reference.

Locally deposited fat is a special concern for many people. People who have unwanted convex or plump fat deposition in their face or part of their body may look less appealing and look older. These can be caused by aging, lifestyle, or genetic predisposition. To overcome this, we try to improve through exercise and diet, but the fat reduction effect is limited.

Typical surgical cosmetic plastic surgery procedures for reducing localized fat deposition include liposuction, lipoplasty and liposculpture suction, these are cosmetic plastic surgeries removing large amount of fat. Cosmetic minimally-invasive (non-surgical) procedures are procedures using medical devices, mesotheraphy or off-label injections. However, the surgical procedure takes several weeks or months to heal, and certain individuals, such as smokers and diabetics, may experience considerable delay in healing, and includes potential complications and risks such as fatal side effects causing 20 deaths per 100,000 people, the risk of general anesthesia, excessive bleeding, internal organ damage, bacterial infections, scarring, bruising, swelling, and pain. In the case of non-surgical methods that is an alternative thereof, there is a potential risk because the safety and efficacy are not ensured due to the absence of large-scale clinical trials that is conducted with approval under the supervision of the health authorities. There is need for development of clinically useful new drugs that doesn't have the risk of surgical and non-surgical procedure.

Injectable drugs for localized fat reduction are injections of the drug into the subcutaneous fat layer to induce fat cell loss. A typical example is PPC injection. PPC injection is an abbreviation of Polyene Phosphatidylcholine, and there is Essentiale® N i.v. developed by A. Nattermann GmbH of Germany in the 1950s for the treatment of liver disease and Lipostabil® N i.v. developed for the prevention and treatment of fat embolism and Lipobean® which has been approved as an adjuvant medicine for hepatic coma due to cirrhosis in the Republic of Korea.

During PPC injections were prescribed for the prevention and treatment of liver disease or fat embolism, in 1988, Dr. Sergio Maggiori, an Italian doctor at the MesoTherapy Society in Paris, France, reported the test result for the first time that Xantelasma, a disease in which yellow fat deposits in the eyelids, was treated by PPC injection, in 1999, Dr, Patricia G. Rittes, a Brazilian dermatologist at the Brazil Dermatology Society announced the test result of lower eyelid fat pads reduction with PPC injection, confirming the possibility of fat loss with the PPC injection. Since then, test results have been published regarding the small-scale safety and safety of PPC injection into fat-deposited abdomen, flank, thigh, submental, back, arm, leg and lipoma.

The PPC injection is a composition in which a main component polyene phosphatidylcholine and a solubilizing agent deoxycholic acid are mixed. PPC is an essential phospholipid and a main component of biological membrane, and is composed of a hydrophobic tail structure in which five fatty acids are bonded to the hydrophilic head of phosphorus and choline in the glycerol carbon backbone. It constitutes 55% of the cell membrane and mitochondrial network of the human body. Since it is hardly synthesized in the human body, it is an essential ingredient to be supplied from the outside of the body. It is highly contained in soybean, egg and the like. And it can be extracted by physical or chemical method using nucleic acid and purified in high purity.

Deoxycholic acid (DCA) is one of the secondary bile salts, a metabolic byproduct of enterobacteria and is mixed as a solubilizing agent to make a poorly soluble PPC into a stably injectable composition. The PPC solubilized with the DCA is stably dispersed as a mixed micelles system of less than 10 nm. If injected without PPC solubilization, it will not be dissolved in a single molecule and the desired blood concentration will not be obtained. In addition, blood vessels may become clogged and thrombosis may occur, so non-solubilized PPC is not used as injections. If the drug is not solubilized during intravenous injection and forms a suspended precipitate, large particles will block the blood vessels, affect the blood flow of surrounding tissues near the blocked blood vessels, or damage or stimulate the tissue, resulting in pruritus, pain, seizure, and the like. In severe cases, an embolization may occur.

The PPC had been regarded as an active ingredient of fat reduction based on the fact that Lipostabil® N iv, a composition comprising PPC as a main component and DCA as a solubilizing agent, is prescribed for the treatment of fat embolism, in which fatty tissue flows into the vein causing embolism. But, it was confirmed that DCA mixed as a solubilizing agent in the PPC injections causes necrosis due to the detergent effect, resulting in a decrease in adipocytes. Thus, it has been found that the lipid-lowering active ingredient of the PPC injections is DCA (Non-Patent Document 1). Based on this, in 2015, the FDA approved a DCA single injection, which does not contain PPC, developed by Kythera biopharmaceuticals INC, a privately held company located in the US, as a cytolytic agent for improving the appearance through submental fat reduction.

However, since DCA single injections or PPC injections solubilized with DCA lyse not only adipocytes (3T3L1 adipocytes) but also normal fibroblasts, endothelial cells, and skeletal muscle cells non-selectively, it is cell lysis injections rather than fat degradation injections (Non-Patent Document 2).

Clinically, the composition, in which PPC and DCA are mixed, is reported to cause pain (78.4%), hematoma (83.8%), erythema (100%), burning sensation (100%), edema (100%) and induration (66.7%), and DCA single composition is reported to cause pain (100%), bruise (91.9%), erythema (100%), burning sensation (100%), swelling (100%) and induration (89.2%)(Non-patent document 3). In addition, the result of a large-scale clinical trial of DCA single composition showed that the pain (73.6%), hematoma (72.9%), edema (67.8%), anesthesia (65.5%), erythema (35.3%), swelling (29.1%), induration (28.3%), pruritus (16.3%) and nodule (14.3%) were caused (Non-Patent Document 4). These harmful cases are caused by the mechanism of action that subcutaneously injected DCA blocks the oxygen supply to cells, causing immediate cell expansion and blister and damage to the cell membrane, resulting in necrosis of the cells due to a rapid inflammatory reaction (Non-Patent Document 5).

When cells die in vivo, there is marked differences in being necrosis and apoptosis. Apoptosis refers to active death in which the expression and activity of various genes and proteins are regulated by a signal programmed inside the cells, and apoptosomes generated through the process are removed by phagocytosis of surrounding cells or macrophages, and the like, so that it does not cause inflammation. On the other hand, necrosis is a passive death that occurs suddenly due to changes in the external environment, which leads to irregular clumping of the chromosome and swelling of cytoplasm. Finally, cell debris are formed through degradation of the cells and they are known to cause inflammation (Earnshaw, W C, Curr. Opin. Cell Biol., 7, pp 337-343, 1995).

Therefore, when the injection of localized fat reduction acts as a cell necrosis factor, the inflammatory action affects the surrounding area other than the target site to which the drug is administered, so that it also affects the cells to be normally functioning and thus it is killed. To sum up these facts, it is important to selectively and high efficiently induce lipolysis and apoptosis of adipocytes without the side effects of already approved appearance remediation injections such as pain, swelling, anesthesia, extensive swelling, erythema, induration, paresthesia, nodule, pruritus, burning sensation and necrosis of muscle cells, fibroblasts and vascular endothelial cells other than adipocytes. However, there have been no studies and formulations developed from this point of view to date (Non-Patent Document 6).

Up to date, there has been an off-label treatment with Lipostabil® N i.v., Essentiale® N i.v., an injectable formulation of the composition in which PPC and DCA are mixed, for localized fat reduction, and Kybella (DCA single composition) has been not only done much research on fat reduction, but Kybella is also the first in the world to receive FDA approval as a cytolytic drug for appearance improvement. But the prior art and compositions have certain limitations. Those who want to lose fat with a non-surgical treatment are complaining of discomfort and anxiety, because of the side effects caused by PPC+DCA composition or the DCA single composition such as pain, swelling, anesthesia, extensive swelling, erythema, induration, paresthesia, nodule, pruritus, burning sensation and necrosis of muscle cells, fibroblasts and vascular endothelial cells other than adipocytes. For these reasons, although the clinical efficacy has been verified at present, the compliance with medication is low. Therefore, as compared with currently available cytolytic injections, it is required to develop injections that do not cause pain and swelling due to inflammation and that decrease the fat without side effects by selectively inducing apoptosis and degradation of adipocytes. The present invention satisfies these requirements.

Based on the above facts, the inventors of the present invention investigated the fat reduction effect of PPC, and reported the test results that the PPC alone composition without DCA reduced only adipocytes by apoptosis, not by necrosis, without affecting the fibroblast (Non-Patent Document 7). Since then, the present inventors have completed the present invention while studying a composition for selective fat cell reduction based on PPC as an active ingredient without pain, edema and side effects.

(Non-Patent Document 1) Rotunda A M, Suzuki H, Moy R L, Kolodney M., Detergent effects of sodium deoxycholate are a major feature of an injectable phosphatidylcholine formulation used for localized fat dissolution. Dermatol Surg 30(7):1001-8(2004)

(Non-Patent Document 2) A. Gupta, Action and comparative efficacy of phosphatidylcholine formulation and isolated sodium deoxycholate for different cell type, Aest Plast Sur, 33:346-352, 2009

(Non-Patent Document 3) Giovanni Salti, Phosphatidylcholine and sodium deoxycholate in the treatment of localized fat: A double-blind, randomized study, Dermatol Surg 34:60-66, 2007

(Non-Patent Document 4) Humphrey et al, ATX-101 for reduction of submental fat: A Phase III randomized controlled trial, J AM ACAD DERMATOL Vol 75, No. 4, 788-797, 2016

(Non-Patent Document 5) Duncan, Injectable therapies for localized fat loss: state of the art, Clin Plastic Surg, 1-13, 2011

(Non-Patent Document 6) Duncan, Refinement of Technique in injection lipolysis based on scientific studies and clinical evaluation, Clin Plastic Surg 36 195-209 (2009)

(Non-Patent Document 7) Dong-Seok Kim, Phosphatidylcholine induces apoptosis of 3T3-L1 adipocytes, Journal of biomedical science, 18:91, 1-7, 2011

DETAILED DESCRIPTION OF THE INVENTION

Technical Problem

In order to solve the side effect problems of conventional DCA single injection or PPC injection solubilized with DCA, such as pain, edema and various side effects caused by non-selective cell lysis, especially, serious clinical side effects caused by the necrosis of muscle cells, fibroblasts and vascular endothelial cells other than adipocytes, the inventors of the present invention conducted an test to prepare a safe and stable injectable composition for localized fat reduction which reduces fat without pain and edema by the mechanism of inducing apoptosis and lipolysis in adipocytes, and selectively reduces adipocyte without damaging fibroblasts, vascular endothelial cells and skeletal muscle cells. As a result, the inventor has completed the present invention after confirming the facts that composition of the present invention prepared by adding taurocholic acid (TCA), particularly glycocholic acid (GCA) to phosphatidylcholine (PPC) at a specific ratio, is safe and has excellent formulation stability, and do not induce cell necrosis, but induces apoptosis and degradation of only adipocytes selectively.

Therefore, an aspect of the present invention is to provide a composition for reducing localized fat with a reduced pain and side effect (edema; anesthesia of the site of administration; extensive swelling; erythema; induration; paresthesia; nodule; pruritus; burning sensation; nerve injury; dysphagia; and necrosis of muscle cells, fibroblasts and vascular endothelial cells other than adipocytes), the composition comprising: (i) phosphatidylcholine; and (ii) at least one selected from the group consisting of glycocholic acid (GCA), taurocholic acid (TCA) and salt thereof, wherein a molar ratio of (ii) to (i) in the composition is in a range of 0.7 to 3.0.

Another aspect of the present invention is to provide a preparation for removing localized fat deposition with a reduced pain and side effect in a subject, the preparation comprising: (i) phosphatidylcholine; and (ii) at least one selected from the group consisting of glycocholic acid (GCA), taurocholic acid (TCA) and salt thereof, wherein a molar ratio of (ii) to (i) in the preparation is in a range of 0.7 to 3.0.

Another aspect of the present invention is to provide a kit comprising: (I) a first container comprising a composition or preparation for removing localized fat deposition with a reduced pain and side effect, the composition or preparation comprising: (i) phosphatidylcholine; and (ii) at least one selected from the group consisting of glycocholic acid (GCA), taurocholic acid (TCA) and salt thereof, wherein a molar ratio of (ii) to (i) in the composition or preparation is in a range of 0.7 to 3.0; and (II) a delivery device capable of delivering the composition or preparation to a site of fat deposition.

Another aspect of the present invention is to provide a kit comprising: (I) a first container comprising a composition or preparation for removing localized fat deposition with a reduced pain and side effect, the composition or preparation comprising: (i) phosphatidylcholine; and (ii) at least one selected from the group consisting of glycocholic acid (GCA), taurocholic acid (TCA) and salt thereof, wherein at least one selected from the group consisting of glycocholic acid (GCA), taurocholic acid (TCA) and salt thereof is contained at the same weight as the phosphatidylcholine or less; and (II) a delivery device capable of delivering the composition or preparation to a site of fat deposition.

Another aspect of the present invention is to provide a method for preparing an injectable composition for reducing localized fat with a reduced pain and side effect (edema; anesthesia of the site of administration; extensive swelling; erythema; induration; paresthesia; nodule; pruritus; burning sensation; nerve injury; dysphagia; and necrosis of muscle cells, fibroblasts and vascular endothelial cells other than adipocytes), the method comprising the steps of: (a) adding at least one selected from the group consisting of glycocholic acid (GCA), taurocholic acid (TCA) and salt thereof to water for injection, followed by dissolving while stirring to obtain a clear mixture; (b) adding a preservative, followed by stirring; (c) adding phosphatidylcholine, followed by stirring at room temperature; and (d) adjusting a total volume of the composition with water, followed by stirring, wherein a molar ratio of the at least one selected from the group consisting of glycocholic acid (GCA), taurocholic acid (TCA) and salt thereof to the phosphatidylcholine is in a range of 0.7 to 3.0.

Another aspect of the present invention is to provide a method for preparing a pharmaceutical composition for non-surgically removing localized fat deposition with a reduced pain and side effect, the method comprising adding phosphatidylcholine, and at least one selected from the group consisting of glycocholic acid, taurocholic acid and salt thereof,
wherein the at least one selected from the group consisting of glycocholic acid, taurocholic acid and salt thereof is added at the same weight as the phosphatidylcholine or less.

Another aspect of the present invention is to provide a method for removing localized fat deposition with a reduced pain and side effect, the method comprising administering an effective amount of phosphatidylcholine; and at least one solubilizing agent of phosphatidylcholine selected from the group consisting of glycocholic acid, taurocholic acid and salt thereof to a subject having localized fat deposition.

Another aspect of the present invention is to provide a method for non-surgically removing localized fat deposition with a reduced pain and side effect in a subject having localized fat deposition, the method comprising administering a preparation comprising (i) phosphatidylcholine; and (ii) at least one selected from the group consisting of glycocholic acid, taurocholic acid and salt thereof.

Another aspect of the present invention is to provide a method for non-surgically removing localized fat deposition with a reduced pain and side effect in a subject, the method comprising administering a preparation comprising (i) phosphatidylcholine; and (ii) at least one selected from the group consisting of glycocholic acid, taurocholic acid and salt thereof to the subject having localized fat deposition, wherein a molar ratio of (ii) to (i) in the preparation is in a range of 0.7 to 3.0.

In one embodiment, the preparation comprises phosphatidylcholine at a concentration of 1.0% to about 15.0% as a fat-lysing concentration.

In one embodiment, the preparation is an injectable preparation. In another embodiment, the preparation is injectable preparation for reducing adipocyte.

The present invention also provides a method for non-surgical reduction in a subject having localized fat deposition.

In one embodiment, the method comprises administering a preparation comprising at least one of phosphatidylcholine composition that is solubilized with glycocholic acid or aurocholic acid in a pharmaceutically acceptable preparation having a pH of from pH 6.0 to pH 9.0.

In one embodiment, the administering process comprises a subcutaneous injection.

In one embodiment, the localized fat deposition is selected from the group consisting of lower eyelid fat herniation, lipomas, lipodystrophy and fat deposits associated with cellulite.

In one embodiment, the fat deposition is localized under the eyes, submental (under the chin), under the arms, in the buttocks, calves, back, thighs, ankles or stomach in the subject.

The present invention also provides a kit comprising a written instruction for using preparation comprising at least one of phosphatidylcholine composition solubilized with glycocholic acid or taurocholic acid, for non-surgically removing the localized fat deposition in the subject.

Technical Solution

In accordance with an aspect of the present invention, there is provided a composition for reducing localized fat with a reduced pain and side effect (edema; anesthesia of the site of administration; extensive swelling; erythema; induration; paresthesia; nodule; pruritus; burning sensation; nerve injury; dysphagia; and necrosis of muscle cells, fibroblasts and vascular endothelial cells other than adipocytes), the composition comprising: (i) phosphatidylcholine; and (ii) at least one selected from the group consisting of glycocholic acid (GCA), taurocholic acid (TCA) and salt thereof, wherein a molar ratio of (ii) to (i) in the composition is in a range of 0.7 to 3.0.

In accordance with another aspect of the present invention, there is provided a preparation for removing localized fat deposit with a reduced pain and side effect in a subject, the preparation comprising: (i) phosphatidylcholine; and (ii) at least one selected from the group consisting of glycocholic acid (GCA), taurocholic acid (TCA) and salt thereof, wherein a molar ratio of (ii) to (i) in the preparation is in a range of 0.7 to 3.0.

In accordance with another aspect of the present invention, there is provided a kit comprising: (I) a first container comprising a composition or preparation for removing localized fat deposition with a reduced pain and side effect, the composition or preparation comprising: (i) phosphatidylcholine; and (ii) at least one selected from the group consisting of glycocholic acid (GCA), taurocholic acid (TCA) and salt thereof, wherein a molar ratio of (ii) to (i) in the composition or preparation is in a range of 0.7 to 3.0; and (II) a delivery device capable of delivering the composition or preparation to a site of fat deposition.

In accordance with another aspect of the present invention, there is provided a kit comprising: (I) a first container comprising a composition or preparation for removing localized fat deposition with a reduced pain and side effect, the composition or preparation comprising: (i) phosphatidylcholine; and (ii) at least one selected from the group consisting of glycocholic acid (GCA), taurocholic acid (TCA) and salt thereof, wherein at least one selected from the group consisting of glycocholic acid (GCA), taurocholic acid (TCA) and salt thereof is contained at the same weight as the phosphatidylcholine or less; and (II) a delivery device capable of delivering the composition or preparation to a site of fat deposition.

In accordance with another aspect of the present invention, there is provided a method for preparing an injectable composition for reducing localized fat with a reduced pain and side effect (edema; anesthesia of the site of administration; extensive swelling; erythema; induration; paresthesia; nodule; pruritus; burning sensation; nerve injury; dysphagia; and necrosis of muscle cells, fibroblasts and vascular endothelial cells other than adipocytes), the method comprising the steps of: (a) adding at least one selected from the group consisting of glycocholic acid (GCA), taurocholic acid (TCA) and salt thereof to water for injection, followed by dissolving while stirring to obtain a clear mixture; (b) adding a preservative, followed by stirring; (c) adding phosphatidylcholine, followed by stirring at room temperature; and (d) adjusting a total volume of the composition with water, followed by stirring, wherein a molar ratio of the at least one selected from the group consisting of glycocholic acid (GCA), taurocholic acid (TCA) and salt thereof to the phosphatidylcholine is in a range of 0.7 to 3.0.

In accordance with another aspect of the present invention, there is provided a method for preparing a pharmaceutical composition for non-surgically removing localized fat deposition with a reduced pain and side effect, the method comprising adding phosphatidylcholine, and at least one selected from the group consisting of glycocholic acid, taurocholic acid and salt thereof, wherein the at least one selected from the group consisting of glycocholic acid, taurocholic acid and salt thereof is added at the same weight as the phosphatidylcholine or less.

In accordance with another aspect of the present invention, there is provided a method for removing localized fat deposition with a reduced pain and side effect in a subject, the method comprising administering an effective amount of phosphatidylcholine; and at least one solubilizing agent of phosphatidylcholine selected from the group consisting of glycocholic acid, taurocholic acid and salt thereof to the subject having localized fat deposition.

In accordance with another aspect of the present invention, there is provided a method for non-surgically removing localized fat deposition with a reduced pain and side effect in a subject having localized fat deposition, the method comprising administering a preparation comprising (i) phosphatidylcholine; and (ii) at least one selected from the group consisting of glycocholic acid, taurocholic acid and salt thereof.

In accordance with another aspect of the present invention, there is provided a method for non-surgically removing localized fat deposition with a reduced pain and side effect in a subject, the method comprising administering a preparation comprising (i) phosphatidylcholine; and (ii) at least one selected from the group consisting of glycocholic acid, taurocholic acid and salt thereof to the subject having localized fat deposition, wherein a molar ratio of (ii) to (i) in the preparation is in a range of 0.7 to 3.0.

Terms

The term 'phosphatidylcholine' in the present invention refers to a compound of IUPAC Name 1,2-diacyl-sn-glycero-3-phosphocholine as a phospholipid and is described in this specification as PPC.

Unless defined otherwise, all technical and scientific terms used herein have the same meaning as commonly understood by one of ordinary skill in the art to which the present invention belongs. Although any methods and materials similar or equivalent to those described herein can be used in the practice or test of the present invention, the preferred methods and materials are described.

As used herein, each of the following terms has the meaning associated with it in this section.

The articles "a" and "an" are used herein to denote one or more (i.e., at least one) of the grammatical objects of the article. For example, "an element" refers to one element or more.

When referring to measurable values such as quantity, time length, etc, the term "about" refers to comprising a variation of ±20%, ±10%, ±5%, ±1%, or ±0.1% from the specified value, because such variation is proper to perform the specified method.

The disease or disorder is "alleviated" if the severity of the symptoms of the disease or disorder, the frequency of such symptoms experienced by the patient, or both is reduced.

As used herein, the term "bile acid" includes steroidic acids (and/or their carboxylic acid anions), and salts thereof, and is found in the bile of an animal (for example, human). "Deoxycholic acid" is a kind of bile salt, and refers to a compound IUPAC name (4R)-4-[(3R,5R,8R,9S,10S,12S, 13R,14S,17R)-3,12-dihydroxy-10,13-dimethyl-2,3,4,5,6,7,8,9,11,12,14,15,16,17-tetradecahydro-1H-cyclopenta[a]phenanthren-17-yl]pentanoic acid and is described in this specification as DCA.

The "Glycocholic acid" is a kind of bile salt, and refers to a compound IUPAC name 2-[[(4R)-4-[(3R,5S,7R,8R,9S,10S,12S,13R,14S,17R)-3,7,12-trihydroxy-10,13-dimethyl-2,3,4,5,6,7,8,9,11,12,14,15,16,17-tetradecahydro-1H-cyclopenta[a]phenanthren-17-yl]pentanoyl]amino]acetic acid and is described in this specification as GCA.

The "Taurocholic acid" is a kind of bile salt, and refers to a compound IUPAC name 2-[[(4R)-4-[(3R,5S,7R,8R,9S,10S,12S,13R,14S,17R)-3,7,12-trihydroxy-10,13-dimethyl-2,3,4,5,6,7,8,9,11,12,14,15,16,17-tetradecahydro-1H-cyclopenta[a]phenanthren-17-yl]pentanoyl]amino]ethanesulfonic acid and is described in this specification as TCA.

The "Cholic acid" is a kind of bile salt, and refers to a compound IUPAC name (4R)-4-[(3R,5S,7R,8R,9S,10S,12S,13R,14S,17R)-3,7,12-trihydroxy-10,13-dimethyl-2,3,4,5,6,7,8,9,11,12,14,15,16,17-tetradecahydro-1H-cyclopenta[a]phenanthren-17-yl]pentanoic acid and is described in this specification as CA.

The "Chenodeoxycholic acid" is a kind of bile salt, and refers to a compound IUPAC name ((4R)-4-[(3R,5S,7R,8R,9S,10S,13R,14S,17R)-3,7-dihydroxy-10,13-dimethyl-2,3,4,5,6,7,8,9,11,12,14,15,16,17-tetradecahydro-1H-cyclopenta[a]phenanthren-17-yl]pentanoic acid and is described in this specification as CDCA.

The "Ursodeoxycholic acid" is a kind of bile salt, and refers to a compound IUPAC name (4R)-4-[(3R,5S,7S,8R,9S,10S,13R,14S,17R)-3,7-dihydroxy-10,13-dimethyl-2,3,4,5,6,7,8,9,11,12,14,15,16,17-tetradecahydro-1H-cyclopenta[a]phenanthren-17-yl]pentanoic acid and is described in this specification as UDCA.

The "Glycodeoxycholic acid" is a kind of bile salt, and refers to a compound IUPAC name 2-[[(4R)-4-[(3R,8R,9S,10S,12S,13R,14S,17R)-3,12-dihydroxy-10,13-dimethyl-2,3,4,5,6,7,8,9,11,12,14,15,16,17-tetradecahydro-1H-cyclopenta[a]phenanthren-17-yl]pentanoyl]amino]acetic acid and is described in this specification as GDCA.

The "Taurodeoxycholic acid" is a kind of bile salt, and refers to a compound IUPAC name 2-[[(4R)-4-[(3R,5R,9S,10S,12S,13R,14S,17R)-3,12-dihydroxy-10,13-dimethyl-2,3,4,5,6,7,8,9,11,12,14,15,16,17-tetradecahydro-1H-cyclopenta[a]phenanthren-17-yl]pentanoyl]amino]ethanesulfonic acid and is described in this specification as TDCA.

The "Hyodeoxycholic acid" is a kind of bile salt, and refers to a compound IUPAC name (4R)-4-[(3R,5R,6S,8S,9S,10R,13R,14S,17R)-3,6-dihydroxy-10,13-dimethyl-2,3,4,5,6,7,8,9,11,12,14,15,16,17-tetradecahydro-1H-cyclopenta[a]phenanthren-17-yl]pentanoic acid and is described in this specification as HDCA.

The "Lithocholic acid" is a kind of bile salt, and refers to a compound IUPAC name (4R)-4-[(3R,5R,8R,9S,10S,13R,14S,17R)-3-hydroxy-10,13-dimethyl-2,3,4,5,6,7,8,9,11,12,14,15,16,17-tetradecahydro-1H-cyclopenta[a]phenanthren-17-yl]pentanoic acid and is described in this specification as LCA.

The "Tauroursodeoxycholic acid" is a kind of bile salt, and refers to a compound IUPAC name 2-[[(4R)-4-[(3R,5S,7S,8R,9S,10S,13R,14S,17R)-3,7-dihydroxy-10,13-dimethyl-2,3,4,5,6,7,8,9,11,12,14,15,16,17-tetradecahydro-1H-cyclopenta[a]phenanthren-17-yl]pentanoyl]amino]ethanesulfonic acid and is described in this specification as TUDCA.

The "Dehydrocholic acid" is a kind of bile salt, and refers to a compound IUPAC name (4R)-4-[(5S,8R,9S,10S,13R,14S,17R)-10,13-dimethyl-3,7,12-trioxo-1,2,4,5,6,8,9,11,14,15,16,17-dodecahydrocyclopenta[a]phenanthren-17-yl]pentanoic acid and is described in this specification as DHCA.

The terms "patient" "subject" "individual" and the like are used interchangeably herein and refers to any animal, or a cell thereof (such as in vitro or in situ), that is capable of completing the methods described herein. In certain non-limiting embodiments, the patient, subject, or individual is a human.

The term "composition" or "pharmaceutical composition" as used herein, can refers to mixture of at least one compounds or compositions used in the present invention and other chemical components such as any additional carriers, stabilizers, suspending agents, dispersing agents, suspending agents, thickening agents, and/or excipients and the like. The pharmaceutical composition promotes the administration of the compound to an organism.

The terms "effective amount", "pharmaceutically effective amount" and "therapeutically effective amount" as used herein, refers to nontoxic and sufficient amount capable of providing desired biological results. The result may be a reduction and/or alleviation of the sign, symptom, or cause of the disease, or any other desired alteration of the biological system. The appropriate therapeutic amount in any individual case can be determined by one of ordinary skill in the art using routine test.

The term "efficacy" as used herein, can refer to the maximum effect (Emax) achieved within the assay.

As used herein, "instructional material" comprises a publication, a recording, a diagram, or any other representation media that can be used to convey the utility of the compound, composition, vector, or delivery system of the present invention in the kit for alleviating the various disease or disorder referred to herein. Selectively, or alternatively, the instructional material can describe at least one method of alleviating a disease or disorder in a cell or tissue of a mammal. The instructional material of the kit of the present invention can be attached to a container comprising the identified compound, composition, vector, or delivery system of the present invention, for example, or can be shipped with a container containing a compound, composition, vector, or delivery system.

Alternatively, the instructive material can be shipped separately from the container, with the intention that the substance and the compound (composition) is used cooperatively by the recipient.

The term "local administration" refers to administering the pharmaceutical ingredient to the muscle or subdermal location, or surrounding thereof of the patient via non-systemic routes. Thus, the local administration excludes administration via systemic routes such as intravenous or oral administration.

The term "Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

A "therapeutic" treatment is a treatment administered to a subject who exhibits signs or symptoms of pathology, for the purpose of diminishing or eliminating those signs or symptoms.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacology.

The term "Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "%" used in the present invention to express content of the composition means the content of w/v % unless otherwise stated, and means the w/v % value based on the total composition unless otherwise stated.

In the present invention, the symbol '/' in the description of 'at least one selected from the group consisting of glycocholic acid or taurocholic acid and salt thereof/phosphatidylcholine' is a fractional representation of a commonly used form.

Hereinafter, the present invention will be described in detail.

The FDA approved Kybella (DCA 1.0%), a cytolytic agent for improving the appearance, and the off-label treated PPC injectable composition (e.g., Lipostabil, Essential, Lipobean) solubilized with DCA, is accompanied by pain and edema due to inflammatory reaction when those are administered with the purpose of localized fat reduction. In addition, those are non-selective cytolytic agent causing the necrosis of fibroblasts, skeletal muscle cells, vascular endothelial cells as well as adipocytes, and fatal side effects such as necrosis at the site of administration, ulcers and mandibular paralysis, and nerve damage have been reported. For this reason, it has been warned not to inject the drugs into the salivary glands, lymph nodes, muscle, or areas very close to it, to prevent potential damage of tissue other than fat. In addition, subjects who are currently receiving Kybella continue to report side effects such as pain, swelling, facial paralysis, and skin necrosis.

In this regard, the inventors of the present invention found that the PPC (5.0%) single composition without solubilizing agent had the equivalent in vitro adipocyte reduction effect of Kybella (DCA 1.0%), but the PPC selectively induced adipocyte reduction by the mechanism of apoptosis and degradation, and the possibility of developing a composition for fat reduction without pain, edema and side effects was confirmed. However, PPC has a limitation in the production of a composition that is physically or chemically stable and safely injectable, because it has poor solubility. Based on this background, the present inventor has studied a composition of adipocyte reducing agent containing PPC as a main component from 2010. As a result, the PPC dispersed in the high pressure homogenizer showed a time- and concentration-dependent effect of adipocytes reduction, but it was limited in industrial use due to low stability.

For this reason, the present inventors conducted formulation tests in a physically and chemically manner to prepare compositions that can safely and stably subcutaneously inject the poorly soluble PPC (FIGS. 1 to 3). This study is based on the assumption that toxicity can be expressed specifically by the surface activity of bile acid (salt). Since the surface activity function inhibits the adipocyte apoptosis and degradation effect inherent to PPC and induces cell lysis by necrosis function, it causes localized fat reduction accompanied by pain, edema and side effects. Therefore, the specific types of surfactant and its use capacity (Ratio) cause significant technical difficulties for those skilled in the art.

The results provided below in the various comparative examples, examples and experimental examples demonstrate the unexpected specific effects of the compositions of the present invention. Briefly, the present inventors selected a combination of bile acid (salt) that were found to have no in situ adverse reaction or have mild adverse reaction in in vivo edema, lesion and inflammation evaluation among the selected compositions which are confirmed to be industrially applicable and safe as a result of the formulation test. Among the selected bile acids (salts), GCA and TCA were selected for adipocyte selectivity in the evaluation of viability of adipocytes, fibroblasts, endothelial cells and skeletal muscle cells in vitro, and then, the effect on adipocyte apoptosis and degradation of the PPC compositions solubilized with GCA or TCA was verified. In addition, it was confirmed that the PPC complex composition solubilized with GCA of the present invention doesn't have not only systemic toxicity but also locally. The results of the researcher's clinical trials with the present invention demonstrate the unexpected discovery that the efficacy of the composition on fat reduction is not inferior to Kybella and that the composition has no pain, edema and side effects or decreased by 80% or more. This will be described in more detail below.

As a result of the test with the bile salts (cholic acid (CA), deoxycholic acid (DCA), glycocholic acid (GCA), taurocholic acid, (TCA), chenodeoxycholic acid (CDCA), ursodeoxycholic acid (UDCA), glycodeoxycholic acid (GDCA), taurodeoxycholic acid, (TDCA), hyodeoxycholic acid (HDCA), tauroursodeoxycholic acid (TUDCA), litho-cholic acid (LCA) and dehydrocholic acid (DHCA) chosen as solubilizing agent for PPC, it was confirmed that LCA and DHCA were not able to solubilize PPC (FIGS. 3A and 3B) and that CA, DCA, GCA, TCA, CDCA, UDCA, GDCA, TDCA, HDCA and TUDCA stably solubilize PPC at a specific molar ratio or more (FIGS. 2A to 2J).

In vivo tests were performed on inflammation, edema and lesions with CA, DCA, GCA, TCA, CDCA, UDCA, GDCA, TDCA, HDCA and TUDCA which are the bile acid selected from the formulation test. Among the bile acid, DCA is the most potent surfactant and is reported to cause inflammation, swelling and clinical side effects caused by nonselective cell lysis. Therefore, the present inventor was aware that additives showing harmful effect like DCA among the bile acid are not suitable solubilizing agent because they inhibit the inherent activity of PPC on selective adipocyte apoptosis and degradation. Then, first, in vivo injections of bile acids at different concentrations were performed to investigate edema, skin lesions and inflammation, which are the representative harmful examples.

As a result of edema test in vivo with the bile acids (FIGS. 4A to 4G), at 2 hours after administration it was confirmed that:

"None"—PPC (2.50-5.0%) complex composition solubilized with GCA (1.25-2.5%) or TCA (1.25-2.5%), "Mild"—single compositions of PPC (1.25-10.0%), GCA (1.0%), TCA (1.0%) and TUCA (1.0%,2.5%), and complex compositions of PPC (7.5%,10.0%)+GCA (3.75%, 5.0%) and PPC (7.5%, 10.0%)+TCA (3.75%, 5.0%), "Moderate"—single compositions of PPC (12.5%, 15.0%), UDCA (1.0%), GDCA (1.0%), CDCA (1.0%), CA (1.0%), GCA (2.5%, 5.0%), TCA (2.5%, 5.0%) and TUDCA (5.0%, 7.5%), and complex composition of PPC (5.0%)+CA (2.5%), PPC (15.0%)+GCA (7.5%) and PPC (15.0%)+TCA (7.5%), "Severe" and "Extremely severe"—The other single compositions and complex compositions.

Compare to the PPC (5.0%) solubilized with DCA (2.2%) showing extremely severe edema, PPC (2.5-15.0%)+GCA (1.25-7.50%) complex composition (FIG. 4N) and PPC (5.0%)+GCA (2.5-7.5%) complex composition (FIG. 4P) of the present invention is surprising invention without edema. The surprising finding is that the extent of edema observed with GCA or TCA alone injection dramatically decreases in PPC+GCA and PPC+TCA complex compositions. However, the composition of DCA alone or 5.0% PPC solubilized with 2.2% showed extremely severe edema after administration suggesting that DCA has an effect of inducing cell necrosis and interrupting PPC-inherent selective adipocyte apoptosis and degradation (FIG. 4M).

As a result of skin lesion test in vivo (FIGS. 5A to 5F), at 2 hours after administration it was confirmed that:

"None"—single compositions of PPC (1.25-15.0%), GCA (1.0%), TCA (1.0%) and TUDCA (1.0-7.5%), and complex compositions of PPC (2.5-10.0%)+GCA (1.25-5.0%) and PPC (5.0%)+GCA (2.5-5.0%), "Mild"—single compositions of HDCA (1.0%), CA (1.0%), GCA (2.5%, 5.0%) and TCA (2.5%, 5.0%), and complex composition of PPC (15.0%)+GCA (7.5%), "Moderate"—single compositions of DCA (1.0%), UDCA (1.0%), TDCA (1.0%), GDCA (1.0%), CDCA (1.0%), CA (2.5%), GCA (7.5%) and TCA (7.5%), "Severe" and "Extremely severe"—The other single compositions and complex compositions.

These results were consistent with the edema test result and it was confirmed that the subcutaneous injection of PPC+GCA or PPC+TCA complex composition alleviated the lesion symptoms compared to GCA or TCA single composition.

As a result of H&E inflammation test in vivo (FIGS. 6A to 6F), it was confirmed that:

"None"—single compositions of PPC (2.5-7.5%), TUDCA (1.0-5.0%), and complex compositions of PPC (2.5-7.5%)+GCA (1.25-3.75%), PPC (5.0%)+GCA (2.5-7.5%), PPC (5.0%)+TCA (2.5%) and PPC (5.0%)+TUDCA (4.0%), "Mild"—single compositions of PPC (10.0%, 12.5%), GCA (1.0%), TCA (1.0%) and TUDCA (7.5%), and complex compositions of PPC (10.0%)+GCA (5.0%), PPC (5.0%)+GCA (10.0%), "Moderate"—single compositions of PPC (15.0%), TDCA (1.0%), GDCA (1.0%), CDCA (1.0%), CA (1.0%) and GCA (2.5% and more) and TCA (2.5% and more), and complex compositions of PPC (15.0%)+GCA (7.5%) and PPC (5.0%)+CA (2.5%), "Severe" and "Extremely severe"—The other single compositions and complex compositions.

These results were consistent with the edema and lesion test result proving that the toxicity of GCA or TCA single injection is not toxic or alleviated when complexed with PPC, but DCA or its equivalent bile acids cause pain, edema and side effects caused by necrosis which interrupts PPC-inherent activity of apoptosis and degradation.

As a result of in vitro adipocyte viability test on the PPC compositions solubilized with the solubilizing agents TUDCA, TCA and GCA selected on the basis of the above formulation test, and edema, inflammation and skin lesion in vivo test results of the bile acids, the group of PPC single composition, the group PPC solubilized with GCA or TCA showed reduced adipocyte viability in time and concentration dependent manner (FIGS. 7A to 7D). There was an unusual finding that TUDCA inhibits the adipocyte apoptosis and degradation. In this regard, study results on cell apoptosis inhibition of TUDCA have been published (Andrew L. Rivard, Administration of Tauroursodeoxycholic acid reduced apoptosis following myocardial infarction in rat, The American Journal of Chinese Medicine, Vol. 35, No. 2, 279-295, 2007), suggesting that PPC acts differently on cell necrosis and apoptosis.

PPC 5.0% single, PPC 5.0%+GCA 2.5%, and PPC 15.0%+TCA 7.5% showed similar activities of adipocyte reduction at the time of 96 hours with DCA 1.0%. That is, the group of PPC 5.0% single and PPC 5.0%+GCA 2.5% showed the same adipocyte viability as Kybella (DCA 1.0%) which is an FDA-approved cytolytic agent for appearance improvement, and there was no statistically significant difference in adipocyte reduction effect in these experimental groups (FIG. 7E). Taken together, it is important to select the solubilizing agent, which is selected to prepare PPC as an injectable composition for localized fat reduction, from bile acids that are low in toxicity, such as having no interrupting activity on the PPC-inherent adipocyte selective apoptosis and degradation with necrosis (or this toxicity can be counteracted by PPC) and can provide safety of the composition and formulation stability. That is, it was surprisingly found that solubilizing agent without negative transformation (PPC+DCA) or inhibition (PPC+TUDCA) activity, such as necrosis, on the PPC-inherent fat reduction effect should be selected.

As a result of in vitro adipocyte viability test on GCA single composition at the molar ratio mixed for PPC solubilizing, GCA showed reduced adipocyte viability in time and concentration dependent manner. And there was no statistically significant difference in adipocyte viability between PPC single composition and PPC composition solubilized with GCA (FIGS. 7F to 7H). That is, the adipocyte apoptotic effect of the PPC single composition and the PPC composition solubilized with GCA was equivalent. To examine the effect of GCA on adipocyte reduction in the composition of the present invention, the adipocyte reducing effect of PPC with increasing GCA input was observed. As a result of adipocyte viability test at 96 hours after PPC (5.0%) complex composition solubilized with GCA (2.5-8.75%) and PPC (5.0%) single composition, the effect of PPC (5.0%) complex composition solubilized with GCA (2.5-7.5%) was not statistically significant in comparison with PPC (5.0%) single composition. That is, the groups were equivalent in adipocyte apoptotic effect. However, the PPC (5.0%) solubilized with GCA (8.75%) treated group showed the statistically significant difference in adipocyte apoptotic effect (FIG. 7I). These results suggest that the inherent positive performance of PPC may be adversely affected when the molar ration of GCA/PPC is 3.04 mol/mol (PPC 5.0%+GCA 8.75%) or more.

According to the previous report, DCA or PPC composition solubilized with DCA has been reported to cause clinically fatal side effects by lysing not only adipocytes, but also fibroblasts, skeletal muscle cells and vascular endothelial cells. As a result of observation of cell viability with the PPC single composition and the PPC complex composition solubilized with GCA, it was surprisingly found that PPC+GCA selectively reduces adipocytes, differently from PPC+DCA (FIGS. 8A to 8D). The composition of the present invention is a selective adipocyte reduction composition causing fat reduction safely without fatal side effects such as cutaneous necrosis, mandibular nerve palsy, dysphagia, those are caused by commercially available cytolytic agent Lipostabil® N,iv (PPC+DCA) and Kybella i.v. (DCA).

To evaluate whether the reduction of adipocytes was due to necrosis or apoptosis and degradation, the effect on adipocyte apoptosis through caspase 3 activity and the effect on adipocyte lipolysis through glycerol release was observed.

The PPC single composition and the PPC+GCA complex composition showed a time-dependent effect of inducing caspase-3 activity to a considerable level. However, the PPC+DCA complex composition inhibited capase-3 activity compared to PPC or PPC+GCA. Interestingly, DCA 1.0% showed some caspase-3 activity up to 24 hours, but after 48 hours, caspase-3 activity returned to pretreatment levels. This phenomenon is considered to be due to the fact that the action against cell apoptosis is partially observed until 24 hours immediately after treatment with the DCA single composition, and then the action is turned into the cell necrosis pathway by the inflammatory reaction (FIGS. 10A and 10B).

At 24 hours after treatment, the test materials except for DCA 1.0% and PPC 5.0%+GCA 5.0% induced glycerol secretion similarly. At 48 hours after treatment, PPC single, PPC+DCA, DCA single, and GCA single groups showed slightly higher cytolytic activity than at 24 hours. Particularly, the PPC+GCA group showed a much higher cell apoptotic effect than the PPC single composition (FIGS. 10C and 10D).

As a result, the PPC single composition and the PPC+GCA complex composition contributed to the specific effect of reducing adipocytes due to the apoptosis and lipolysis mechanism differentiated from the necrosis mechanism of PPC+DCA. With the such mechanism, it was found that when the composition of the present invention is administered to the subcutaneous fat layer, fat is reduced without pain, edema and side effects.

Based on the effect of in vitro adipocyte reduction, the in vivo H&E histopathological tests were performed with PPC single composition (2.5%, 5.0%, 10.0% and 15.0%), PBS (negative control) and Isuprel (positive control), DCA 1.0%, GCA 2.5% PPC 5.0%+DCA 2.2%, PPC 5.0%+HDCA 2.5%, PPC 5.0%+UDCA 3.0%, PPC 5.0%+TDCA 2.5%, PPC 5.0%+GDCA 2.5%, PPC 5.0%+CDCA 2.5%, PPC 5.0%+CA 2.5%, PPC 5.0%+TUDCA 4.0%, PPC 5.0%+TCA 2.5% and PPC (2.5-10.0%)+GCA (1.25-5.0%). As a result, the adipose tissue injected with the DCA single or the PPC+DCA complex composition showed severe inflammation in the administration area, and the cell was dissolved by necrosis, and remarkable destruction was induced. The DCA single composition showed a severe inflammation level even though DCA was contained at a low concentration of 1%, and the inflammatory induction action was greater than that of GCA single composition. The complex composition of PPC+GCA showed that the fat cells became smaller, the apoptotic cells was clearly observed, and the adipocyte changed into the adipocytes formed by the fusion of collapsed adipocytes, the degree of inflammation induction was low at all concentration treated, and morphological features were found to damage only adipocyte membrane (FIG. 11A to 11D).

Taken together the results of the formulation test, in vivo edema, inflammation and skin lesion test results, in vitro fat cells, muscle cells, fibroblasts, endothelial cell viability test results, and in vivo fat pad H&E histopathological test results, the PPC complex composition solubilized by GCA of the present invention has a markedly lower local toxicity than the PPC complex composition solubilized by the marketed product DCA and GCA single composition. To verify these results in accordance with good laboratory practice (GLP), a single dose toxicity study was conducted on beagle dogs by calculating the clinical dose. As a result, it was confirmed that the complex composition of the present invention was not toxic (FIGS. 12A to 12C).

To assess the degree of in vivo pain, the distance and speed of movement of the mice were measured after administration of each experimental compositions. Except for PPC single preparation and GCA+PPC preparations, the distance and speed of movement were significantly reduced in all experimental groups compared with before administration. And the results showed that the distance and speed of movement were not changed or slightly increased in the group treated with PPC 5.0% single composition, PPC 5.0%+TUDCA 4.0%, PPC 5.0%+GCA 2.5% or PPC 5.0%+TCA 2.5%. On the other hand, the distance and speed of movement were decreased by 20% in the mouse group treated with PPC 5.0%+DCA 2.2%, PPC 5.0%+HDCA 2.5%, PPC 5.0%+UDCA 3.0%, PPC 5.0%+TDCA 2.5%, PPC 5.0%+GDCA 2.5%, PPC 5.0%+CDCA 2.5% or PPC 5.0%+CA 2.5%, and it was judged that the activity decreased due to the pain (FIGS. 13A and 13B).

Based on the results of the formulation test, in vivo edema, inflammation and skin lesion test results, in vitro fat cells, muscle cells, fibroblasts, endothelial cell viability test results, in vivo fat pad H&E histopathological test results, single-dose toxicity test results and pain test results, safety and efficacy were evaluated before and after administration to huma subjects for clinical validation. The results of the clinical studies of the researchers showed that 12 weeks after the injection at submental fat, 0.2 cc, 1 cm interval, 6 to 8 mm depth, total 50 points, dose of 10 ml, 6 times at intervals of 4 weeks, it was visually confirmed that the submental fat was reduced (FIG. 14A). The level of satisfaction reported by the subject was 4 out of 5, and the improvement after the comparison with the pre-dose photographs was reported as 1.5 grades (FIG. 14A). In addition, the submental fat was decreased on CT by 30.36%, from 5.6 mm before the administration to 3.9 mm 12 weeks after the final administration (FIG. 14B).

Six male and female patients who had received PPC injection composition solubilized with DCA (previously commercialized products) were subjected to clinical evaluation of pain, edema and side effects after administration of the GCA-solubilized PPC injectable composition of the present invention. After topical anesthesia with 9.6% lidocaine cream for 30 minutes or more to subjects having experience with an injection of the composition (PPC 2.5%+DCNa 1.2%) comprising physiological saline and Lipobean® (an injection of PPC 5.0% solubilized with DCNa 2.4%) mixed at a ratio of 1:1 in the abdomen and flank (1.5 cm interval, 10 to 12 mm depth, 0.5 cc per point, from 50 ml to 100 ml per administration) with a syringe equipped with a 13 mm needle or in the submental fat (1.0 cm interval, 6 to 8 mm depth, 0.2 cc per point, 10 ml per administration), and administered the composition of the present invention (5.0% PPC injection solubilized with 2.8% GCA or 5.0% PPC injection solubilized with 4.0% GCA) to the subjects with the same administration method. As a result of the test, subjects who had received the injection of PPC composition solubilized with DCNa complained pain and edema especially at the time of administration and 10 days after administration, and skin lesions such as erythema, hematoma, bruises and local injuries such as induration, nodule, pruritus, and burning sensation were also reported. Surprisingly, however, the subjects receiving the PPC injections solubilized with the GCA of the present invention were alleviated to a mild level, particularly to the point where pain (FIG. 15A) and edema (FIG. 15B) were substantially absent. That is, the safety was improved by 80% or more as compared with the group that received PPC injection solubilized with DCA, and severe adverse reactions among the subjects were not reported (FIGS. 15A to 15C). Specifically, no side effects such as swelling, hematoma, bruising, erythema, paresthesia, induration, nodule and pruritus were observed or observed at a significantly low level.

In addition, when PPC solubilized with GCA was administered to the abdomen and flank at 0.5 cc, 1.5 cm interval, 12 mm depth, total 200 points, dose of 100 ml, the skin lesions were not visually observed (FIG. 16). As shown in FIG. 16, erythema was reduced to none or mild except for the bruise caused by the injection needle itself or blood vessel damage caused by vascular injury at the time of injection. And the paresthesia, broad swelling, induration, paresthesia, nodule, pruritus, burning sensation, dysphagia, and the like were not observed (FIG. 15C).

In summary, the composition of the present invention is an innovative invention that it selectively reduces adipocyte with the mechanism of apoptosis and degradation, reduces patient's anxiety and discomfort, improve patient's compliance with medicines, and has formulation stability. And the composition of the present invention doesn't cause pain and edema, that is caused by inflammation after administering the conventional injectable composition of DCA or PPC solubilized with DCA, and extensive swelling, erythema, discomfort like bruise and anesthesia, induration, paresthesia, nodule, pruritus, burning sensation, nerve injury and dysphagia, that is caused by non-selective cytolytic activity.

Therefore, there is provided a composition for reducing localized fat with a reduced pain and side effect, the composition comprising:
(i) phosphatidylcholine; and
(ii) at least one selected from the group consisting of glycocholic acid (GCA), taurocholic acid (TCA) and salt thereof,
wherein a molar ratio of (ii) to (i) in the composition is in a range of 0.7 to 3.0.

In addition, there is provided a composition for reducing localized fat with a reduced pain and side effect, the composition essentially consisting of:
(i) phosphatidylcholine; and
(ii) at least one selected from the group consisting of glycocholic acid (GCA), taurocholic acid (TCA) and salt thereof,
wherein a molar ratio of (ii) to (i) in the composition is in a range of 0.7 to 3.0.

Specifically, there is provided a composition for reducing localized fat with a reduced pain and side effect, the composition comprising:
(i) phosphatidylcholine;
(ii) at least one selected from the group consisting of glycocholic acid (GCA), taurocholic acid (TCA) and salt thereof; and
(iii) water (or water for injection)
wherein a molar ratio of (ii) to (i) in the composition is in a range of 0.7 to 3.0.

In addition, there is provided a composition for reducing localized fat with a reduced pain and side effect, the composition essentially consisting of:
(i) phosphatidylcholine;
(ii) at least one selected from the group consisting of glycocholic acid (GCA), taurocholic acid (TCA) and salt thereof; and
(iii) water (or water for injection)
wherein a molar ratio of (ii) to (i) in the composition is in a range of 0.7 to 3.0.

The fat reducing injectable composition of the present invention can be applied to a localized area and is preferably applied to the fat, lipoma deposited to abdomen, submental, forearm, thigh, waist, hip, under eye, brassiere line, and the like, but not limited thereto, and can be applied to neck wrinkle improvement.

The composition of the present invention is preferably used for non-surgical removal of localized fat deposition in a subject. The term 'non-surgical' refers to a medical procedure that does not require an incision.

The formulation of the composition of the present invention is not particularly limited as long as it is used for the purpose of reducing fat (in particular, reducing localized fat), and includes, for example, an injection such as patch, depot, etc., and preferably it can be an injectable composition.

That is, the present invention relates to a composition or preparation that can be injected directly into a treatment site of a patient in need of fat removal without surgery.

The injectable composition for reducing localized fat of the present invention is a pharmaceutical composition for the treatment of adipose tissue hyperplasia or hyperproliferative disorder (disease), and the disorder is not particularly limited as long as it is known in the art to be hyperproliferative or hyper-accumulative of the adipose tissue pathologically, for example, obesity (abdominal obesity), lower eyelid escape, lipoma, Dercum's disease, Madelung's neck, fatty edema, piezogenic nodules, Xanthosis, fat dystrophy, fat accumulation associated with cellulite, and the like, but not limited thereto.

Methods of administering the injectable composition of the present invention are not limited, but can be administered by a method suitable for the patient in view of the severity of the disease, the age, sex and other conditions of the patient. Such an administration route is not particularly limited in the method, but is preferably administered directly to the subcutaneous fat layer (tissue), for example, multiple, subcutaneous or intradermal injection at 0.5 to 2.0 cm intervals in the lattice interval.

In the present invention, the term side effect refers to the side effects of the PPC preparations which comprise specific bile salts that has been known or commercially available, in particular conventional DCA-solubilized PPC injections (e.g., Lipostabil, Essential, Lipobean) or DCA single preparation (e.g., Kybella) known as injections for reducing localized fat. And it refers to a harmful action to the human body other than the main action that is expected as a therapeutic effect of drugs (in the present invention, fat reducing effect). Specifically, the side effect is at least one selected from the group consisting of edema, anesthesia (especially anesthesia of administration sites), extensive swelling, erythema, hematoma, bruising, induration, sensory abnormalities, nodules, pruritus, burning sensation, dysphagia and necrosis of cells other than adipocytes (muscle cells, fibroblasts, vascular endothelial cells, etc.), and the like except for the hematoma and bruise caused by the injection needle itself, but not limited thereto. The injectable composition for reducing localized fat of the present invention is characterized in that local adverse reactions are alleviated to such an extent that side effects are substantially absent.

As used herein, the term "alleviation of pain and side effects" comprises the meaning that the pain and side effects are reduced, eliminated, present in low level (partially removed), substantially absent (substantially removed), and completely absent (completely removed).

In the present invention, the pain and edema include pain at the time of injection administration and pain and edema after administration. The present invention is characterized by a significantly reduced pain and edema (substantially no pain and edema), as opposed to conventional commercially available DCA single compositions or PPC injections solubilized with DCA, which involve pain and edema. These painless and edema-absent PPC injections are first disclosed in the present invention, and in particular, it is characterized in that there is no secondary pain and edema lasting more than 10 days due to inflammation, as well as primary pain at the time of injection and immediately after administration. In the present invention, the meaning of the pain is distinguished from the symptoms caused by the invasion of the needle (e.g., sickness, bruising by a needle, hematoma by a needle, swelling by a needle), and it means pain or edema (inflammation) that has been caused by the feature of the DCA single injection or DCA+PPC injectable composition itself. In one embodiment of the present invention, the PPC+GCA complex preparation of the present invention showed, uniquely, hardly any pain at the time of injecting as compared to the TPC injection solubilized with DCA", that is commercially available, used as a control group (FIG. 15A). Considering that the complex preparation of the present invention is similar to existing commercially available preparations (representative example of PPC injection solubilized with DCNa) in particle characteristics (micelle, particle size, etc.) and that all of the injections are administered at a pH similar to the human body, the effect of the composition of the present invention is difficult to predict from previously known technologies.

In addition, the composition of the present invention is characterized by causing apoptosis and lipolysis specifically to adipocytes. In one embodiment of the present invention, the PPC+GCA complex preparation of the present invention does not substantially affect other cells other than adipocytes such as fibroblasts, skeletal muscle cells and vascular endothelial cells, and it was confirmed that induction of apoptosis and lipolysis was specifically effective only in adipocytes (see FIGS. 8A to 8D). This effect is comparable to PPC preparations solubilized with other bile acids (representatively, commercially available PPC+DCA preparations), which causes necrosis to other cells than adipocytes. It is first disclosed in the present invention that it possesses an adipocyte-specific (selective) effect when GCA is mixed with PPC at certain ratios.

Injectable preparations are prepared by dissolving the main drugs (PPC solubilized with GCA in the present invention) and, if necessary, other additives in the water for injection, filtering the solution with a bacterial filter, sterilizing the solution, filling the solution in a vial, ampoule or free field syringe followed by sealing. Therefore, in preparing injections, water for injection as well as water can be used to fill the remaining amount. The water for injection is not particularly limited as long as it is distilled water for injection or a buffer solution for injection intended for diluting solid injections or water-soluble injectable solution. For example, a phosphate buffer solution or sodium dihydrogenphosphate ($NaH_2PO_4$) in a range of pH 3.5 to 7.5—citric acid buffer solution or the like can be used. The phosphate used herein may be in the form of sodium salt or potassium salt, or may be in the form of anhydride or hydrate, and may be in the form of citric acid or anhydride or hydrate. Examples of the water for injection includes glucose injection, xylitol injection, D-mannitol injection, fructose injection, physiological saline, dextran 40 injection, dextran 70 injection, amino acid injection, Ringer's solution and lactic acid-ringer solution, but is not limited thereto.

In the present invention, the phosphatidylcholine (PPC) is a phospholipid widely found in animals, plants, yeasts and fungi. It is also called lecithin, polyenophosphatidylcholine and 3-sn-phosphatidylcholine and has a basic structure of Formula 1. It is a membranous phospholipid of mammals, mainly in the brain, nerves, blood cells, egg yolk, and the like. In plants, it is contained in soybean, sunflower seed, wheat germ, and is rarely found in bacteria. In general, saturated fatty acids are bonded to the 1-position of glycerol, unsaturated fatty acids are bonded to the 2-position, and most of the acyl groups are C12 to C22 (12 to 22 carbon atoms).

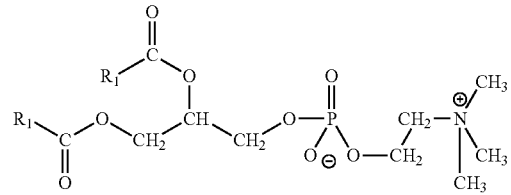

<Formula 1>

The phosphatidylcholine of the present invention has the structure as shown in Formula 1, R1 is a saturated or unsaturated fatty acid having 12 to 22 carbon atoms, and R2 is a saturated or unsaturated fatty acid having 12 to 22 carbon atoms. The saturated or unsaturated fatty acid may be in the form of a straight chain or branched chain, and the unsaturated fatty acid may include monounsaturated or multiple (e.g., double, triple, or quadruple) unsaturation. The phosphatidylcholine of the present invention may be a single compound or may be a mixture of various compounds having different carbon numbers of the R1 and R2 acyl groups. Preferably, the phosphatidylcholine of the present invention can have a molecular weight of 700 g/mol to 1000 g/mol, and more preferably a molecular weight of 750 g/mol to 800 g/mol.

The phosphatidylcholine of the present invention can be extracted from any one selected from the group consisting of various animals or plants, for example, soybean, sunflower seed, wheat germ, and egg yolk. Alternatively, the commercially available phosphatidylcholine of the present invention can be purchased and used, or a product prepared by a chemical synthesis method known in the art can be used.

The phosphatidylcholine of the present invention may be preferably isolated from soybean or egg yolk. In general, the typical structure of phosphatidylcholine isolated from soybean is as following Formula 2. And, in general, the typical structure of phosphatidylcholine derived from egg yolk is as shown below in Formula 3. The phosphatidylcholine used in the present invention may be a single compound consisting only of the compound of the following Formula 2 or 3, or mixtures in which several compounds having different carbon numbers of the R1 and R2 acyl groups based on the Formula 1 are further included. The mixture may contain substantially 50% by weight or more, more preferably 70% by weight or more, and most preferably 90% by weight or more of the compound of the following Formula 2 or 3.

(GCA), taurocholic acid (TCA) and salt thereof (hereinafter abbreviated as (ii)) to phosphatidylcholine (PPC, hereinafter abbreviated as (i)) is in a range of 0.7 to 3.0. In other words, the molar ratio of (ii) to (i) may be in a range of 0.7 to 3.0, more preferably the molar ratio of (ii) to (i) may be in a range of 0.7 to 2.60, and most preferably the molar ratio of (ii) to (i) may be in a range of 0.7 to 1.73. When those are contained at a molar ratio (mol/mol) of less than 0.7, it is difficult to form stable micelles, resulting in poor formulation stability. Therefore, lower limit value of the molar ratio is preferably 0.70 or more, and more preferably 0.76. When the upper limit value of the molar ratio is 3.04 or more, pain, edema and side effects are markedly exhibited with mild or more of inflammation, moderate or more of edema, and severe or more of skin lesion, respectively, and limits the inherent function of the PPC with cell necrosis rather than giving a positive effect on the apoptosis and lipolysis of adipocyte. At the molar ratio of 3.0 or less, these side effects and pain were markedly reduced. Particularly, when they were included at the molar ratio of 2.60 or less, edema, lesion and inflammation were not observed or mild symptoms were observed. Clinically, slight edema may be seen, but this is a level substantially free from pain and side effects, and thus is adopted as a more preferable range in the

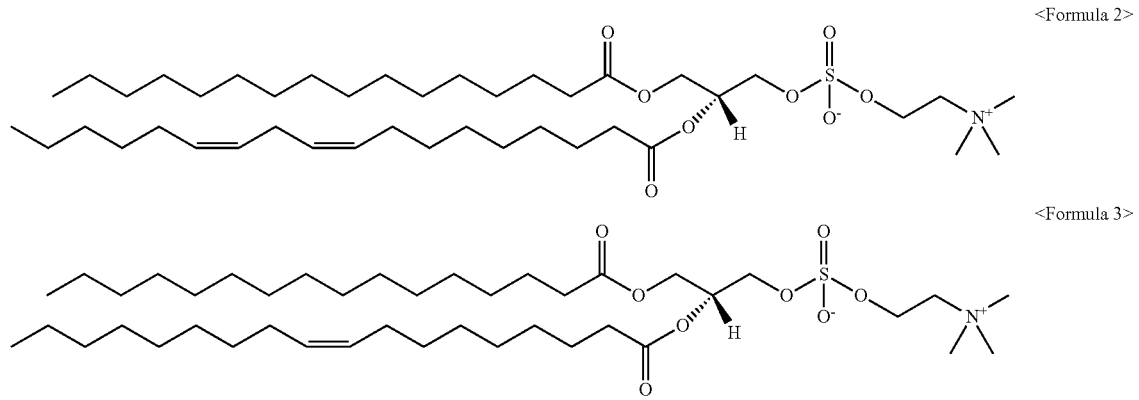

<Formula 2>

<Formula 3>

Most preferably, the phosphatidylcholine of the present invention may be extracted from soybean and may be a mixture containing a compound having a structure as shown in Formula 2 at a ratio of 93.0% by weight or more.

In the injectable composition for reducing localized fat of the present invention, the phosphatidylcholine is contained at a concentration of 0.625 to 15.0% (w/v) based on the total composition, preferably contained at a concentration of 1.25 to 12.5% (w/v), and more preferably contained at a concentration of 2.5 to 10.0% (w/v) in the total composition. Most preferably, the phosphatidylcholine may be contained at a concentration of 2.5 to 7.5% (w/v) based on the total composition. When the concentration of phosphatidylcholine is less than 0.625% (w/v), there is no lipolysis effect (see FIGS. 7A to 7D). When the concentration of phosphatidylcholine is more than 15% (w/v), it is inconvenient to administer multiple doses to the subcutaneous fat layer due to its high viscosity, and since excessive use of solubilizing agent is required, moderate abnormality of inflammatory reaction is manifested and serious side effects such as pain, swelling and inflammation may occur.

The composition for reducing localized fat of the present invention is characterized in that a molar ratio or at least one selected from the group consisting of glycocholic acid present invention. Most preferably, when the molar ratio is 1.73 or less, edema and lesion, and clinical pain and edema caused by inflammation do not occur.

In the present invention, the range of the molar ratios of (ii) to (i) includes a range in which the minimum or maximum boundary value are selected from the group consisting of the value 0.70, 0.71, 0.72, 0.73, 0.74, 0.75, 0.76, 0.77, 0.78, 0.79, 0.80, 0.81, 0.82, 0.83, 1.09, 1.05, 1.06, 1.07, 1.08, 1.09, 1.10, 1.09, 1.08, 1.09, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.53, 1.54, 1.55, 1.56, 1.57, 1.58, 1.59, 1.60, 1.50, 1.54, 1.50, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.2 2.42, 2.43, 2.44, 2.45, 2.46, 2.47, 2.48, 2.32, 2.33, 2.34, 2.62, 2.63, 2.64, 2.65, 2.66, 2.67, 2.68, 2.69, 2.70, 2.71, 2.72, 2.73, 2.50, 2.52, 2.53, 2.54, 2.55, 2.56, 2.57, 2.58, 2.59, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.99, and 3.00. As a most preferred example of the present invention, a boundary value of 0.76 and 1.39 can be selected from among the ranges of the molar ratios of the present invention described above. Thus, it is obvious to a person skilled in the art that the range of the molar ratios of 0.76 to 1.39, that is, all the values in the range from 0.76 or more to 1.39 or less can be applied to the present invention.

Specifically, the composition for reducing localized fat of the present invention is characterized by containing 'Glycocholic acid or a salt thereof' in the composition in a specific mixing ratio. The glycocholic acid is a bile salt that has a molecular weight of about 465.63 g/mol and can be described herein as GCA or GC. The glycocholic acid may be used in the form of a pharmaceutically acceptable salt. As used herein, the term "pharmaceutically acceptable" means physiologically acceptable and does not normally cause allergic reactions or similar reactions when administered to humans, and includes, but not limited to, sodium salt, potassium salt or ammonium salt. Preferably, the glycocholic acid salt of the present invention may be sodium glycocholate (GCNa).

The Glycocholic acid or its salt can be extracted from an animal's intestine according to a method known in the art, and can be commercially purchased or used by a chemical synthesis method known in the art.

More specifically, the minimum molar ratio of GCA to PPC (GCA/PPC) for preparing a clear solution capable of microfiltering and a mixed micelle with the diameter of 10 nm or less that can be subcutaneously injected safely and stably is 0.76 (PPC 5.0%+GCA 2.2%). At a molar ratio less than the minimum molar ratio, the stability of the preparation is low due to the precipitation phenomenon. Therefore, the glycocholic acid or its salt may preferably be contained so that the molar ratio of GCA to PPC (GCA/PPC) is in a range of 0.76 to 3.0 (GCA 2.2 to 8.65% (w/v) based on PPC 5%), and the specific range refers to the above-mentioned molar ratio. When the glycocholic acid is used in its salt form, the molar ratio may preferably be calculated based on only the glycocholic acid moiety in the glycocholic acid salt.

The composition for reducing localized fat of the present invention is characterized by containing 'Taurocholic acid or a salt thereof' in the composition in a specific mixing ratio. The taurocholic acid is a bile salt that has a molecular weight of about 515.71 g/mol and can be described herein as TCA. The Taurocholic acid may be used in the form of a pharmaceutically acceptable salt. As used herein, the term "pharmaceutically acceptable" means physiologically acceptable and does not normally cause allergic reactions or similar reactions when administered to humans, and includes, but not limited to, sodium salt, potassium salt or ammonium salt. Preferably, the glycocholic acid salt of the present invention may be sodium glycocholate (TCNa).

The taurocholic acid or its salt can be extracted from an animal's intestine according to a method known in the art, and can be commercially purchased or used by a chemical synthesis method known in the art.

More specifically, the minimum molar ratio of TCA to PPC (TCA/PPC) for preparing a clear solution capable of microfiltering and a mixed micelle with the diameter of 10 nm or less that can be subcutaneously injected safely and stably is 0.78 (PPC 5.0%+TCA 2.5%). At a molar ratio less than the minimum molar ratio, the stability of the preparation is low due to the precipitation phenomenon. Therefore, the glycocholic acid or its salt may preferably be contained so that the molar ratio of TCA to PPC (TCA/PPC) is in a range of 0.78 to 3.0 (TCA 2.5 to 9.57% (w/v) based on PPC 5%), and the specific range refers to the above-mentioned molar ratio. When the taurocholic acid is used in its salt form, the molar ratio may preferably be calculated based on only the taurocholic acid moiety in the taurocholic acid salt.

At this point, the at least one (substance) selected from the group consisting of glycocholic acid (GCA), taurocholic acid (TCA) and salt thereof is preferably contained at the same weight (or weight/volume percentage (that is, % w/v)) as the phosphatidyl choline or less. For example, the weight ratio based on PPC may be in the range of 1:0.1 to 1. Specifically, the weight ratio based on PPC can be 1:0.1, 1:0.2, 1:0.3, 1:0.4, 1:0.5, 1:0.6, 1:0.7, 1:0.8, 1:0.9 or 1. When such a weight standard is applied on the basis of the molar ratio (GCA/PPC molar ratio or TCA/PPC molar ratio), the molar ratio may preferably be in the range of 0.7 to 1.73, more preferably 0.76 to 1.73.

Preferably, at least one (substance) selected from the group consisting of glycocholic acid (GCA), taurocholic acid (TCA) and salt thereof is contained less than the weight (or weight/volume percentage (that is, % w/v)) of the phosphatidyl choline. For example, the weight ratio based on PPC may be in the range of 1:0.1 to 0.999. Specifically, the weight ratio based on PPC can be 1:0.1, 1:0.2, 1:0.3, 1:0.4, 1:0.5, 1:0.6, 1:0.7, 1:0.8 or 1:0.9. When such a weight standard is applied on the basis of the molar ratio (GCA/PPC molar ratio or TCA/PPC molar ratio), the molar ratio may preferably be in the range of 0.7 or more to less than 1.73, more preferably 0.76 or more to less than 1.73.

When the glycocholic acid or taurocholic acid is used in the form of a salt thereof, the weight ratio may preferably be calculated based on only the ratio of the glycocholic acid moiety in the glycocholic acid salt or the ratio of the taurocholic acid moiety in the taurocholic acid.

The at least one selected from the group consisting of glycocholic acid (GCA), taurocholic acid (TCA) and salts thereof can be used as follows:

(A) the individual substance alone (glycocholic acid, one of the salts of glycocholic acid, taurocholic acid, one of the salts of taurocholic acid) may be complexed with PPC, or (B) a mixture of GCA or its salts; and TCA or a salt thereof (hereinafter, GCA-TCA mixture) may be complexed with PPC.

As described above, the composition of the present invention wherein GCA, TCA or a salt thereof is contained in a specific mixing ratio with phosphatidylcholine (PPC) is characterized by being a non-liposome micelle preparation. That is, the composition of the present invention is characterized by the presence of phosphatidylcholine in micelle form in the composition, which is different from the conventional PPC formulations using a liposome system.

The GCA, TCA, or salts thereof are contained in the fat reducing injectable composition of the present invention in a specific dose (or a mixing ratio, molar ratio) as described above, so that they are not only excellent in formulation stability but also, unlike the conventional solubilizing agents (especially deoxycholate and its salt type) contained in the PPC injectable composition that cause side effects such as necrosis of the cell accompanied with body pain and edema, hematoma, anesthesia, erythema, swelling, induration, pruritus, nodule, and the like, induces high-efficient lipolysis and adipocyte apoptosis action together with PPC, so that the pain and the side effect are substantially eliminated, and shows excellent effect in fat reduction (pain and edema were reduced by 80% or more, erythema, hematoma, induration, pruritus, and nodules were reduced by more than 80%). Therefore, it is also a feature of the present invention that the anti-inflammatory agent and/or analgesic component for separate pain management is not necessarily included or combined in the composition.

Meanwhile, the composition of the present invention may further comprise at least one selected from the group consisting of a preservative; an isotonic agent; and a pH adjuster.

Specifically, the composition for reducing localized fat of the present invention may preferably further comprise at least one selected from the consisting of 0.1 to 5% (w/v) of the preservative, 0.1 to 10% (w/v) of the isotonic agent and 0.01 to 2% (w/v) of the pH adjuster based on the total composition.

The preservative may be selected from the group consisting of benzyl alcohol, lidocaine, procaine, and chlorobutanol, but not limited thereto. More preferably benzyl alcohol. The benzyl alcohol is one of the aromatic alcohols and is a colorless transparent liquid. The concentration of the benzyl alcohol contained in the injectable composition of the present invention may be preferably 0.1% (w/v) to 2% (w/v).

The isotonic agent serves to appropriately maintain (control) the osmotic pressure when the composition of the present invention containing phosphatidylcholine is administered into the body, and also has a subsidiary effect of further stabilizing the phosphatidylcholine in the solution. The isotonic agent may be a pharmaceutically acceptable sugar, salt, or any combination or mixture thereof. Examples thereof include glucose as a sugar, and sodium chloride, calcium chloride, sodium sulfate, glycerin, propylene glycol, polyethylene glycol of molecular weight of 1000 or less, and the like as a water-soluble inorganic salt. And more preferably it may be sodium chloride. They may be used singly or in combination of two or more. The concentration of the isotonic agent is preferably 0.1% (w/v) to 5% (w/v), and may be adjusted to an appropriate amount such that the solution formulation containing each of the respective mixtures become an isotonic solution depending on the type, amount, and the like of the components contained in the composition of the present invention.

The pH adjuster of the present invention plays a role of controlling the pH of the injectable preparation and includes both acidic and basic substances. The acidic substance includes, but is not limited to, hydrochloric acid, acetic acid, adipic acid, ascorbic acid, sodium ascorbate, sodium ethoxide, malic acid, succinic acid, tartaric acid, fumaric acid and citric acid. The basic substance includes, but is not limited to, an inorganic base (for example, sodium hydroxide, potassium hydroxide, sodium carbonate, sodium hydrogen carbonate, magnesium carbonate, calcium carbonate, magnesium oxide, ammonia, synthetic hydrotalcite), an organic base (for example, basic amino acid such as lysine, arginine, etc, meglumine, etc.), and the like. In the present invention, the pH adjuster may include an acidic substance and a basic substance, respectively, in the composition alone, or two or more of the substances may be used in combination. More preferably, the pH adjuster of the present invention may be sodium hydroxide and/or hydrochloric acid. The amount of the pH adjuster to be added may vary depending on the kind and amount of the constituents of the composition of the present invention, and is preferably 0.01% (w/v) to 1.32% (w/v), more preferably 0.01% (w/v) to 1% (w/v). The composition of the present invention may preferably be provided in the range of pH 7.0 to pH 7.8, and the kind and amount of the pH adjuster may be changed according to the specific composition of the solution by one of ordinary skill in the art.

As the most preferred form, the present invention provides a composition for reducing localized fat with a reduced pain and side effect, the composition consisting of:

(i) phosphatidylcholine;
(ii) at least one selected from the group consisting of glycocholic acid (GCA) or taurocholic acid (TCA) and salts thereof;
(iii) a preservative;
(Iv) an isotonic agent;
(V) a pH adjuster; and
(Vi) the remaining water, wherein a molar ratio of (ii) to (i) in the composition is in a range of 0.7 to 3.0. The individual component characteristics, contents, combinations and the like of the composition can be understood with reference to the above description.

The present invention also provides a preparation for removing localized fat deposition with a reduced pain and side effect in a subject, the preparation comprising:

(i) phosphatidyl choline; and
(ii) at least one selected from the group consisting of glycocholic acid (GCA), taurocholic acid (TCA) and salt thereof, wherein a molar ratio of (ii) to (i) in the preparation is in a range of 0.7 to 3.0.

The present invention also provides a preparation for removing localized fat deposition with a reduced pain and side effect in a subject, the preparation consisting of:

(i) phosphatidyl choline; and
(ii) at least one selected from the group consisting of glycocholic acid (GCA), taurocholic acid (TCA) and salt thereof, wherein a molar ratio of (ii) to (i) in the preparation is in a range of 0.7 to 3.0.

The present invention also provides a preparation for removing localized fat deposition with a reduced pain and side effect in a subject, the preparation essentially consisting of:

(i) phosphatidyl choline;
(ii) at least one selected from the group consisting of glycocholic acid (GCA), taurocholic acid (TCA) and salt thereof; and
(iii) water (or water for injection), wherein a molar ratio of (ii) to (i) in the preparation is in a range of 0.7 to 3.0.

As the most preferred form, the present invention provides a preparation for removing localized fat with a reduced pain and side effect, the preparation consisting of:

(i) phosphatidylcholine;
(ii) at least one selected from the group consisting of glycocholic acid (GCA) or taurocholic acid (TCA) and salts thereof;
(iii) a preservative;
(Iv) an isotonic agent;
(V) a pH adjuster; and
(Vi) the remaining water, wherein a molar ratio of (ii) to (i) in the composition is in a range of 0.7 to 3.0. The composition, content and characteristics of the specific substances constituting the preparation are the same as those for the composition for reducing localized fat.

The composition for reducing localized fat of the present invention and the preparation of the present invention may be characterized by being composed of pH 6.8 to pH 7.8.

The unit dose (unit dosage) of the composition or preparation of the present invention may be the total amount of, for example, 500 ml, 400 ml, 300 ml, 200 ml, 100 ml, 90 ml, 80 ml, 70 ml, 60 ml, 50 ml, 40 ml, 30 ml, 20 ml, 10 ml, 9 ml, 8 ml, 7 ml, 6, ml, 5 ml, 4 ml, 3 ml, 2 ml, 1 ml, 0.9 ml, 0.8 ml, 0.7 ml, 0.6 ml, 0.5 ml, 0.4 ml, 0.3 ml, 0.2 ml, 0.1 ml, 0.09 ml, 0.08 ml, 0.07 ml, 0.06 ml, 0.05 ml, 0.04 ml, 0.03 ml, 0.02 ml, 0.01 ml, 0.009 ml, 0.008 ml, 0.007 ml, 0.006 ml, 0.005 ml, 0.004 ml, 0.003 ml, 0.002 ml, 0.001 ml, 0.0009 ml, 0.0008 ml, 0.0007 ml, 0.0006 ml, 0.0005 ml, 0.0004 ml, 0.0003 ml, 0.0002 ml or 0.0001 ml to the affected area of mammals, but not limited thereto. The unit dose will depend in part on the target area, the amount of fat and the desired result.

Specifically, the unit dose (unit dosage) of the composition or preparation of the present invention may be administered in the range of 0.1 ml to 500 ml, preferably 1 ml to 200 ml, more preferably 1 ml to 100 ml, of the total amount to the affected area.

The composition or preparation of the present invention may be administered by administering to multiple target sites (point) at regular intervals in the affected area with a single administration, and the total amount may refer to the total amount of the dose administered through these multiple target sites at the single administration. The target site may be set in a range of 1 to 50, preferably 2 to 30, more preferably 3 to 15, etc., for one affected area. In addition, the composition or preparation of the present invention comprises administration to one target site on one affected area at the single administration, and in this case it can be well understood by the one skilled in the art that the total amount is calculated on the basis of the amount for the one target site.

Also, the composition or preparation of the present invention may be administered at a dosage range of, but not limited to, 0.01-20 ml per target site, preferably 0.1-10 ml, more preferably 0.02-5 ml, the most preferably 0.1-1 ml.

The composition or preparation of the present invention may be administered once or multiply to the target site. In certain embodiments, a composition of the invention is administered to the target site at least 1, 2, 3, 4, 5, 6, 7, 8, 9 or 10 times. One or more administration may occur in a single hour, day, week, month, or year. Preferably, multiple administrations to a single target site are administered at 10, 9, 8, 7, 6, 5, 4, 3 or 2 or less times per year, 10, 9, 8, 7, 6, 5, 4, 3 or 2 or less times per month, 10, 9, 8, 7, 6, 5, 4, 3 or 2 or less times per week, 10, 9, 8, 7, 6, 5, 4, 3 or 2 or less times per day, 10, 9, 8, 7, 6, 5, 4, 3 or 2 or less times per hour. In certain embodiments, the subject is provided with 1-100, 2-50, 3-30, 4-20, or 5-10 administrations at the target site. Such administrations may occur over a period of 1 year, 6 months, 5 months, 4 months, 3 months, 2 months, 1 month, 3 weeks, 2 weeks or 1 week or less.

The composition or preparation of the present invention may be administered at various levels (depth) below the skin, including, but not limited to, for example, 0.1-4 inches, 0.5-3 inches, 1-2 inches below the skin.

The present invention also provides a kit comprising:

(I) a first container comprising a composition or preparation for removing localized fat deposition with a reduced pain and side effect, the composition or preparation comprising: (i) phosphatidyl choline; and (ii) at least one selected from the group consisting of glycocholic acid (GCA), taurocholic acid (TCA) and salt thereof, wherein a molar ratio of (ii) to (i) in the composition or preparation is in a range of 0.7 to 3.0; and (II) a delivery device capable of delivering the composition or preparation to a site of fat deposition.

As the more preferable embodiment, the present invention provides a kit comprising:

(I) a first container comprising a composition or preparation for removing localized fat deposition with a reduced pain and side effect, the composition or preparation comprising: (i) phosphatidyl choline; and (ii) at least one selected from the group consisting of glycocholic acid (GCA), taurocholic acid (TCA) and salt thereof, wherein the at least one selected from the group consisting of glycocholic acid (GCA), taurocholic acid (TCA) and salt thereof is contained at the same weight as the phosphatidyl choline or less; and (II) a delivery device capable of delivering the composition or preparation to a site of fat deposition.

In the kit of the present invention, (I) the composition or preparation contained in the first container is understood with reference to the description of the composition and preparation for reducing localized fat of the present invention described above. The first container has a volume sufficient to accommodate the unit dose (dosage volume) of the composition or preparation of the present invention. For example, the first container may be appropriate to accommodate 500 ml, 100 ml, 20 ml, 10 ml, 5 ml, 4 ml, 3 ml, 2 ml, or 1 ml solutions. In some embodiments, the first container may has the volume of 0.01 ml to about 100 ml, from about 0.1 ml to about 90 ml, from about 0.5 ml to about 80 ml, from about 1 ml to about 70 ml, from about 2 ml to about 60 ml, from about 3 ml to about 50 ml, from about 4 ml to about 40 ml, from about 5 ml to about 30 ml, from about 6 ml to about 20 ml, and from about 7 ml to about 10 ml. In a more preferred embodiment, the first container is a vial or ampoule having a volume capacity of about 1-10 ml.

The kit of the present invention comprises (II) a delivery device for delivering the composition in the first container to the fat deposition site. The specific type of the delivery device is not particularly limited, but may be preferably a syringe, and/or may further include another suitable delivery device (e.g., a patch).

The delivery device may have previously loaded the unit dose of the composition or preparation of the present invention.

The kit of the present invention may optionally further comprise a plurality of containers. For example, the kit may further comprise an appropriate amount of diluent for dilution of the composition or formulation contained in the first container and/or a second container comprising any other second agent. The any other second agent can be selected as a constituent component according to the purpose of the kit by a person skilled in the art, and the kind thereof is not particularly limited, and examples thereof include antimicrobial agents, vasoconstrictors, anti-thrombotic agents, anti-coagulation agent, dispersants, anti-dispersants, penetration enhancers, steroids, tranquilizers, muscle relaxants and antidiarrhotica.

The kit may include a written description for using the composition or preparation for reducing localized fat with a reduced pain and side effect. Accordingly, the composition or preparation contained in the first container (I) may be administered according to the written description. The written description may provide instructions for taking, which may depend on, for example, the target site, the mammal to be treated, the desired result, the location of the target site, the concentration of the solution, and the amount of fat deposition. Preferably, the written descriptions are for the treatment of mammals such as humans, dogs, cats or horses. The written description may also include information for the treatment of other domesticated animals and/or farm animals.

The written description can include information on the use of the compositions of the present invention to treat certain target areas, such as under the eyes of a mammal, submental, under the arm, hips, calves, back, thighs, ankles or abdomen. In certain embodiments, the written description is specifying instructions for use of the compositions of the present invention for treating fat deposition associated with eyelid fat escape, lipomas, lipodystrophy, buffalo hump fat dystrophy or cellulite.

The written description may include information on the amount of dilution, if necessary, of the components of the first container and/or the diluent of the second container. The written description may provide information regarding the proper administration of the composition or preparation of the present invention, such as frequency or dose of administration.

The term "comprising" is used synonymously with "containing" or "being characterized", and does not exclude additional ingredients or steps that are not mentioned in the compositions and the methods. The term "consisting of" excludes additional elements, steps, or ingredients that are not separately described. The term "essentially consisting of" means that in the scope of the compositions or methods, the term includes described materials or steps as well as any material or step that does not substantially affect basic characteristics of the compositions or methods.

The present invention provides a method for preparing an injectable composition for reducing localized fat with a reduced pain and side effect, the method comprising the steps of:

(a) adding at least one selected from the group consisting of glycocholic acid (GCA), taurocholic acid (TCA) and salt thereof to water for injection, followed by dissolving while stirring to obtain a clear mixture;

(b) adding a preservative, followed by stirring;

(c) adding phosphatidyl choline, followed by stirring at room temperature; and (d) adjusting a total volume of the composition with water, followed by stirring, wherein a molar ratio of the at least one selected from the group consisting of glycocholic acid (GCA), taurocholic acid (TCA) and salt thereof to the phosphatidyl choline is in a range of 0.7 to 3.0.

Hereinafter, the method for preparing an injectable composition for reducing localized fat of the present invention will be described step by step.

In the step (a), at least one selected from the group consisting of glycocholic acid (GCA), taurocholic acid (TCA) and salt thereof is added to water for injection, followed by dissolving while stirring to obtain a substantially clear mixture.

At this point, the at least one (substance) selected from the group consisting of glycocholic acid, taurocholic acid, and salts thereof, and their combination and mixing ratio are as described above in the composition. In the step (a), a pH adjuster may be optionally pre-added.

The step (b) is a step of administering a preservative. In the step (b), any one of isotonic agent and pH adjuster, or both of them may be further added and stirred. The components and concentrations of the preservatives, isotonic agents and pH adjuster are the same as described above in the description of the composition.

In the present invention, stirring or mixing may be performed by a known stirring means (stirrer), and a person skilled in the art may vary the conditions such as temperature, pressure, time or rotation speed depending on the kind or characteristics of the material to be introduced in order to improve efficiency.

In the step (c), phosphatidylcholine is added to the mixture stirred in step (b), and the mixture is stirred until the mixture is solubilized under the condition of shade and airtightness. The stirring may be carried out by stirring means (stirrer) known in the art, preferably carried out for 2 to 24 hours, more preferably for 5 to 15 hours. The rotation speed is not limited to this, but can be performed at 100 to 1000 rpm. Through the above process, phosphatidylcholine can be produced as homogeneous particles having a small particle size (particle diameter of 2 to 10 nm, preferably particle diameter of 2 to 6 nm) in the composition. If the stirring process is performed for less than 2 hours, desired particle size and homogeneity can not be obtained, and if it exceeds 24 hours, it is uneconomical for the production process. Those skilled in the art will also be able to set various process conditions to increase the solubility of the component material, for example, to stir the component material under conditions such as nitrogen pressure.

In the step (d), the total volume is adjusted with water and mixed homogeneously. The water can be replaced with water for injection, which is the same as described above. In the step (d), the addition of the pH adjuster may be performed. In this step, in order to secure the product stability according to the distribution of the injection preparation, pH can be adjusted by using an acid solution or a buffer (pH adjuster) such as phosphate which can be used as an injection, and physically or chemically stable injection preparation can be prepared. The kind or amount of the pH adjuster which can be used in the present invention are as described above.

Also, the method may further include (e) filtering the solution stirred in the step (d) to obtain a filtrate having a particle diameter of 2 to 10 nm of phosphatidylcholine.

The step (e) is a step of separating the molecules of phosphatidylcholine having a particle diameter of 2 to 10 nm at a high concentration through filtration. The filtration may be performed using conventional filtration means known in the art, and the filtration may be performed by, for example, a syringe filter. The particle diameter may preferably be between 2 and 5 nm.

As the preferable embodiment, the present invention provides a method for preparing a pharmaceutical composition for non-surgically removing localized fat deposition with a reduced pain and side effect, the method comprising adding phosphatidyl choline, and at least one selected from the group consisting of glycocholic acid, taurocholic acid and salt thereof, wherein the at least one selected from the group consisting of glycocholic acid, taurocholic acid and salt thereof is added at the same weight as the phosphatidyl choline or less. With respect to these specific examples, the specific material composition, mixing ratio, and the like are understood with reference to the description of the composition and preparation of the present invention described above.

The present invention also provides a method for removing localized fat deposition with a reduced pain and side effect in a subject, the method comprising administering an effective amount of phosphatidyl choline; and at least one solubilizing agent of phosphatidyl choline selected from the group consisting of glycocholic acid, taurocholic acid and salt thereof to the subject having localized fat deposition.

That is, in the above method, the phosphatidylcholine is contained at a concentration of 0.625 to 15% (w/v) based on the total composition in a pharmaceutically acceptable injectable solution (composition) for the administration of phosphatidylcholine, and preferably at a concentration of 1.25 to 12.5% (w/v), and more preferably at a concentration of 2.5 to 10.0% (w/v) in the composition. In this case, the unit dose of the composition for phosphatidylcholine administration can be 500 ml, 400 ml, 300 ml, 200 ml, 100 ml, 90 ml, 80 ml, 70 ml, 60 ml, 50 ml, 40 ml, 30 ml, 20 ml, 10 ml, 9 ml, 8 ml, 7 ml, 6, ml, 5 ml, 4 ml, 3 ml, 2 ml, 1 ml, 0.9 ml, 0.8 ml, 0.7 ml, 0.6 ml, 0.5 ml, 0.4 ml, 0.3 ml, 0.2 ml, 0.1 ml, 0.09 ml, 0.08 ml, 0.07 ml, 0.06 ml, 0.05 ml, 0.04 ml, 0.03 ml, 0.02 ml, 0.01 ml, 0.009 ml, 0.008 ml, 0.007 ml, 0.006 ml, 0.005 ml, 0.004 ml, 0.003 ml, 0.002 ml, 0.001 ml, 0.0009 ml, 0.0008 ml, 0.0007 ml, 0.0006 ml, 0.0005 ml, 0.0004 ml, 0.0003 ml, 0.0002 ml or 0.0001 ml or less. Specifically, the unit dose (unit dosage) of the composition for administering phosphatidylcholine to affected area may be 0.1 ml to 500 ml, preferably 1 ml to 200 ml, and more preferably 1 ml to 100 ml of the total volume.

In the above method, the solubilizing agent of phosphatidylcholine and phosphatidylcholine may be administered at a molar ratio (solubilizing agent/phosphatidylcholine) of 0.7 to 3.0, more preferably 0.7 to 2.60, the most preferably 0.7 to 1.73.

The phosphatidylcholine and solubilizing agent of phosphatidylcholine may be administered simultaneously or sequentially. For example, when each component contained in the pharmaceutical composition of the present invention is a single composition, it may be administered simultaneously. If the composition is not a single composition, one component may be administered before or after the administration of the other component within a few minutes. Preferably, the solubilizing agent of phosphatidylcholine and phosphatidylcholine may be administered simultaneously. Whether or not each component is administered simultaneously or sequentially, it is preferred that each of these components is contained in a pharmaceutically acceptable injectable solution (composition), and composition comprising each component is not necessarily follow the composition of the present invention described above, and a method in which the result of administration to a subject satisfies the molar ratio of each component can be employed.

In the method, at least one selected from the group consisting of the isotonic agent and pH adjuster may be administered simultaneously or sequentially with the phosphatidylcholine and/or the solubilizing agent of phosphatidylcholine. The specific concentrations of these components and the like can be understood with reference to the above description in this specification.

The administration may preferably be a direct injection into a site where localized fat deposition (accumulation) has occurred, and the injection preferably includes subcutaneous injection, intradermal injection and the like.

The subject is preferably a mammal. Such mammals include humans or primates (e.g., monkeys, chimpanzees, etc.), domesticated animals (e.g., dogs, cats, horses, etc.), farm animals (e.g., goats, sheep, pigs, cows, etc.) or laboratory animals (e.g., mice, rats, etc.). The subject may also be an animal-derived cell, tissue, organ, or the like. Preferably, it may be human being in need of removal of localized fat deposition (accumulation) and the removal includes both cosmetic and therapeutic purposes. As such an example, it may be a patient in need of treatment for a pathological condition (disease) due to abnormal localized fat deposition.

For example, the compositions of the present invention may be used to treat certain fat conditions in a patient, including Lipoma, prolapse, atherosclerosis, madelung throat, lip edema, phyozoospermia nodule, yellow cardioma, fatty dystrophy and cellulite. In certain embodiments, the compositions of the present invention can be used to treat fat conditions at sites such as localized fat deposition below the eyes, chin, arms, hips, calves, back, thighs, ankles or abdomen of a mammal.

The term "treatment" as used herein is a concept involving inhibiting, eliminating, alleviating, ameliorating, and/or preventing a disease, or symptom or condition due to the disease.

The present invention also relates to a method for reducing fat (especially subcutaneous fat) deposition in mammals, wherein the present invention is preferably used for non-surgical removal of localized fat deposition in a subject. As a specific example, the non-surgical method of the present invention does not comprise liposuction, lipo-plastic operation or inhaled subcutaneous lipectomy.

The method of the present invention is characterized in that the pain and side effects are alleviated (substantially reduced to a level of None), and a detailed description of the pain and side effects can be understood with reference to the above description.

Preferably, the present invention provides a method for non-surgically removing localized fat deposition with a reduced pain and side effect in a subject having localized fat deposition, the method comprising administering a preparation comprising (i) phosphatidyl choline; and (ii) at least one selected from the group consisting of glycocholic acid, taurocholic acid and salt thereof. The preparation or composition contained in the preparation used in the present method may be a single composition or a preparation following the composition of the present invention described above. As other examples, the preparation or composition contained in the preparation is not necessarily follow the composition of the present invention described above, and a method in which the result of administration to a subject satisfies the molar ratio of (ii) to (i) of 0.7 to 3.0, preferably 0.7 to 2.60, the most preferably 0.7 to 1.73 can be employed.

As the preferable example, the present invention provides a method for non-surgically removing localized fat deposition with a reduced pain and side effect in a subject, the method comprising administering a preparation comprising (i) phosphatidyl choline; and (ii) at least one selected from the group consisting of glycocholic acid, taurocholic acid and salt thereof to the subject having localized fat deposition, wherein a molar ratio of (ii) to (i) in the composition is in a range of 0.7 to 3.0.

In the above method, the preparation is understood in terms of composition, content and characteristics, etc. with reference to the above description in the specification of the present invention, and the method for removing localized fat deposition of the present invention comprises or consists of topically administering a unit dose (total amount) of one or more of the compositions or preparations described above in the specification of the present invention to a fat deposition site (affected area) of the subject (mammals). With respect to the composition, the preparation and the unit dose thereof, the above-mentioned description will be referred to.

The method of the present invention relates to a method for reducing subcutaneous fat deposition. Such methods may comprise or consist of locally administering a dosage unit of one or more compositions or preparation of the present invention to a fat deposition site in a mammal.

The preparation is administered to a subject in need thereof in an effective amount, the 'effective amount' refers to the amount showing an effect of localized fat reduction (including improvement, treatment, prevention effect on fat deposition disease). In general, the total amount administered, the unit dose, and the number of treatments will vary depending on the amount of fat in the target site, the location of the target site, the form of fat composition, and the desired outcome. Generally, the greater the amount of fat to be treated, the greater the amount administered. Since the amount of the composition of the present invention that constitutes "therapeutically effective amount" will vary depending on the disease state and its severity, the age of the patient to be treated, etc., the therapeutically effective amount is not limited to the amount described herein, and may be routinely determined by one of ordinary skill in the art.

The above administration method is understood with reference to the above description, and as a preferable example, it can be administered percutaneously or subcutaneously through a subcutaneous injection using a syringe at a target site. The target site may be, for example, 0.1 cm×0.1 cm to about 5 cm×5 cm. The compositions of the present invention may be administered to the same target site, adjacent to or near the site, at various intervals, doses, and quantities described herein.

Advantageous Effects

The injectable composition for reducing localized fat deposition of the present invention comprising taurocholic acid or glycocholic acid (or a salt thereof) and phosphatidylcholine (PPC) in a specific mixing ratio has stable and safe formulation, and has a great effect of adipocyte-specific lipolysis and adipocyte-specific apoptosis without a adipocyte necrosis which is caused by conventional PPC preparation comprising DCA (such as Lipostabil®) and the preparation comprising DCA alone (such as Kybella). Therefore, the effect of reducing adipocyte without side effects, such as pain, edema, paresthesia, extensive swelling, erythema, induration, paresthesia, nodule, pruritus, burning sensation, and necrosis of muscle cells, fibroblasts and vascular endothelial cells other than adipocytes, is excellent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the images of the composition, wherein the images were obtained immediately after adding only 5% (w/v) of PPC to the water for injection followed by stirring for 72 hours with a stirrer, and obtained 1 day after the final stirring. FIG. 1B shows the images of composition, wherein the images were obtained immediately after adding various concentration (0.625% (w/v), 1.25% (w/v), 2.5% (w/v), 5.0% (w/v), 7.5% (w/v), 10.0% (w/v) from the left) of PPC to water for injection followed by stirring for 1 hour and dispersing at high pressure homogenizer, and obtained at 7 days and 30 days after the preparation of the composition.

FIG. 2A shows the formulation property by concentration % (w/v) of deoxycholic acid (DCA) based on PPC 5% (w/v).

FIG. 2B shows the formulation property by concentration % (w/v) of glycocholic acid (GCA) based on PPC 5% (w/v).

FIG. 2C shows the formulation property by concentration % (w/v) of taurocholic acid (TCA) based on PPC 5% (w/v).

FIG. 2D shows the formulation property by concentration % (w/v) of cholic acid (CA) based on PPC 5% (w/v).

FIG. 2E shows the formulation property by concentration % (w/v) of chenodeoxycholic acid (CDCA) based on PPC 5% (w/v).

FIG. 2F shows the formulation property by concentration % (w/v) of ursodeoxycholic acid (UDCA) based on PPC 5% (w/v).

FIG. 2G shows the formulation property by concentration % (w/v) of glycodeoxycholic acid (GDCA) based on PPC 5% (w/v).

FIG. 2H shows the formulation property by concentration % (w/v) of taurodeoxycholic acid (TDCA) based on PPC 5% (w/v).

FIG. 2I shows the formulation property by concentration % (w/v) of hyodeoxycholic acid (HDCA) based on PPC 5% (w/v).

FIG. 2J shows the formulation property by concentration % (w/v) of tauroursodeoxycholic acid (TUDCA) based on PPC 5% (w/v).

FIG. 3A shows an image of PPC complex composition solubilized with lithocholic acid (LCA), and it was impossible to prepare mixed micelles. FIG. 3B shows an image of the PPC complex composition solubilized with dehydrocholic acid (DHCA), and it was impossible to prepare stable mixed micelles.

FIG. 4A shows the comparison results of edema after injection of various concentration of PPC single composition (1.25-15.0%) and DCA 1% single composition.

FIG. 4Q shows the comparison results of edema after injection of complex composition of PPC 5.0% solubilized with various concentration of TCA (2.5-25%).

FIGS. 6A to 6F show a series of images of histological test. Rats were sacrificed at 3 hours after injecting 1.0 ml of PPC (1.25-15.0%) single composition and PBS (FIG. 6A), single composition of various kind of bile salts (DCA, HDCA, UDCA, TDCA, GDCA, CDCA, CA, GCA, TCA and TUDCA) at concentrations of 1.0-7.5% (FIGS. 6B and 6C), PPC 5.0% complex compositions solubilized with various kind of bile salts (FIG. 6D), PPC (2.5-15.0%) complex compositions solubilized with GCA (1.25-7.5%) (FIG. 6E) or PPC (5.0%) complex compositions solubilized with GCA (2.5-20.0%)(FIG. 6F). The injected area was cut, fixed with 10% formalin, and then subjected to histological examination using an optical microscope. H & E staining demonstrates inflammation of the treated paws (200× magnification).

FIG. 7E shows a graph demonstrating the viability of adipocyte at 96 hours after the treatment of DCA (1.0%) and PPC (5.0%) as single compositions, and PPC (5.0%)+GCA (2.5%), PPC (5.0~15.0%)+TCA (2.5~7.5%) and PPC (5.0~15.0%)+TUDCA (4.0~12.0%) as complex compositions.

FIGS. 7F to 7H show graphs demonstrating the viability of adipocyte at 96 hours after the treatment of PPC (2.5~10.0%), DCA (1.1~4.4%) and GCA (1.25~5.0%) as single compositions, and PPC (2.5~10.0%)+GCA (1.25~5.0%) and PPC (2.5~10.0%)+DCA (1.1~4.4%) as complex compositions.

FIG. 7I shows a graph demonstrating the viability of adipocyte at 96 hours after the treatment of PPC (5.0%) single composition and PPC (5.0%) complex composition solubilized with various concentration of GCA (2.5-8.75%).

FIGS. 10A and 10B show the result of Caspase 3 activity. 3T3-L1 adipocytes were plated at 1×10$^5$ cells in each well and the preparations containing PPC 5.0%, PPC 5.0%+DCA 2.2%, PPC 5.0%+GCA 2.5%, PPC 5.0%+GCA 5.0%, DCA 1.0% or GCA (1.0-5.0%) and PBS control were incubated for 0-48 hours at 37° C. (repeated 3 times). Then, the result was measured at a wavelength of 405 nm with a spectrophotometer, at after 24 hours (FIG. 10A) and 48 hours (FIG. 10B).

FIGS. 10C and 10D show the result of glycerol release. Treatment of each test material was carried out in the same manner as in FIGS. 10A and 10B. The material-treated adipocytes were cultured at 37° C. for 0-48 hours to induce lipolysis. After incubation at room temperature for 30 minutes, OD570 was measured with a spectrophotometer (repeated 3 times).

FIGS. 11A to 11D show the images demonstrating histological changes observed in the fat pad from the mouse to which the test material was administered. FIG. 11A shows the result of injection of PPC (2.5-15.0%) single composition.

FIG. 11B shows the result of injection of PBS, Isuprel or DCA 1.0% as single compositions, and PPC 5.0%+DCA 2.2%, PPC 5.0%+CDCA 2.5%, PPC 5.0%+HDCA 2.5% or PPC 5.0%+UDCA 3.0% as complex compositions.

FIG. 11C shows the result of injection of PPC 5.0%+GDCA 2.5%, PPC 5.0%+TDCA 2.5%, PPC 5.0%+CA 2.5%, PPC 5.0%+GCA 2.5%, PPC 5.0%+TCA 2.5% or PPC 5.0%+TUDCA 4.0% as complex compositions.

FIG. 11D shows the result of injection of PBS, PPC 5.0% or GCA 2.5% as single compositions, and PPC (2.5~10.0%)+GCA (1.25~5.0%) as complex compositions.

After the injection, the adipose tissue of administered site was incised. The incised tissue was fixed with formaldehyde, impregnated into paraffin blocks, and then fragmented on a slide glass. Tissue necrosis, apoposis, and degradation were observed by H&E staining

FIG. 12A shows the result of low dose administration group (PPC (90 mg/kg)+GCA (50.4 mg/kg) complex composition), FIG. 12B shows the result of medium dose administration group (PPC (180 mg/kg)+GCA (100.8 mg/kg) complex composition), and FIG. 12C shows the results of high dose administration group (PPC (360 mg/kg)+GCA (201.6 mg/kg) complex composition) for beagle females and males.

FIGS. 14A and 14B show the efficacy results of reduction of submental fat in the subject who received PPC complex composition solubilized with the GCA of the present invention. After the topical anesthesia with 9.6% lidocaine ointment at the site of administration (submental), 10 ml of PPC 5.0%+GCA 2.8% complex injectable composition (PPC 500 mg+GCA 280 mg) was injected 6 times at intervals of 4 weeks into the submental fat (total of 50 points, 0.2 cc per point, 1.0 cm interval, a 6-8 mm depth, and using a 30 G 13 mm injection needle). After 12 weeks, the series of images were taken. FIG. 14A is the image taken by a standard clinical photographing method, and FIG. 14B is the series of images showing a reduction in submental fat thickness on CT.

FIGS. 15A to 15C show the result comparing the pain, edema and harmful examples after administering the PPC complex composition solubilized with GCA to 6 subjects who had experienced injection of PPC injectable composition solubilized with DCA. The test materials were 10 ml of solution in which Lipobean i.v. (PPC 50.0 mg+DCNa 24.0 mg in 1 ml) was diluted with injectable 0.9% saline solution at a ratio of 1:1 (that is, PPC 25.0 mg+DCNa 12.0 mg), 10 ml of PPC 5.0% solubilized with GCA 2.8% (PPC 50.0 mg+GCA 28.0 mg in 1 ml) and 10 ml of PPC 5.0% solubilized with GCA 4.0% (PPC 50.0 mg+GCA 40.0 mg in 1 ml). Each test material was injected into the submental fat (total of 50 points, 0.2 cc per point, 1.0 cm interval, a 6-8 mm depth, and a 30 G 13 mm injection needle), and the questionnaires were carried out at the time of 1, 3, 7 and 10 days after administration of each material.

FIG. 15A shows the degree of pain measured with 100 mm pain VAS, FIG. 15B shows the degree of edema according to Edema grade scale (0: no-0 mm, 1: mild-2 mm, 2: moderate-4 mm, 3: severe-6 mm, 4: extremely severe-8 mm)), and FIG. 15C shows the harmful examples including extensive swelling, hematoma, bruising, erythema, nodule and pruritus at the site of administration of 5 grades (0: absent, 1: mild, 2: moderate, 3: severe, 4: extremely severe).

MODE FOR CARRYING OUT THE INVENTION

Figure 1A:
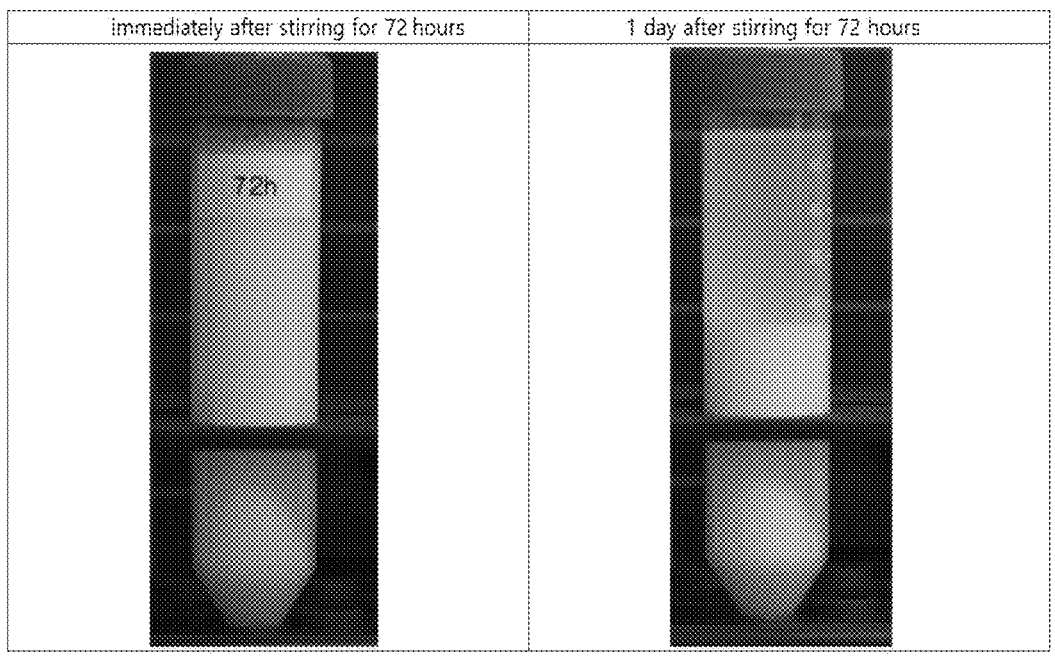
FIGS. 1A and 1B show a series of images in which PPC without addition of a solubilizing agent is dispersed with a stirrer and a high pressure homogenizer.

Hereinafter, the present invention will be described in detail with reference to the following examples. However, the following examples are merely for illustrating the present invention and are not intended to limit the scope of the present invention.

Material

Materials added into the preparation of the injectable compositions of the present invention and comparative compositions are as follows:

Phosphatidylcholine (PPC, S-100, LIPOID GmbH, 784 g/mol based on oleoyl-linoleoyl-glycero-phosphocholine), cholic acid (Glycocholic acid, CA, New Zealand pharm), deoxycholic acid (DCA, Sigma-Aldrich), sodium deoxycholate (DCNa, New Zealand pham), glycocholic acid (GCA, New Zealand pham), sodium glycocholate (GCNa, New Zealand pham), taurocholic acid (TCA, Sigma-Aldrich), sodium taurocholate (TCNa, New Zealand pham), chenodeoxycholic acid (CDCA, Sigma-Aldrich), urosodeoxycholic acid (UDCA, Sigma-Aldrich), glycodeoxycholic acid (GDCA, Sigma-Aldrich), taurodeoxycholic acid (TDCA, Sigma-Aldrich), hiodeoxycholic acid (HDCA, Sigma-Aldrich), lithocholic acid (LCA, Sigma-Aldrich), dihydrocholic acid (DHCA, Sigma-Aldrich), tauroursodeoxycholic acid (TUDCA, Tokyo Chemical Industry), benzyl alcohol- (Sigma-Aldrich, 0.9% w/v), sodium chloride (Sigma-Aldrich, 0.44% w/v), sodium hydroxide (Sigma-Aldrich, 0.04-0.76% w/v), hydrochloric acid (Sigma-Aldrich, 0.001-0.6% w/v) and water for injection. Of the added materials, the isotonic agent (sodium chloride) was used in a manner such that it was added together with benzyl alcohol in the examples and the comparative examples.

transferred to an ultra-high pressure homogenizer (Nano Disperser NLM100, Ilshin Autoclave, Korea) with a nitrogen pressure. Ultra-high pressure homogenization (dispersion) was carried out at 12,000 psi for 7 cycles, and the particles were finely pulverized. Then, the pH was adjusted. After filtration through a 0.2 μm filter, the vial was filled and sealed.

TABLE 1

PPC single injectable preparations dispersed with high pressure homogenizer

| | Comparative Example 1-1 | Comparative Example 1-2 | Comparative Example 1-3 | Comparative Example 1-4 | Comparative Example 1-5 | Comparative Example 1-6 |
|---|---|---|---|---|---|---|
| PPC % (w/v) | 0.625 | 1.25 | 2.5 | 5.0 | 7.5 | 10.0 |
| Property (after preparation) | Slightly cloudy | Slightly cloudy | Slightly cloudy | Cloudy | Cloudy | Cloudy |
| Property (at 30 days after preparation) | Slightly cloudy | Slightly cloudy | Precipitation | Precipitation | Precipitation | Precipitation |
| Transparency (660 nm) | 97.87 | 86.72 | 84.03 | 77.24 | 77.11 | 67.47 |
| Particle size (nm) | 17.16 ± 5.88 | 17.88 ± 5.74 | 18.43 ± 6.16 | 17.07 ± 5.19 | 15.27 ± 4.73 | 16.69 ± 4.51 |

Analysis Devices

The devices used in the analysis of the injectable compositions of the present invention and comparative compositions are as follows.

The particle size was measured using a nano particle size analyzer (Microtrac Wave, MICROTRACT, USA). The layer separation due to precipitation was observed with a camera (Nikkon, D5200, AF-P DX NIKKOR 18-55 mm f/3.5-5.6G VR tense). The transparency was measured using a spectrophotometer (CM-3600d, KONICA MINOLTA, JAPAN). The pH was measured with a pH meter (ST3100, OHAUS, GERMANY), and the isotonicity was measured with an osmotic pressure meter (Vapro 5600, Elitech Group, Tokyo, Japan), and viscosity was analyzed using a viscometer (Digital Viscometer CL-2, CAS, Korea).

The compositions of the present invention (examples) and comparative compositions (comparative examples) as PPC-based preparation for reducing localized fat according to the type of solubilizing agent were prepared as follow. In the following, % of the composition means % (w/v).

Comparative Example 1: PPC Single Injectable Preparations

Phosphatidylcholine single composition without solubilizing agent (PPC concentration 0.313~15.0%) was prepared as follow. Using a high-pressure homogenizer, injectable compositions comprising PPC 3.125 mg (0.3125%), 6.25 mg (0.625%), 12.5 mg (1.25%), 25.0 mg (2.5%), 50.0 mg (5.0%), 75.0 mg (7.5%), 100.0 mg (10.0%), 125.0 mg (12.5%) or 150.0 mg (15.0%), respectively, and benzyl alcohol 9 mg (0.9%) in 1 ml were prepared. And representative results of theses are shown in Table 1 below. Hereinafter, % w/v of the composition is expressed as %.

Figure 1B:
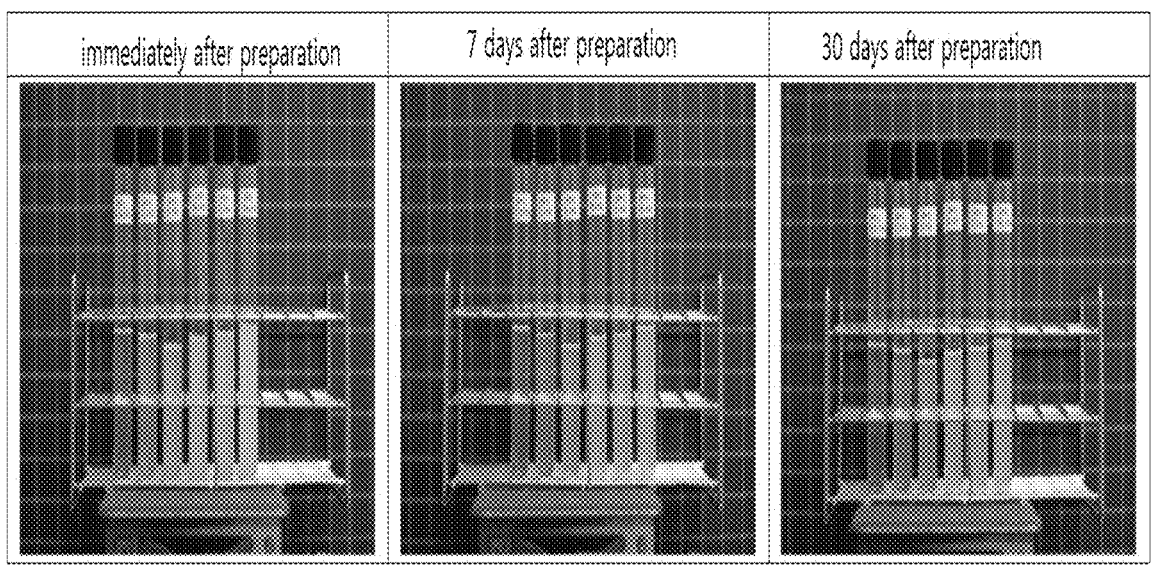

The specific preparing method is as follows. The washed and sterilized preparation tank was charged with the water for injection (at room temperature), and phosphatidylcholine (PPC) and benzyl alcohol were added thereto, and the mixture was stirred at 200 RPM for 2 hours under the condition of nitrogen pressure, shading and room temperature. After the completion of stirring, the mixture was As shown in FIG. 1A, the PPC 5.0% composition without the solubilizing agent had a cloudy appearance immediately after stirring for 24 to 72 hours. At 1 day after the final stirring, the composition had poor formulation stability due to the PPC not being dispersed in the water for injection, and industrial use was limited. Also, as shown in FIG. 1B and Table 1, the description of the composition in which 0.625 to 10.0% of PPC was dispersed with a high-pressure homogenizer without addition of a solubilizing agent exhibited slight cloudy or cloudy depending on the concentration, and the particle size was liposome system of 17.16±5.88 to 16.69±4.51 nm, and unstably dispersed. As a result of observing the properties at 30 days after preparation, it was confirmed that the PPC was precipitated and not dispersed in the water for injection at a concentration of 2.5% or more and was not suitable as an industrial injectable preparation due to low formulation stability (FIG. 1B)

In order to obtain an injectable composition of a clear solution of a micelle structure in which PPC was stably dispersed at a particle size of 10 nm or less, a PPC complex composition prepared by solubilizing with various bile acids (BA) such as DCA, CA, GCA, TCA, CDCA, UDCA, GDCA, TDCA, HDCA, LCA, DHCA and TUDCA at various concentrations was prepared. And, the compositions thereof are shown in detail in the following comparative Examples and Examples.

Comparative Example 2: PPC Injectable Preparations Solubilized with DCA

As shown in Table 2 below, compositions based on phosphatidylcholine (PPC 5.0%) solubilized with deoxycholic acid (DCA), the same as the composition of the previously known Lipostabil® formulation and the like, was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%) or 30.0 mg (3.0%) of DCA respectively, and adding 9 mg of benzyl alcohol (0.9%) in 1 ml. Specifically, the water for injection was put into the preparation tank which was cleaned and sterilized (room temperature), and sodium hydroxide was added to the water for injection. Then deoxycholic acid and benzyl alcohol were added, stirred and dissolved. Then, phosphatidylcholine was added thereto, and the mixture was stirred at 200 RPM for about 24 hours under shading, sealing, room temperature (25° C.), and nitrogen pressure. After completion of the stirring, the pH was adjusted (if necessary, with additional sodium hydroxide or hydrochloric acid), and it was filtered through a 0.2 μm filter, and filled into the vial and sealed. Table 2 shows the properties of PPC injectable preparation solubilized with various concentrations of DCA.

TABLE 2

PPC injectable preparation solubilized with DCA

|  | Comparative Example 2-1 | Comparative Example 2-2 | Comparative Example 2-3 | Comparative Example 2-4 | Comparative Example 2-5 | Comparative Example 2-6 | Comparative Example 2-7 | Comparative Example 2-8 | Comparative Example 2-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| DCA % (w/v) | 1.0 | 1.5 | 2.0 | 2.1 | 2.2 | 2.3 | 2.4 | 2.5 | 3.0 |
| DCA/PPC molar ratio | 0.41 | 0.62 | 0.83 | 0.87 | 0.91 | 0.95 | 0.99 | 1.03 | 1.24 |
| Property (after preparation) | Very cloudy | Very cloudy | Slightly cloudy | Transparent | Transparent | Transparent | Transparent | Transparent | Transparent |
| Property (at 30 days after preparation) | Precipitation | Precipitation | Transparent | Transparent | Transparent | Transparent | Transparent | Transparent | Transparent |
| Transparency (660 nm) | 23.7 | 26.92 | 91.7 | 99.41 | 99.52 | 99.26 | 99.71 | 99.57 | 99.89 |
| Particle size (nm) | 50.80 ± 330.0 | 72.70 ± 492.0 | 39.60 ± 26.14 | 8.57 ± 0.660 | 3.21 ± 0.920 | 3.23 ± 0.780 | 3.20 ± 0.690 | 3.19 ± 0.820 | 2.68 ± 0.850 |

Figure 2A:
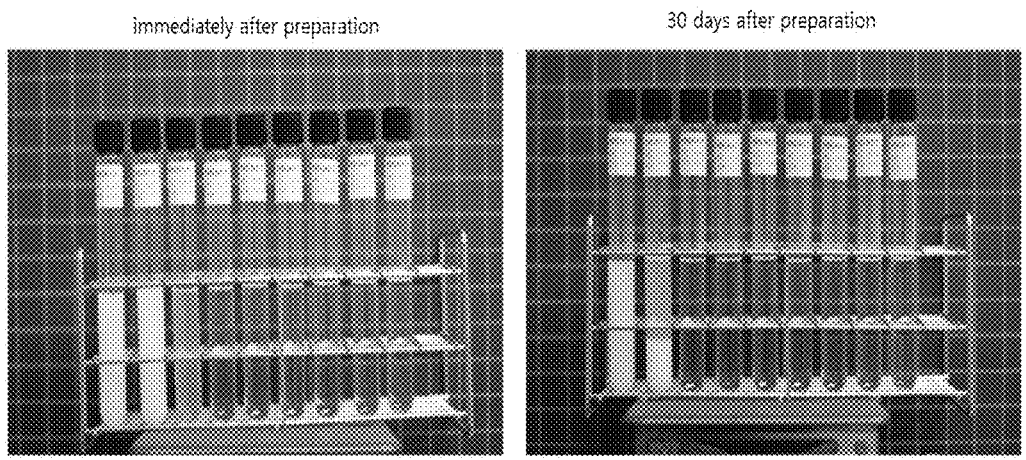
FIGS. 2A to 2J show a series of images of the PPC 5.0% composition solubilized with various concentration of DCA, GCA, TCA, CA, CDCA, UDCA, GDCA, TDCA, HDCA and TUDCA
showing the formulation stability, wherein the images were obtained immediately after and at 30 days after the preparation of the composition.

The formulation stability of PPC injectable preparation solubilized with deoxycholic acid (DCA) was evaluated immediately after the preparation and 30 days after the preparation (after standing at room temperature), and the evaluation results are shown in FIG. 2A. A stable pharmaceutical formulation was observed when DCA was added at 2.1% or more for PPC 5%, and the composition showed transparent (clear) solution properties (Comparative Examples 2-4 to 2-9). In Comparative Examples 2-1 to 2-3, an unstable formulation was observed due to the precipitation phenomenon. Based on the above comparison, it was concluded that stable injectable preparation can be prepared at 2.1% or more of DCA based on PPC 5%. Particularly, in comparative Examples 2-1 to 2-3, the phosphatidylcholine particle size was 50.80±330.0 nm to 39.60±26.14 nm, and it was formed as an unstable emulsion or liposome structure that is not a micelle structure. In comparative Examples 2-4 to 2-9, micelle structures of 10 nm or less were formed. As described above, a composition having a molar ratio of DCA to PPC (DCA/PPC) of less than 0.87 was considered to be inadequate for injectable preparation because a substantially stable formulation did not occur.

Example 1: Preparing PPC Injectable Preparations Solubilized with GCA

As shown in Table 3 and 4 below, compositions based on phosphatidylcholine (PPC) solubilized with glycocholic acid (GCA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%), 26.0 mg (2.6%), 27.0 mg (2.7%), 28.0 mg (2.8%), 29.0 mg (2.9%), 30.0 mg (3.0%), 35.0 mg (3.5%), 40.0 mg (4.0%) or 45.0 mg (4.5%) of GCA respectively, and adding 9 mg of benzyl alcohol (0.9%) in 1 ml. Specifically, the water for injection was put into the preparation tank which was cleaned and sterilized (room temperature), and sodium hydroxide (0.04-0.72%) was added to the water for injection. Then glycocholic acid and benzyl alcohol were added, stirred and dissolved. Then, phosphatidylcholine was added thereto, and the mixture was stirred at 200 RPM for about 24 hours under shading, sealing, room temperature (25° C.), and nitrogen pressure. After completion of the stirring, the pH was adjusted (if necessary, with additional sodium hydroxide or 0.001-0.6% of hydrochloric acid), and it was filtered through a 0.2 μm filter, and filled into the vial and sealed. Table 3 and 4 show the properties of PPC injectable preparation solubilized with various concentrations of GCA.

TABLE. 3

|  | Comparative Example 1-1 | Comparative Example 1-2 | Comparative Example 1-3 | Comparative Example 1-4 | Example 1-1 | Example 1-2 | Example 1-3 | Example 1-4 |
|---|---|---|---|---|---|---|---|---|
| PPC % (w/v) | 5.0 | 5.0 | 5.0 | 5.0 | 5.0 | 5.0 | 5.0 | 5.0 |
| GCA % (w/v) | 1.0 | 1.5 | 2.0 | 2.1 | 2.2 | 2.3 | 2.4 | 2.5 |
| GCA/PPC Molar ratio | 0.35 | 0.52 | 0.69 | 0.73 | 0.76 | 0.80 | 0.83 | 0.87 |

TABLE 3-continued

|  | Comparative Example 1-1 | Comparative Example 1-2 | Comparative Example 1-3 | Comparative Example 1-4 | Example 1-1 | Example 1-2 | Example 1-3 | Example 1-4 |
|---|---|---|---|---|---|---|---|---|
| Property (after preparation) | Very cloudy | Very cloudy | Very cloudy | Slightly cloudy | Slightly cloudy | Slightly cloudy | Slightly cloudy | Transparent |
| Property (at 30 days after preparation) | Precipitation | Precipitation | Precipitation | Slightly transparent | Transparent | Transparent | Transparent | Transparent |
| Transparency (660 nm) | 21.03 | 24.18 | 30.05 | 35.24 | 88.0 | 88.05 | 87.78 | 99.79 |
| Particle size (nm) | 198.2 ± 721.0 | 117.5 ± 2.533 | 194.9 ± 2752 | 28.2 ± 11.35 | 9.84 ± 1.780 | 8.41 ± 1.210 | 7.01 ± 1.200 | 7.13 ± 0.880 |
| pH | 7.18 | 7.24 | 7.27 | 7.18 | 7.22 | 7.20 | 7.24 | 7.23 |

TABLE 4

|  | Example 1-5 | Example 1-6 | Example 1-7 | Example 1-8 | Example 1-9 | Example 1-10 | Example 1-11 | Example 1-12 |
|---|---|---|---|---|---|---|---|---|
| PPC % (w/v) | 5.0 | 5.0 | 5.0 | 5.0 | 5.0 | 5.0 | 5.0 | 5.0 |
| GCA % (w/v) | 2.6 | 2.7 | 2.8 | 2.9 | 3.0 | 3.5 | 4.0 | 4.5 |
| GCA/PPC molar ratio | 0.90 | 0.94 | 0.97 | 1.01 | 1.04 | 1.21 | 1.39 | 1.56 |
| Property (after preparation) | Transparent | Transparent | Transparent | Transparent | Transparent | Transparent | Transparent | Transparent |
| Property (at 30 days after preparation) | Transparent | Transparent | Transparent | Transparent | Transparent | Transparent | Transparent | Transparent |
| Transparency (660 nm) | 99.82 | 99.8 | 99.71 | 99.83 | 99.9 | 99.73 | 99.74 | 99.87 |
| Particle size (nm) | 7.43 ± 1.190 | 6.07 ± 0.870 | 3.93 ± 0.750 | 4.00 ± 0.760 | 3.64 ± 0.730 | 2.89 ± 0.830 | 2.38 ± 0.760 | 2.28 ± 0.670 |
| pH | 7.20 | 7.22 | 7.28 | 7.22 | 7.26 | 7.24 | 7.19 | 7.26 |

Figure 2B:
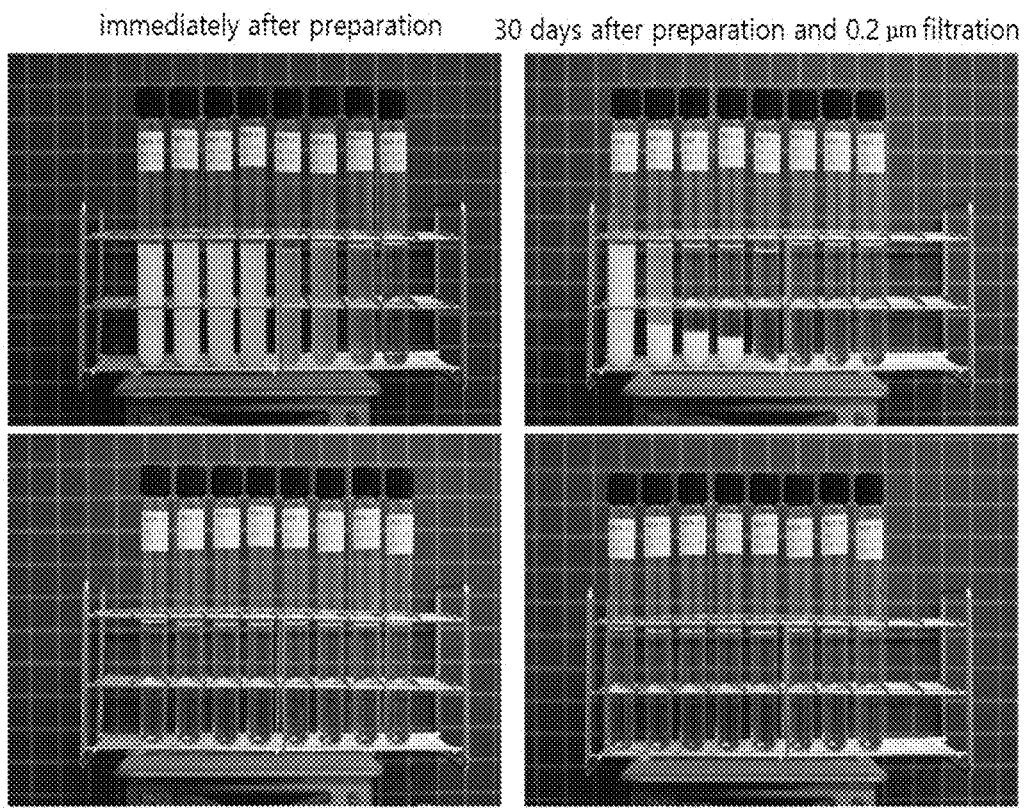

The formulation stability of the PPC injectable compositions solubilized with glycocholic acid (GCA) in Tables 3 and 4 was evaluated immediately after the preparation and 30 days after the preparation (refrigerated storage). The evaluation results are shown in FIG. 2B. When GCA was added at 2.2% or more for PPC 5.0%, it was confirmed that the formulation was stable, and the composition showed transparent (clear) solution properties (Examples 1-1 to 1-12). In Comparative Examples 1-1 to 1-4, it was confirmed that the formulation was not stable due to the precipitation phenomenon. Examples 1-1 to 1-3 were slightly cloudy immediately after preparation, but after filtration with a 0.2 μm filter, they showed a transparent property and thus it was confirmed that they could be used as a preparation for injection. As a result, it was concluded that stable injectable preparations can be made at a GCA of 2.2% or more based on 5.0% PPC. The particle size of the compositions of Comparative Examples 1-1 to 1-4 were in a range of 198.2±721.0 nm to 28.2±11.35 nm, that is the composition is dispersed as unstable emulsion or liposome, so that it was judged that a substantially stable formulation did not occur and was not suitable for injectable preparation. Other than that, the PPC complex compositions (Examples 1-1 to 1-12) added with GCA 2.2% or more (GCA/PPC molar ratio of 0.76 or more) were composed of a micelle structure with a size of 10 nm or less and the PPC complex compositions (Examples 1-7 to 1-12) added with GCA 2.8% or more (GCA/PPC molar ratio of 0.97 or more) were composed of micelle structures with a size of 5 nm or less and were found to be suitable for injectable preparation.

Since the viscosity of the PPC complex composition solubilized with GCA increases in proportion to the PPC concentration, a viscosity test was performed on various compositions. Specifically, the characteristics of PPC (2.5~20.0%) complex composition solubilized with GCA (1.4~11.2%) and PPC 5.0% complex composition solubilized with GCA (4.2~12.6%) were investigated based on the GCA concentration of 2.8% in which the PPC 5.0% is dispersed with the particle size of 5 nm or less. 500 ml of each of the above compositions was measured at room temperature (25° C.) for 3 minutes at 60 RPM after mounting spin needle No. 1. As a result of the test, it was confirmed that the particle size was 4.23±1.69 to 1.37±0.530 nm, and the transparency (660 nm) was measured as 99.11±0.77%. Table 5 shows the viscosity characteristics of PPC injectable preparations solubilized with various concentrations of GCA. Based on the following Table 5, it was confirmed that when the PPC exceeds 15% (w/v), it is inadequate for administration due to the high viscosity.

TABLE 5

| PPC % (w/v) | GCA % (w/v) | Vicosity (cP) | PPC % (w/v) | GCA % (w/v) | Vicosity (cP) |
|---|---|---|---|---|---|
| 2.5 | 1.4 | 0.02 | 5.0 | 2.8 | 0.25 |
| 5.0 | 2.8 | 0.25 |  | 4.2 | 0.09 |

TABLE 5-continued

| PPC % (w/v) | GCA % (w/v) | Vicosity (cP) | PPC % (w/v) | GCA % (w/v) | Vicosity (cP) |
|---|---|---|---|---|---|
| 6.0 | 3.4 | 1.90 | 5.6 | | 0.43 |
| 7.0 | 3.9 | 5.71 | 7.0 | | 0.44 |
| 8.0 | 4.5 | 7.22 | 8.4 | | 0.44 |
| 9.0 | 5.0 | 7.87 | 9.8 | | 0.49 |
| 10.0 | 5.6 | 8.70 | 12.6 | | 0.96 |
| 11.0 | 6.2 | 12.87 | | | |
| 12.0 | 6.7 | 14.76 | | | |
| 13.0 | 7.3 | 17.86 | | | |
| 14.0 | 7.8 | 22.16 | | | |
| 15.0 | 8.4 | 24.16 | | | |
| 16.0 | 9.0 | 25.96 | | | |
| 17.0 | 9.5 | 27.95 | | | |
| 18.0 | 10.1 | 50.49 | | | |
| 19.0 | 10.6 | 74.20 | | | |
| 20.0 | 11.2 | 176.00 | | | |

Example 2: Preparing PPC Injectable Preparations Solubilized with TCA

As shown in Table 6 and 7 below, compositions based on phosphatidylcholine (PPC) solubilized with taurocholic acid (TCA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%), 26.0 mg (2.6%), 27.0 mg (2.7%), 28.0 mg (2.8%), 29.0 mg (2.9%), 30.0 mg (3.0%), 35.0 mg (3.5%), 40.0 mg (4.0%) or 45.0 mg (4.5%) of TCA respectively, and adding 9 mg of benzyl alcohol (0.9%) in 1 ml. The specific preparing method is the same as that of the above-mentioned Example 1. The tables 6 and 7 show the characteristics of PPC injectable preparation solubilized with various concentrations of TCA.

TABLE 6

| | Comparative Example 2-1 | Comparative Example 2-2 | Comparative Example 2-3 | Comparative Example 2-4 | Comparative Example 2-5 | Comparative Example 2-6 | Comparative Example 2-7 | Example 2-1 |
|---|---|---|---|---|---|---|---|---|
| PPC % (w/v) | 5.0 | 5.0 | 5.0 | 5.0 | 5.0 | 5.0 | 5.0 | 5.0 |
| GCA % (w/v) | 1.0 | 1.5 | 2.0 | 2.1 | 2.2 | 2.3 | 2.4 | 2.5 |
| GCA/PPC Molar ratio | 0.31 | 0.47 | 0.63 | 0.66 | 0.69 | 0.72 | 0.75 | 0.78 |
| Property (after preparation) | Very cloudy | Very cloudy | Very cloudy | Very cloudy | Very cloudy | Very cloudy | Cloudy | Slightly Cloudy |
| Property (at 30 days after preparation) | Precipitation | Precipitation | Precipitation | Precipitation | Precipitation | Precipitation | Precipitation | Transparent |
| Transparency (660 nm) | 28.26 | 28.58 | 30.97 | 34.54 | 36.24 | 36.74 | 43.88 | 94.2 |
| Particle size (nm) | 139.6 ± 126.14 | 160.0 ± 158.80 | 170.8 ± 121.60 | 153.2 ± 2474 | 120.3 ± 1.60 | 149.5 ± 798.0 | 146.1 ± 2908 | 9.88 ± 1.420 |
| pH | 7.22 | 7.26 | 7.22 | 7.25 | 7.22 | 7.24 | 7.25 | 7.15 |

TABLE 7

| | Example 2-2 | Example 2-3 | Example 2-4 | Example 2-5 | Example 2-6 | Example 2-7 | Example 2-8 | Example 2-9 |
|---|---|---|---|---|---|---|---|---|
| PPC % (w/v) | 5.0 | 5.0 | 5.0 | 5.0 | 5.0 | 5.0 | 5.0 | 5.0 |
| TCA % (w/v) | 2.6 | 2.7 | 2.8 | 2.9 | 3.0 | 3.5 | 4.0 | 4.5 |
| TCA/PPC Molar ratio | 0.81 | 0.85 | 0.88 | 0.91 | 0.94 | 1.10 | 1.25 | 1.41 |
| Property (after preparation) | Transparent | Transparent | Transparent | Transparent | Transparent | Transparent | Transparent | Transparent |
| Property (at 30 days after preparation) | Transparent | Transparent | Transparent | Transparent | Transparent | Transparent | Transparent | Transparent |
| Transparency (660 nm) | 97.39 | 95.29 | 99.6 | 99.54 | 99.83 | 99.82 | 99.81 | 99.76 |
| Particle size (nm) | 7.01 ± 1.030 | 6.63 ± 0.960 | 3.74 ± 0.820 | 2.710 ± 1.030 | 3.56 ± 0.750 | 2.88 ± 0.600 | 2.39 ± 0.510 | 2.78 ± 0.690 |
| pH | 7.19 | 7.17 | 7.15 | 7.26 | 7.20 | 7.21 | 7.25 | 7.20 |

Figure 2C:
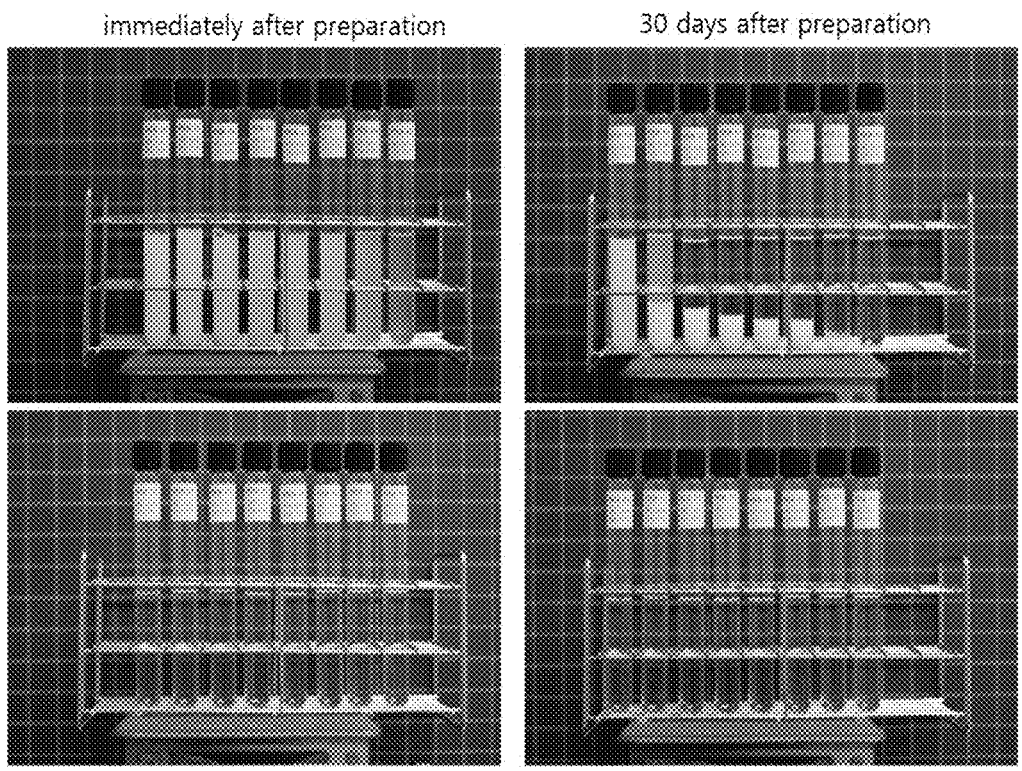

The formulation stability of the PPC injectable compositions solubilized with taucholic acid (TCA) in Tables 6 and 7 was evaluated immediately after the preparation and 30 days after the preparation (refrigerated storage), and the evaluation results are shown in FIG. 2C. When TCA was added at 2.5% or more with respect to PPC 5.0%, it was confirmed that the formulation was stable, and the composition showed transparent (clear) solution properties (Examples 2-1 to 2-9). In Comparative Examples 2-1 to 2-7, it was confirmed that the formulation was not stable due to the precipitation phenomenon. Examples 2-1 were slightly cloudy immediately after preparation, but after filtration with a 0.2 μm filter, they showed a transparent property and thus it was confirmed that they could be used as a preparation for injection. As a result, it was concluded that stable injectable preparations can be made at a TCA of 2.5% or more based on 5.0% PPC. The particle size of the compositions of Comparative Examples 2-1 to 2-7 were in a range of 139.6±126.14 nm to 146.1±2908 nm, that is the composition is dispersed as unstable emulsion or liposome, so that it was judged that a substantially stable formulation did not occur and was not suitable for injectable preparation. Other than that, the PPC complex compositions (Examples 2-1 to 2-9) added with TCA 2.5% or more (TCA/PPC molar ratio of 0.78 or more) were composed of a micelle structure with a size of 10 nm or less and the PPC complex compositions (Examples 2-4 to 2-9) added with TCA 2.8% or more (TCA/PPC molar ratio of 0.88 or more) were composed of micelle structures with a size of 5 nm or less and were found to be suitable for injectable preparation.

Comparative Example 3: PPC Injectable Preparations Solubilized with CA

As shown in Table 8 below, compositions based on phosphatidylcholine (PPC) solubilized with cholic acid (CA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%) or 30.0 mg (3.0%) of CA respectively, and adding 9 mg of benzyl alcohol (0.9%) in 1 ml. The specific preparing method is the same as that of the above-mentioned Example 1.

<TABLE. 8>

Figure 2D:
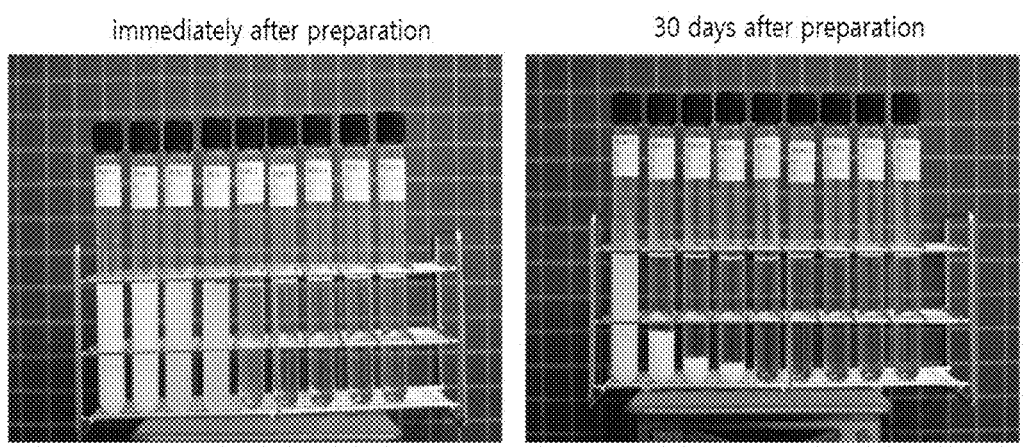

The formulation stability of the PPC injectable compositions solubilized with cholic acid (CA) in Tables 8 was evaluated immediately after the preparation and 30 days after the preparation (refrigerated storage), and the evaluation results are shown in FIG. 2D. When CA was added at 2.2% or more with respect to PPC 5.0%, it was confirmed that the formulation was stable, and the composition showed transparent (clear) solution properties (Comparative Examples 3-5 to 3-9). In Comparative Examples 3-1 to 3-4, it was confirmed that the formulation was not stable due to the precipitation phenomenon. Comparative Example 3-5 was almost transparent immediately after preparation, and after filtration with a 0.2 μm filter, it showed a transparent property. As a result, it was concluded that stable injectable preparations can be made at a CA of 2.2% or more based on 5.0% PPC. The particle size of the compositions of Comparative Examples 3-1 to 3-4 were in a range of 50.80±330 nm to 583.00±293 nm, that is the composition is dispersed as unstable emulsion or liposome, but Comparative Examples 3-5 to 3-9 were composed of a micelle structure with a size of 10 nm or less. As described above, it was judged that a substantially stable formulation did not occur in the composition having CA/PPC molar ratio of less than 0.88, and it was not suitable for injectable preparation.

Comparative Example 4: PPC Injectable Preparations Solubilized with CDCA

As shown in Table 9 below, compositions based on phosphatidylcholine (PPC) solubilized with chenodeoxycholic acid (CDCA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%) or 30.0 mg (3.0%) of CDCA respectively, and adding 9 mg of benzyl alcohol (0.9%) in 1 ml. The specific preparing method is the same as that of the above-mentioned Example 1.

TABLE 8

|  | Comparative Example 3-1 | Comparative Example 3-2 | Comparative Example 3-3 | Comparative Example 3-4 | Comparative Example 3-5 | Comparative Example 3-6 | Comparative Example 3-7 | Comparative Example 3-8 | Comparative Example 3-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| CA % (w/v) | 1.00 | 1.50 | 2.00 | 2.10 | 2.20 | 2.30 | 2.40 | 2.50 | 3.00 |
| CA/PPC Molar ratio | 0.40 | 0.60 | 0.80 | 0.84 | 0.88 | 0.91 | 0.95 | 0.99 | 1.19 |
| Property (after preparation) | Very cloudy | Very cloudy | Cloudy | Cloudy | Almost Transparent | Transparent | Transparent | Transparent | Transparent |
| Property (at 30 days after preparation) | Precipitation | Precipitation | Precipitation | Precipitation | Transparent | Transparent | Transparent | Transparent | Transparent |
| Transparency (660 nm) | 24.2 | 27.41 | 44.46 | 63.64 | 95.56 | 99.66 | 99.62 | 99.71 | 99.73 |
| Particle size (nm) | 50.80 ± 330.0 | 72.70 ± 492.0 | 2105 ± 956 | 583.0 ± 293 | 6.22 ± 0.880 | 3.20 ± 0.760 | 3.20 ± 0.690 | 3.21 ± 0.660 | 2.63 ± 0.580 |

TABLE 9

|  | Comparative Example 4-1 | Comparative Example 4-2 | Comparative Example 4-3 | Comparative Example 4-4 | Comparative Example 4-5 | Comparative Example 4-6 | Comparative Example 4-7 | Comparative Example 4-8 | Comparative Example 4-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| CDCA % (w/v) | 1.0 | 1.5 | 2.0 | 2.1 | 2.2 | 2.3 | 2.4 | 2.5 | 3.0 |
| CDCA/PPC Molar ratio | 0.40 | 0.61 | 0.81 | 0.85 | 0.89 | 0.93 | 0.97 | 1.01 | 1.21 |
| Property (after preparation) | Very cloudy | Very cloudy | Cloudy | Cloudy | Transparent | Transparent | Transparent | Transparent | Transparent |
| Property (at 30 days after preparation) | Precipitation | Precipitation | Precipitation | Precipitation | Transparent | Transparent | Transparent | Transparent | Transparent |
| Transparency (660 nm) | 21.4 | 21.47 | 37.46 | 48.38 | 98.79 | 99.05 | 98.78 | 99.45 | 99.28 |
| Particle size (nm) | 80.05 ± 280.0 | 1250 ± 478.0 | 93.76 ± 6.100 | 35.73 ± 0.830 | 3.47 ± 0.960 | 3.98 ± 0.910 | 3.64 ± 0.941 | 3.08 ± 0.920 | 3.89 ± 0.890 |

Figure 2E:
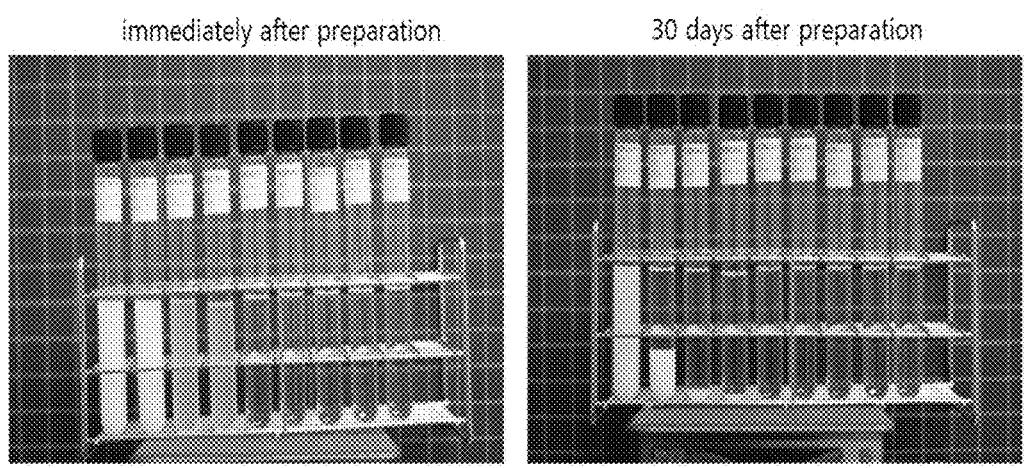

The formulation stability of the PPC injectable compositions solubilized with chenodoxycholic acid (CDCA) in Tables 9 was evaluated immediately after the preparation and 30 days after the preparation (refrigerated storage), and the evaluation results are shown in FIG. 2E. When CDCA was added at 2.2% or more with respect to PPC 5.0%, it was confirmed that the formulation was stable, and the composition showed transparent (clear) solution properties (Comparative Examples 4-5 to 4-9). In Comparative Examples 4-1 to 4-4, it was confirmed that the formulation was not stable due to the precipitation phenomenon. As a result, it was concluded that stable injectable preparations can be made at a CDCA of 2.2% or more based on 5.0% PPC. The particle size of the compositions of Comparative Examples 4-1 to 4-4 were in a range of 80.05±280.0 nm to 35.73±0.830 nm, that is the composition is dispersed as unstable emulsion or liposome, but Comparative Examples 4-5 to 4-9 were composed of a micelle structure with a size of 10 nm or less. As described above, it was judged that a substantially stable formulation did not occur in the composition having CDCA/PPC molar ratio of less than 0.89, and it was not suitable for injectable preparation.

Comparative Example 5: PPC Injectable Preparations Solubilized with UDCA

As shown in Table 10 below, compositions based on phosphatidylcholine (PPC) solubilized with ursodeoxycholic acid (UDCA) was prepared by adding 50.0 mg of PPC (5.0%) and 10.0 mg (1.0%), 15.0 mg (1.5%), 25.0 mg (2.5%), 26.0 mg (2.6%), 27.0 mg (2.7%), 28.0 mg (2.8%), 29.0 mg (2.9%) or 30.0 mg (3.0%) of UDCA respectively, and adding 9 mg of benzyl alcohol (0.9%) in 1 ml. The specific preparing method is the same as that of the above-mentioned Example 1.

TABLE 10

|  | Comparative Example 5-1 | Comparative Example 5-2 | Comparative Example 5-3 | Comparative Example 5-4 | Comparative Example 5-5 | Comparative Example 5-6 | Comparative Example 5-7 | Comparative Example 5-8 | Comparative Example 5-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| UDCA % (w/v) | 1.0 | 1.5 | 2.0 | 2.5 | 2.6 | 2.7 | 2.8 | 2.9 | 3.0 |
| UDCA/PPC Molar ratio | 0.42 | 0.62 | 0.83 | 1.04 | 1.08 | 1.12 | 1.16 | 1.20 | 1.25 |
| Property (after preparation) | Very cloudy | Very cloudy | Very cloudy | Very cloudy | Cloudy | Almost transparent | Transparent | Transparent | Transparent |
| Property (at 30 days after preparation) | Precipitation | Precipitation | Precipitation | Precipitation | Precipitation | Transparent | Transparent | Transparent | Transparent |
| Transparency (660 nm) | 30.79 | 37.9 | 38.48 | 52.4 | 66.43 | 92.59 | 99.45 | 99.65 | 99.82 |
| Particle size (nm) | 289.0 ± 265.0 | 2698 ± 2475 | 83.20 ± 773.1 | 69.43 ± 315.0 | 42.42 ± 250 | 6.24 ± 0.430 | 2.31 ± 0.380 | 2.09 ± 0.450 | 2.22 ± 0.410 |

Figure 2F:
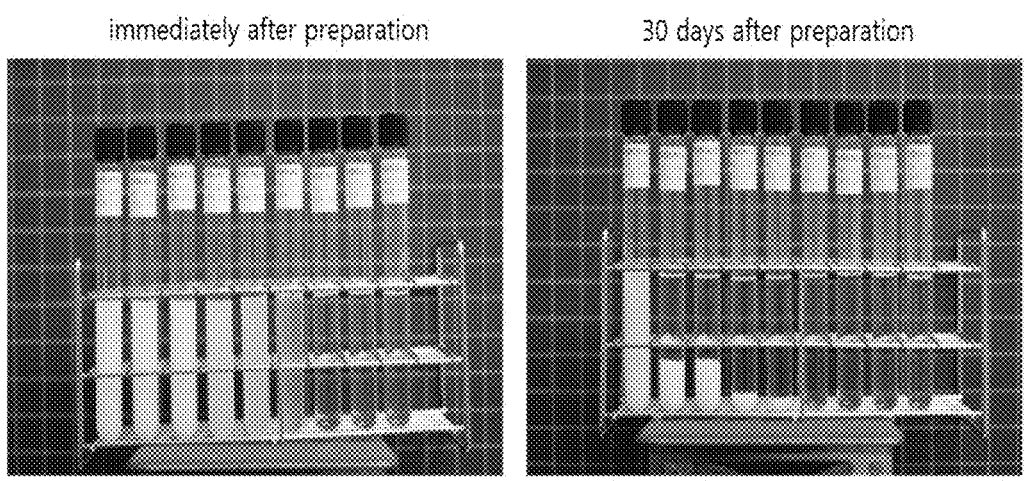

The formulation stability of the PPC injectable compositions solubilized with ursodoxycholic acid (UDCA) in Tables 10 was evaluated immediately after the preparation and 30 days after the preparation (refrigerated storage), and the evaluation results are shown in FIG. 2F. When UDCA was added at 2.7% or more with respect to PPC 5.0%, it was confirmed that the formulation was stable, and the composition showed transparent (clear) solution properties (Comparative Examples 5-6 to 5-9). In Comparative Examples 5-1 to 5-5, it was confirmed that the formulation was not stable due to the precipitation phenomenon. Comparative Example 5-6 was almost transparent immediately after preparation, and after filtration with a 0.2 μm filter, it showed a transparent property. As a result, it was concluded that stable injectable preparations can be made at a UDCA of 2.7% or more based on 5.0% PPC. The particle size of the compositions of Comparative Examples 5-1 to 5-5 were in a range of 289.0±265.0 nm to 42.42±250 nm, that is the composition is dispersed as unstable emulsion or liposome, but Comparative Examples 5-6 to 5-9 were composed of a micelle structure with a size of 10 nm or less. As described above, it was judged that a substantially stable formulation did not occur in the composition having UDCA/PPC molar ratio of less than 1.12, and it was not suitable for injectable preparation.

Comparative Example 6: PPC Injectable Preparations Solubilized with GDCA

As shown in Table 11 below, compositions based on phosphatidylcholine (PPC) solubilized with glycodeoxycholic acid (GDCA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%) or 30.0 mg (3.0%) of GDCA respectively, and adding 9 mg of benzyl alcohol (0.9%) in 1 ml. The specific preparing method is the same as that of the above-mentioned Example 1.

Figure 2G:
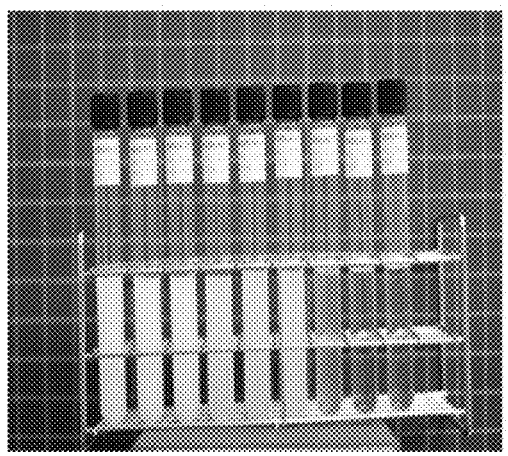
Figure 2G:
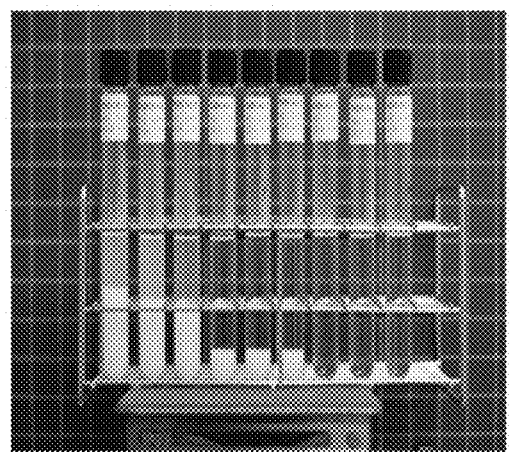

The formulation stability of the PPC injectable compositions solubilized with glycodeoxycholic acid (GDCA) in Tables 11 was evaluated immediately after the preparation and 30 days after the preparation (refrigerated storage), and the evaluation results are shown in FIG. 2G. When GDCA was added at 2.4% or more with respect to PPC 5.0%, it was confirmed that the formulation was stable, and the composition showed transparent (clear) solution properties (Comparative Examples 6-7 to 6-9). In Comparative Examples 6-1 to 6-6, it was confirmed that the formulation was not stable due to the precipitation phenomenon. Comparative Example 6-7 was almost transparent immediately after preparation, and after filtration with a 0.2 μm filter, it showed a transparent property. As a result, it was concluded that stable injectable preparations can be made at a GDCA of 2.4% or more based on 5.0% PPC. The particle size of the compositions of Comparative Examples 6-1 to 6-6 were in a range of 204.4±1880 nm to 134.8±680.1 nm, that is the composition is dispersed as unstable emulsion or liposome, but Comparative Examples 6-7 to 6-9 were composed of a micelle structure with a size of 10 nm or less. As described above, it was judged that a substantially stable formulation did not occur in the composition having GDCA/PPC molar ratio of less than 0.87, and it was not suitable for injectable preparation.

Comparative Example 7: PPC Injectable Preparations Solubilized with TDCA

As shown in Table 12 below, compositions based on phosphatidylcholine (PPC) solubilized with taurodeoxycholic acid (TDCA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%) or 30.0 mg (3.0%) of TDCA respectively, and adding 9 mg of benzyl alcohol (0.9%) in 1 ml. The specific preparing method is the same as that of the above-mentioned Example 1.

TABLE 11

|  | Comparative Example 6-1 | Comparative Example 6-2 | Comparative Example 6-3 | Comparative Example 6-4 | Comparative Example 6-5 | Comparative Example 6-6 | Comparative Example 6-7 | Comparative Example 6-8 | Comparative Example 6-9 |
| --- | --- | --- | --- | --- | --- | --- | --- | --- | --- |
| PPC % (w/v) | 5.0 | 5.0 | 5.0 | 5.0 | 5.0 | 5.0 | 5.0 | 5.0 | 5.0 |
| GDCA % (w/v) | 1.0 | 1.5 | 2.0 | 2.1 | 2.2 | 2.3 | 2.4 | 2.5 | 3.0 |
| GDCA/PPC Molar ratio | 0.36 | 0.54 | 0.73 | 0.76 | 0.80 | 0.84 | 0.87 | 0.91 | 1.09 |
| Property (after preparation) | Very cloudy | Very cloudy | Very cloudy | Cloudy | Cloudy | Cloudy | Almost transparent | Transparent | Transparent |
| Property (at 30 days after preparation) | Precipitation | Precipitation | Precipitation | Precipitation | Precipitation | Precipitation | Transparent | Transparent | Transparent |
| Transparency (660 nm) | 21.68 | 34.67 | 30.94 | 46.88 | 48.39 | 58.6 | 92.43 | 99.76 | 99.83 |
| Particle size (nm) | 204.4 ± 1880 | 344.0 ± 3215 | 95.22 ± 246.0 | 231.3 ± 348.2 | 155.4 ± 270.3 | 134.8 ± 680.1 | 3.91 ± 0.420 | 4.87 ± 0.300 | 2.78 ± 0.260 |

TABLE 12

|  | Comparative Example 7-1 | Comparative Example 7-2 | Comparative Example 7-3 | Comparative Example 7-4 | Comparative Example 7-5 | Comparative Example 7-6 | Comparative Example 7-7 | Comparative Example 7-8 | Comparative Example 7-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| TDCA % (w/v) | 1.0 | 1.5 | 2.0 | 2.1 | 2.2 | 2.3 | 2.4 | 2.5 | 3.0 |
| TDCA/PPC Molar ratio | 0.32 | 0.48 | 0.64 | 0.67 | 0.71 | 0.74 | 0.77 | 0.80 | 0.96 |
| Property (after preparation) | Very cloudy | Very cloudy | Very cloudy | Very cloudy | Cloudy | Almost transparent | Transparent | Transparent | Transparent |
| Property (at 30 days after preparation) | Precipitation | Precipitation | Precipitation | Precipitation | Precipitation | Transparent | Transparent | Transparent | Transparent |
| Transparency (660 nm) | 33.24 | 29.56 | 25.12 | 41.58 | 53.68 | 87.82 | 99.45 | 99.78 | 99.98 |
| Particle size (nm) | 185.1 ± 1834 | 307.2 ± 90.90 | 199.2 ± 163.2 | 229.0 ± 330.9 | 123.5 ± 72.0 | 1.46 ± 0.410 | 1.80 ± 0.320 | 1.71 ± 0.450 | 1.85 ± 0.380 |

Figure 2H:
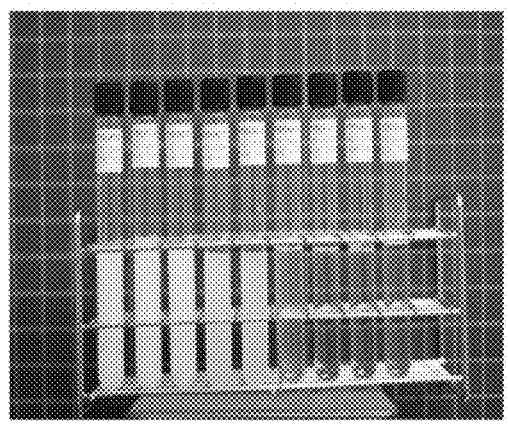
Figure 2H:
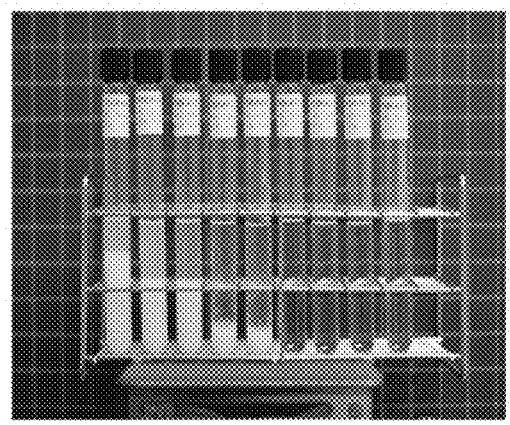

The formulation stability of the PPC injectable compositions solubilized with taurodeoxycholic acid (TDCA) in Tables 12 was evaluated immediately after the preparation and 30 days after the preparation (refrigerated storage), and the evaluation results are shown in FIG. 2H. When TDCA was added at 2.3% or more with respect to PPC 5.0%, it was confirmed that the formulation was stable, and the composition showed transparent (clear) solution properties (Comparative Examples 7-6 to 7-9). In Comparative Examples 7-1 to 7-5, it was confirmed that the formulation was not stable due to the precipitation phenomenon. Comparative Example 7-6 was almost transparent immediately after preparation, and after filtration with a 0.2 μm filter, it showed a transparent property. As a result, it was concluded that stable injectable preparations can be made at a TDCA of 2.3% or more based on 5.0% PPC. The particle size of the compositions of Comparative Examples 7-1 to 7-5 were in a range of 185.1±1834 nm to 123.5±72.0 nm, that is the composition is dispersed as unstable emulsion or liposome, but Comparative Examples 7-6 to 7-9 were composed of a micelle structure with a size of 10 nm or less. As described above, it was judged that a substantially stable formulation did not occur in the composition having TDCA/PPC molar ratio of less than 0.74, and it was not suitable for injectable preparation.

Comparative Example 8: PPC Injectable Preparations Solubilized with HDCA

As shown in Table 13 below, compositions based on phosphatidylcholine (PPC) solubilized with hyodeoxycholic acid (HDCA) was prepared by adding 50.0 mg of PPC (5.0%) and 10.0 mg (1.0%), 15.0 mg (1.5%), 20.0 mg (2.0%), 21.0 mg (2.1%), 22.0 mg (2.2%), 23.0 mg (2.3%), 24.0 mg (2.4%), 25.0 mg (2.5%) or 30.0 mg (3.0%) of HDCA respectively, and adding 9 mg of benzyl alcohol (0.9%) in 1 ml. The specific preparing method is the same as that of the above-mentioned Example 1.

TABLE 13

|  | Comparative Example 8-1 | Comparative Example 8-2 | Comparative Example 8-3 | Comparative Example 8-4 | Comparative Example 8-5 | Comparative Example 8-6 | Comparative Example 8-7 | Comparative Example 8-8 | Comparative Example 8-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| HDCA % (w/v) | 1.0 | 1.5 | 2.0 | 2.1 | 2.2 | 2.3 | 2.4 | 2.5 | 3.0 |
| HDCA/PPC Molar ratio | 0.41 | 0.62 | 0.82 | 0.86 | 0.91 | 0.95 | 0.99 | 1.03 | 1.24 |
| Property (after preparation) | Very cloudy | Very cloudy | Very cloudy | Very cloudy | Very cloudy | Almos transparent | Transparent | Transparent | Transparent |
| Property (at 30 days after preparation) | Precipitation | Precipitation | Precipitation | Precipitation | Precipitation | Transparent | Transparent | Transparent | Transparent |
| Transparency (660 nm) | 26.53 | 26.89 | 25.97 | 26.74 | 35.61 | 96.38 | 99.94 | 99.73 | 99.91 |
| Particle size (nm) | 537.2 ± 320 | 469.8 ± 33.20 | 168.3 ± 122 | 83.05 ± 650.5 | 81.65 ± 24.30 | 3.30 ± 0.980 | 3.21 ± 0.800 | 2.92 ± 1.150 | 3.47 ± 0.820 |

Figure 2I:
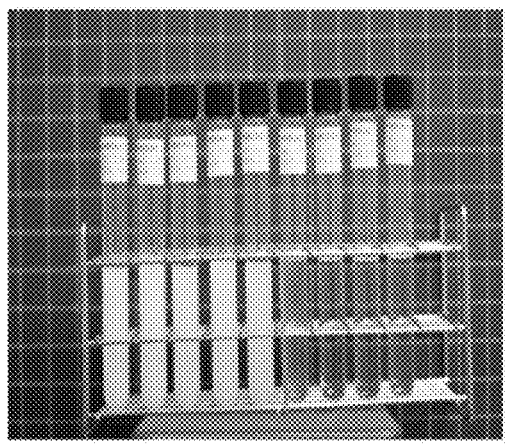
Figure 2I:

The formulation stability of the PPC injectable compositions solubilized with hyodeoxycholic acid (HDCA) in Tables 13 was evaluated immediately after the preparation and 30 days after the preparation (refrigerated storage), and the evaluation results are shown in FIG. 2I. When HDCA was added at 2.3% or more with respect to PPC 5.0%, it was confirmed that the formulation was stable, and the composition showed transparent (clear) solution properties (Comparative Examples 8-6 to 8-9). In Comparative Examples 8-1 to 8-5, it was confirmed that the formulation was not stable due to the precipitation phenomenon. Comparative Example 8-6 was almost transparent immediately after preparation, and after filtration with a 0.2 µm filter, it showed a transparent property. As a result, it was concluded that stable injectable preparations can be made at a HDCA of 2.3% or more based on 5.0% PPC. The particle size of the compositions of Comparative Examples 8-1 to 8-5 were in a range of 537.2±320 nm to 81.65±24.30 nm, that is the composition is dispersed as unstable emulsion or liposome, but Comparative Examples 8-6 to 8-9 were composed of a micelle structure with a size of 10 nm or less. As described above, it was judged that a substantially stable formulation did not occur in the composition having HDCA/PPC molar ratio of less than 0.95, and it was not suitable for injectable preparation.

Unusual findings were that the PPC complex composition solubilized with HDCA was cloudy when stored in cold (4~8° C.) and changed to a clear solution at room temperature. It has been concluded that the PPC+HDCA complex composition is poor in formulation stability during refrigerated storage and should be stored at room temperature for a long time. However, it was considered that HDCA was not a suitable solubilizing agent for quality control of PPC complex composition due to increase of lyso phosphatidylcholine which causes hemolysis when PPC+HDCA is stored at room temperature for a long time.

Comparative Example 9: PPC Injectable Preparations Solubilized with TUDCA

As shown in Table 14 below, compositions based on phosphatidylcholine (PPC) solubilized with tauroursodeoxycholic acid (TUDCA) was prepared by adding 50.0 mg of PPC (5.0%) and 10.0 mg (1.0%), 15.0 mg (1.5%), 20.0 mg (2.0%), 25.0 mg (2.5%), 30.0 mg (3.0%), 35.0 mg (3.5%), 40.0 mg (4.0%), 45.0 mg (4.5%) or 50.0 mg (5.0%) of TUDCA respectively, and adding 9 mg of benzyl alcohol (0.9%) in 1 ml. The specific preparing method is the same as that of the above-mentioned Example 1.

TABLE 14

|  | Comparative Example 9-1 | Comparative Example 9-2 | Comparative Example 9-3 | Comparative Example 9-4 | Comparative Example 9-5 | Comparative Example 9-6 | Comparative Example 9-7 | Comparative Example 9-8 | Comparative Example 9-9 |
|---|---|---|---|---|---|---|---|---|---|
| PPC % (w/v) | 5.0 | 5.0 | 5.0 | 5.0 | 5.0 | 5.0 | 5.0 | 5.0 | 5.0 |
| TUDCA % (w/v) | 1.0 | 1.5 | 2.0 | 2.5 | 3.0 | 3.5 | 4.0 | 4.5 | 5.0 |
| TUDCA/PPC Molar ratio | 0.32 | 0.48 | 0.64 | 0.80 | 0.97 | 1.13 | 1.29 | 1.45 | 1.61 |
| Property (after preparation) | Very cloudy | Very cloudy | Very cloudy | Cloudy | Cloudy | Cloudy | Transparent | Transparent | Transparent |
| Property (at 30 days after preparation) | Precipitation | Precipitation | Precipitation | Precipitation | Precipitation | Precipitation | Transparent | Transparent | Transparent |
| Transparency (660 nm) | 19.56 | 21.2 | 24.8 | 38.43 | 42.16 | 62.49 | 98.87 | 99.13 | 99.56 |
| Particle size (nm) | 86.30 ± 850.3 | 77.72 ± 110.3 | 51.02 ± 120.0 | 41.2 ± 58.2 | 26.2 ± 18.6 | 22.8 ± 0.980 | 2.07 ± 0.450 | 1.92 ± 0.650 | 2.20 ± 0.420 |

Figure 2J:
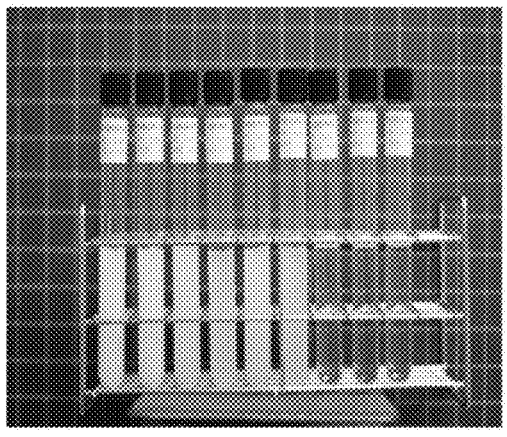
Figure 2J:
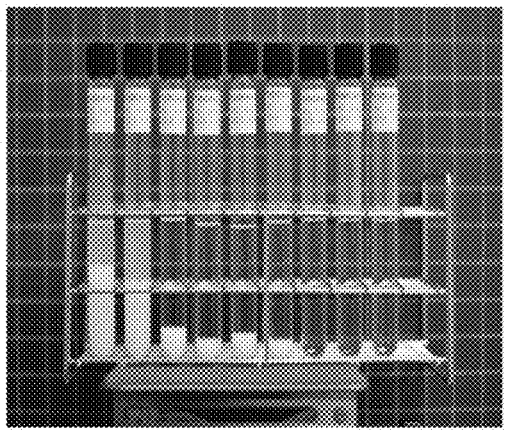

The formulation stability of the PPC injectable compositions solubilized with tauroursodeoxycholic acid (TUDCA) in Tables 14 was evaluated immediately after the preparation and 30 days after the preparation (refrigerated storage), and the evaluation results are shown in FIG. 2J. When TUDCA was added at 4.0% or more with respect to PPC 5.0%, it was confirmed that the formulation was stable, and the composition showed transparent (clear) solution properties (Comparative Examples 9-7 to 9-9). In Comparative Examples 9-1 to 9-6, it was confirmed that the formulation was not stable due to the precipitation phenomenon. As a result, it was concluded that stable injectable preparations can be made at a TUDCA of 4.0% or more based on 5.0% PPC. The particle size of the compositions of Comparative Examples 9-1 to 9-6 were in a range of 86.30±850 nm to 22.8±0.980 nm, that is the composition is dispersed as unstable emulsion or liposome, but Comparative Examples 9-7 to 9-9 were composed of a micelle structure with a size of 10 nm or less. As described above, it was judged that a substantially stable formulation did not occur in the composition having TUDCA/PPC molar ratio of less than 1.29, and it was not suitable for injectable preparation.

The table 15 below shows the most preferred minimum molar ratios of various bile acid (BA) to PPC (BA/PPC) among the preferred molar ratio of BA/PPC required for preparing PPC injectable compositions as described in Comparative Examples 1 to 9 and Example 1 and 2. The bile salts (BA) that can be used to prepare stable injectable compositions of clear solutions in which the PPC is dispersed in a micelle structure with the size of 10 nm or less in cold and room temperature conditions are deoxycholic acid (DCA), cholic acid (CA), glycocholic acid (GCA), taurocholic acid (TCA), chenodeoxycholic acid (CDCA), ursodeoxycholic acid (UDCA), glycodeoxycholic acid (GDCA), taurodeoxycholic acid (TDCA) and taururousodeoxycholic acid (TUDCA), and in room temperature conditions is hyodeoxycholic acid (HDCA). At the above-mentioned minimum molar ratios, these solubilize PPC to be dispersed as the micelle structure of a stable clear solution. The most preferable BA/PPC minimum molar ratio for solubilizing PPC with the bile acids (BA) is 0.92±0.17. That is, the most preferable BA/PPC minimum molar ratio is 0.74 to 1.29, as shown in Table 15 below. In order to solubilize PPC 5%, BA should be mixed with at least 2.49±0.56% (w/v).

TABLE 15

|  | DCA | CA | GCA | TCA | CDCA | UDCA | GDCA | TDCA | HDCA | TUDCA |
|---|---|---|---|---|---|---|---|---|---|---|
| PPC % (w/v) | 5.0 | 5.0 | 5.0 | 5.0 | 5.0 | 5.0 | 5.0 | 5.0 | 5.0 | 5.0 |
| BA % (w/v) | 2.1 | 2.2 | 2.2 | 2.5 | 2.2 | 2.7 | 2.4 | 2.3 | 2.3 | 4.0 |
| BA/PPC molar ratio | 0.87 | 0.88 | 0.76 | 0.78 | 0.89 | 1.12 | 0.87 | 0.74 | 0.95 | 1.29 |
| Property (after preparation) | Transparent | Transparent | Transparent | Transparent | Transparent | Transparent | Transparent | Transparent | Transparent | Transparent |
| Property (at 30 days after preparation) | Transparent | Transparent | Transparent | Transparent | Transparent | Transparent | Transparent | Transparent | Transparent | Transparent |
| Transparency (660 nm) | 99.41 | 95.56 | 88.0 | 94.2 | 98.79 | 92.59 | 92.43 | 87.82 | 96.38 | 98.87 |
| Particle size (nm) | 8.57 ± 0.7 | 3.22 ± 0.9 | 9.84 ± 1.8 | 9.88 ± 1.4 | 3.47 ± 1.0 | 2.24 ± 0.4 | 3.91 ± 0.4 | 1.46 ± 0.4 | 3.30 ± 1.0 | 2.07 ± 0.5 |

Comparative Example 10: PPC Injectable Preparations Solubilized with LCA

Compositions based on phosphatidylcholine (PPC 5.0%) solubilized with lithocholic acid (LCA) 3.0% (w/v) was prepared by the method the same as that of the above-mentioned Example 1.

Figure 3A:
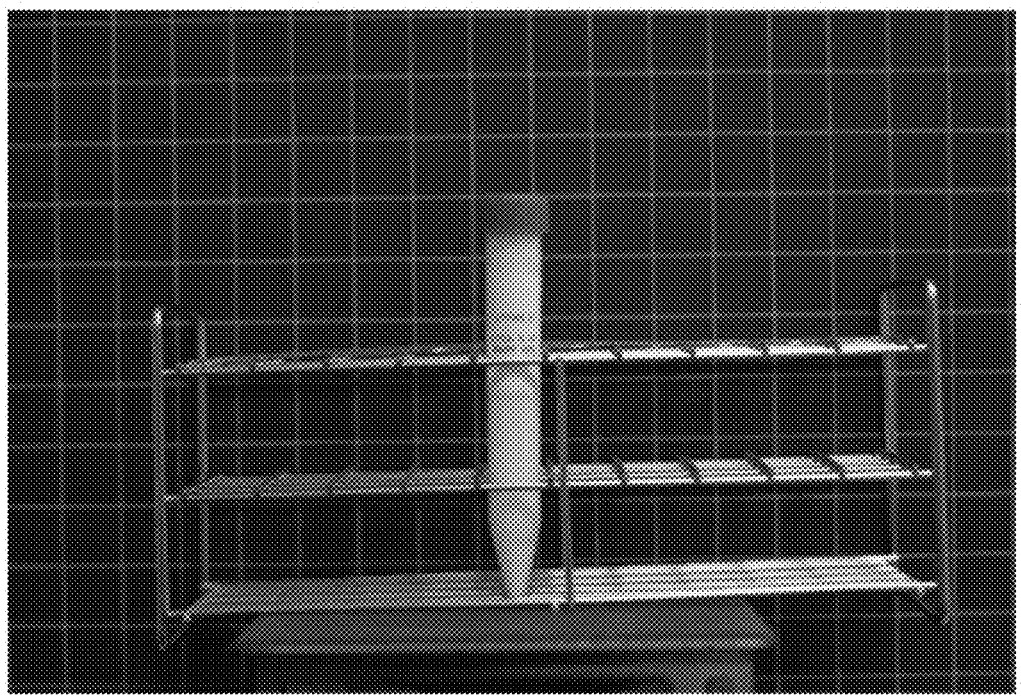
FIGS. 3A and 3B show an example of bile acids which cannot solubilize PPC and a description of the complex preparation of PPC solubilized with various concentrations of GCA.

However, as shown in FIG. 3A, lithocholic acid (LCA) exhibited cloudy and precipitation property due to gelation phenomenon when PPC was solubilized under sodium hydroxide.

Comparative Example 11: PPC Injectable Preparations Solubilized with DHCA

Figure 3B:
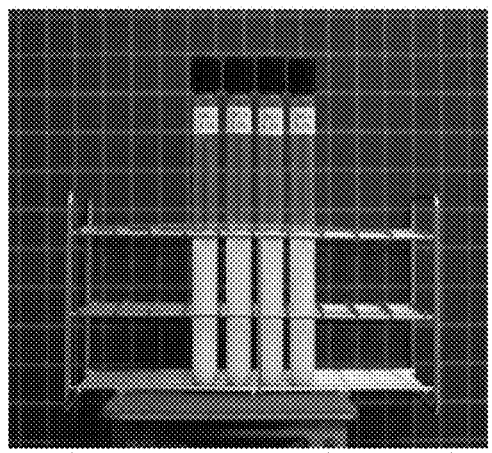
Figure 3B:
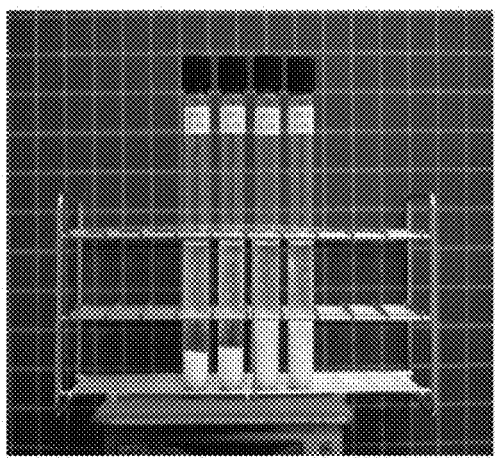

Compositions based on phosphatidylcholine (PPC 5.0%) solubilized with dihydrocholic acid (DHCA) 2.5%, 3.0%, 4.0% or 5.0% was prepared by the method the same as that of the above-mentioned Example 1. However, as shown in FIG. 3B, dihydrocholic acid (DHCA) exhibited cloudy property and precipitated property when pH was adjusted after solubilizing PPC with sodium hydroxide, so that it was not suitable for injectable composition.

Comparative Example 12 to 30: Preparing PPC Single, BA Single and PPC+BA Complex Compositions The injectable compositions of Deoxycholic acid (DCA) single (Comparative Example 12), cholic acid (CA) single (Comparative Example 13), glycocholic acid (GCA) single (Comparative Example 14), taurocholic acid (TCA) single (Comparative Example 15), chenodeoxycholic acid (CDCA) (Comparative Example 16), ursodeoxycholic acid (UDCA) single (Comparative Example 17), glycodeoxycholic acid (GDCA) single (Comparative Example 18), taurodeoxycholic acid (TDCA) single (Comparative Example 19), hyodeoxycholic acid (HDCA) single (Comparative Example 20) and tauroursodeoxycholic acid (TUDCA) single (Comparative Example 21) at various concentrations (1.0 to 7.5% (w/v), and the like) were prepared as single compositions. Specifically, the composition was prepared by adding 10.0 mg (1.0%), 25.5 mg (2.5%), 50.0 mg (5.0%) or 75.5 mg (7.5%) of bile acid, respectively, and 9 mg (0.9%) of benzyl alcohol. The process was that the water for injection was put into the preparation tank which was cleaned and sterilized (room temperature), and sodium hydroxide was added to the water for injection. Then the bile acids (salts) and benzyl alcohol were added, stirred and dissolved. Then, it was stirred at 200 RPM for about 2 hours under shading, sealing, room temperature (25° C.), and nitrogen pressure. After completion of the stirring, the pH was adjusted, and it was filtered through a 0.2 μm filter, and filled into the vial and sealed.

In addition, PPC single compositions of various concentrations [(PPC 1.25%, 2.50%, 5.0%, 7.5%, 10.0%, 12.5% and 15.0%) (Comparative Example 22)] were prepared. The specific preparing method is the same as that of Comparative Example 1.

And, PPC 5.0%+DCA 2.2% (Comparative Example 23), PPC 5.0%+HDCA 2.5% (Comparative Example 24), PPC 5.0%+UDCA 3.0% (Comparative Example 25), PPC 5.0%+TDCA 2.5% (Comparative Example 26), PPC 5.0%+GDCA 2.5% (Comparative Example 27), PPC 5.0%+CDCA 2.5% (Comparative Example 28), PPC 5.0%+CA 2.5% (Comparative Example 29) and PPC 5.0%+TUDCA 4.0% (Comparative Example 30) were prepared as complex compositions. The specific preparing method is the same as that of Comparative Example 2 to 9.

Example 3 and 4: Preparing PPC Complex Compositions Solubilized with GCA or TCA

The compositions of PPC+GCA[(PPC 2.5%+GCA 1.25%, PPC 5.0%+GCA 2.5%, PPC 7.5%+GCA 3.75%, PPC 10.0%+GCA 5.0%, PPC 15.0%+GCA 7.5%, PPC 5.0%+GCA 5.0%, PPC 5.0%+GCA 7.5%, PPC 5.0%+GCA 10.0%, PPC 5.0%+GCA 15.0%, PPC 5.0%+GCA 20.0% and PPC 5.0%+GCA 25.0%), (Example 3)] and PPC+TCA [(PPC 2.5%+TCA 1.25%, PPC 5.0%+TCA 2.5%, PPC 7.5%+TCA 3.75%, PPC 10.0%+TCA 5.0%, PPC 15.0%+TCA 7.5%, PC 5.0%+TCA 5.0%, PPC 5.0%+TCA 7.5%, PPC 5.0%+TCA 10.0%, PPC 5.0%+TCA 15.0%, PPC 5.0%+TCA 20.0% and PPC 5.0%+TCA 25.0%), (Example 4)] were prepared. The specific preparing method is the same as that of Example 1 and 2.

Test Example 1: The Comparison of Side Effects (Inflammation, Edema and Skin Lesion)

Phosphatidylcholine (PPC) single composition of various concentration (Comparative Example 22), bile acid (BA), single composition (Comparative Example 12 to 21), PPC complex composition solubilized with DCA, HD CA, UDCA, TDCA, GDCA, CDCA or CA (Comparative Example 23 to 29), and PPC complex composition solubilized with GCA or TCA (Example 3 and 4) were tested for edema, skin lesion and inflammation.

Inflammation, edema and local or extensive skin lesions at the site of administration are the typically observed local side effects of conventionally well-known and used DCA single injectable composition (such as, Kybella) or PPC injectable composition (such as, Lipostabil, Lipobean, etc.). The following results show edema, inflammation and skin lesion results for subcutaneous injection of bile acids (salt) single composition, PPC single compositions and a bile acid-solubilized PPC complex composition in vivo. From the following results, it was observed that the PPC injectable compositions solubilized with GCA, TCA or TUDCA at a particular molar ratio caused substantially none or 80% alleviated inflammation and edema. Such results were unpredictable findings from the evaluation of the efficacy of individual substances. The following test methods and results are described below. In the following, % of the composition means % (w/v).

1-1: Rat Paw Edema

To evaluate the degree of edema, each test compositions described above were injected into the paw of the rats. Specifically, male Sprague Dawley rats (6 weeks old) were purchased and used after one week of adaptation. The rats (body weight: 170~200 g) were randomly selected and the thickness of the rat paw were measured with a caliper before the administration of the test compositions. In order to observe the edema, 0.1 ml of PBS and the various test compositions were administered to the paws of the rats. Measurements of the paw volume were performed by a caliper immediately before the injection, immediately after the injection, and 1 or 2 hours after the injection. In addition, when the thickness was measured, the skin lesion of the injection site was observed by photographing the sole of the paw (using a 4×4 cm scale).

The degree of edema was evaluated as 0 to 4 grades. The degree of edema immediately after injection, and 1 or 2 hours after the injection was evaluated compared to before the injection in which the grades were no edema at all [−, (the degree of swelling was 0% compared to before the injection)], mild edema [+, (the degree of swelling was 1-20% compared to before the injection)], moderate edema [++, (the degree of swelling was 20-40% compared to before the injection)], severe edema [+++, (the degree of swelling was 40-60% compared to before the injection)], and extremely severe edema [++++, (the degree of swelling was 60% or more compared to before the injection)].

Figure 4A:
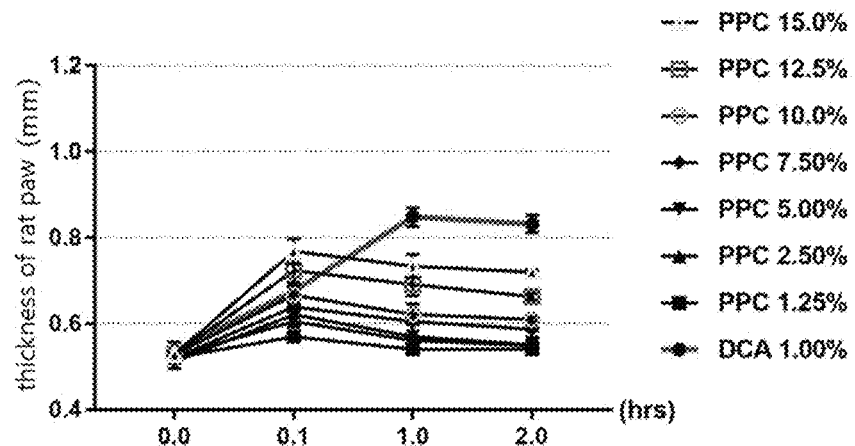
FIGS. 4A to 4Q show graphs showing the result of edema test in which the level of edema (the thickness of paws of rats (mm)) was measured immediately after and at 1 hour and 2 hours after injecting 0.1 ml of single composition of PPC, single compositions of various bile salts (DCA, HDCA, UDCA, TDCA, GDCA, CDCA, CA, GCA, TCA and TUDCA), complex compositions of various concentration of PPC solubilized with bile acid (DCA, GCA, TCA, etc), and PBS (rat paw thickness (mm)) to paws of rats. The test was repeated 4 times per treatment and was performed by a caliper. In the followings, % refers to % (w/v).
Figure 4B:
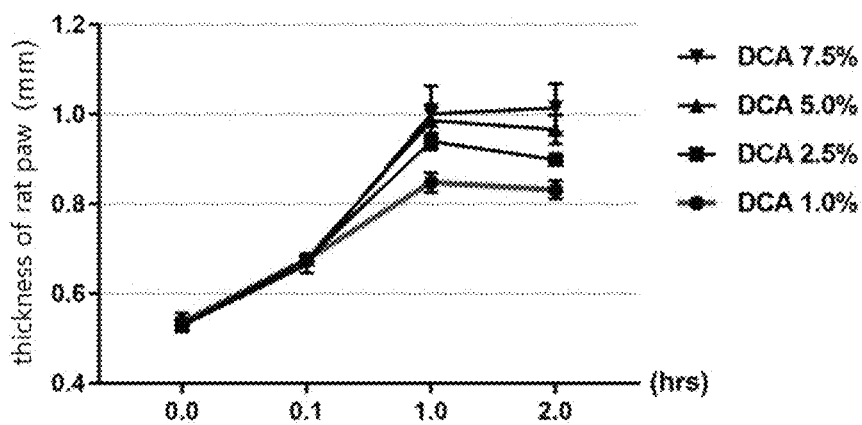
FIG. 4B shows the comparison results of edema after injection of various concentration of DCA single composition (1.0-7.5%).
Figure 4C:
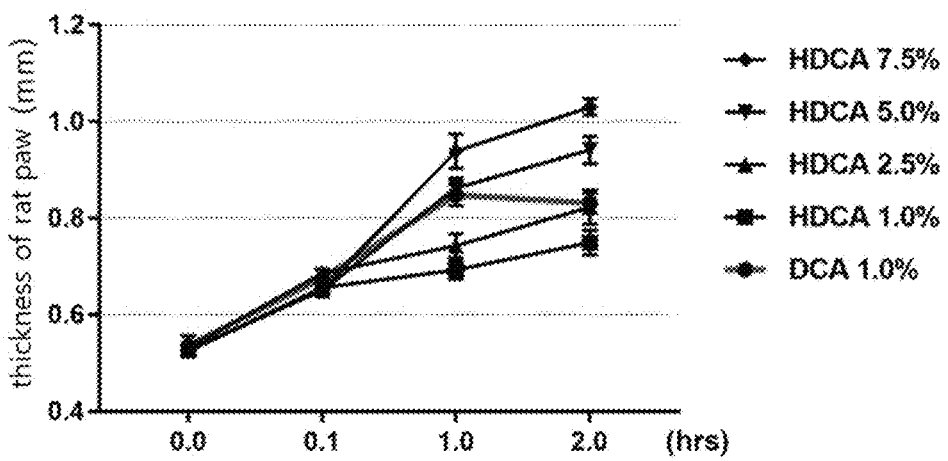
FIG. 4C shows the comparison results of edema after injection of various concentration of HDCA single composition (1.0-7.5%) and DCA 1% single composition.
Figure 4D:
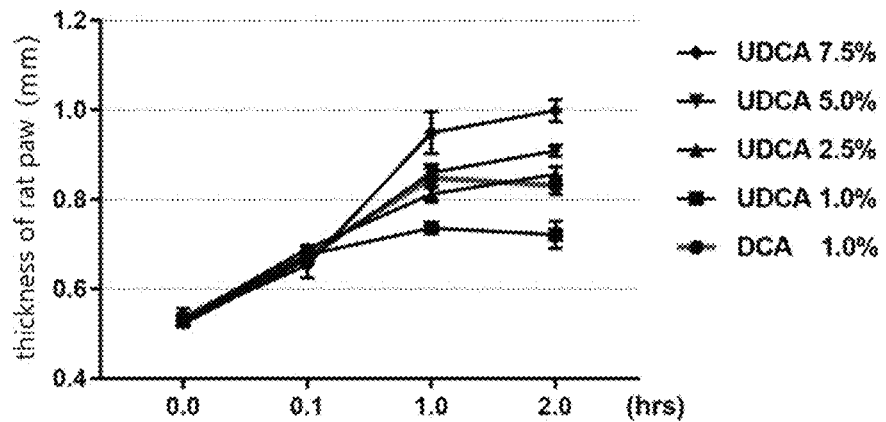
FIG. 4D shows the comparison results of edema after injection of various concentration of UDCA single composition (1.0-7.5%) and DCA 1% single composition.
Figure 4E:
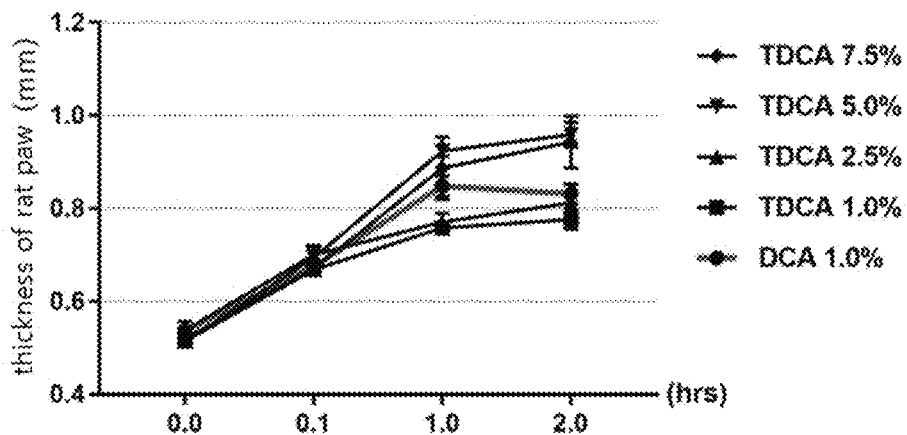
FIG. 4E shows the comparison results of edema after injection of various concentration of TDCA single composition (1.0-7.5%) and DCA 1% single composition.
Figure 4F:
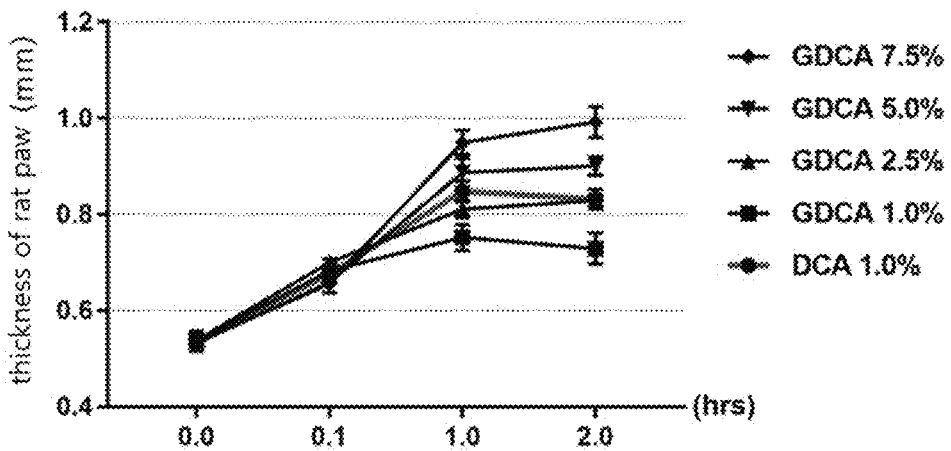
FIG. 4F shows the comparison results of edema after injection of various concentration of GDCA single composition (1.0-7.5%) and DCA 1% single composition.
Figure 4G:
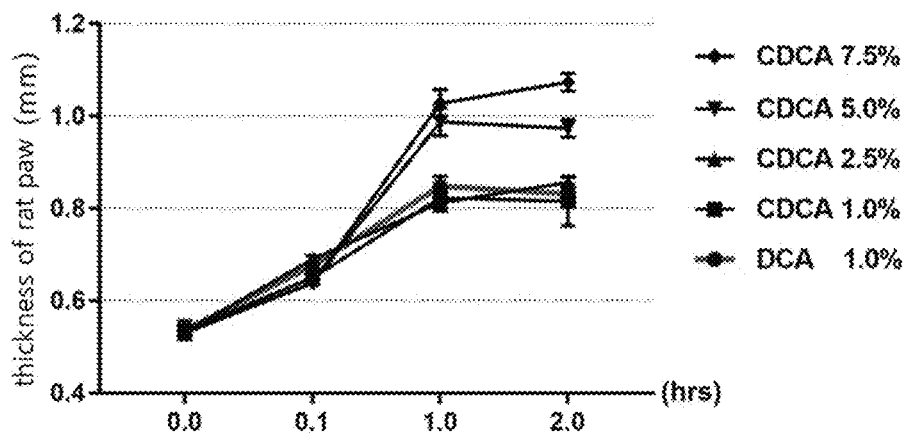
FIG. 4G shows the comparison results of edema after injection of various concentration of CDCA single composition (1.0-7.5%) and DCA 1% single composition.
Figure 4H:
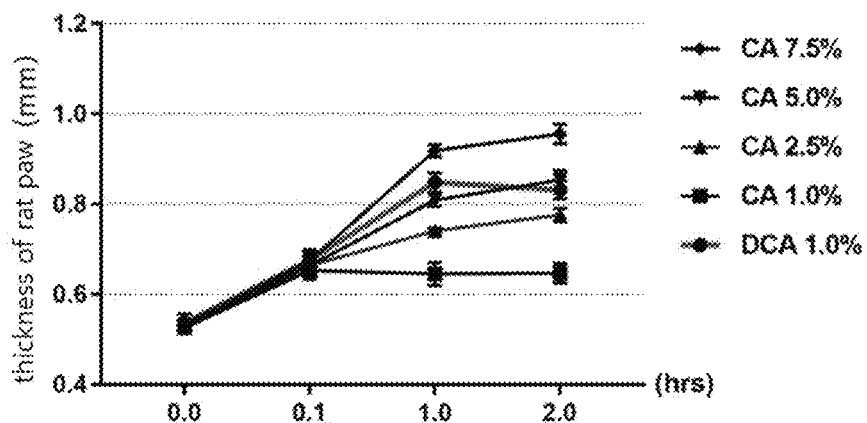
FIG. 4H shows the comparison results of edema after injection of various concentration of CA single composition (1.0-7.5%) and DCA 1% single composition.
Figure 4I:
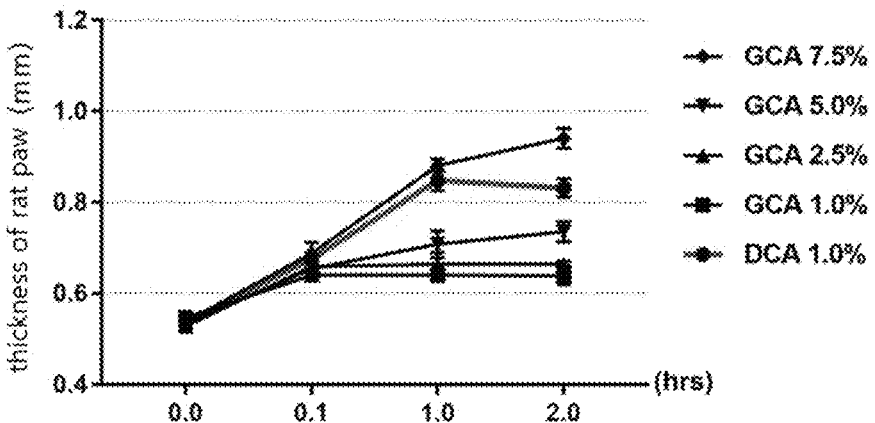
FIG. 4I shows the comparison results of edema after injection of various concentration of GCA single composition (1.0-7.5%) and DCA 1% single composition.
Figure 4J:
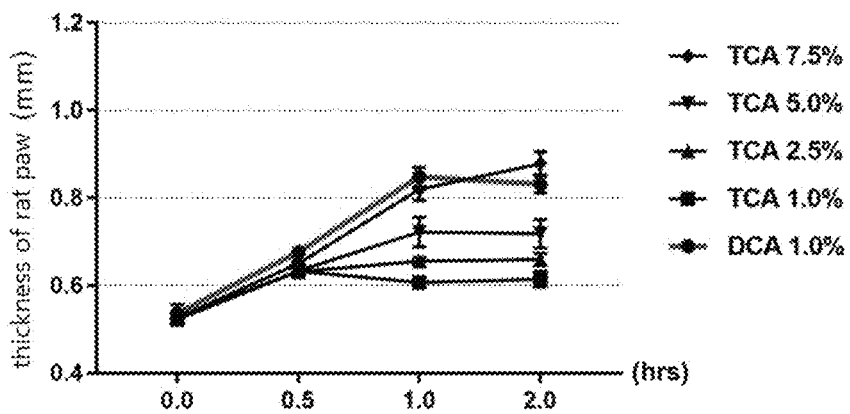
FIG. 4J shows the comparison results of edema after injection of various concentration of TCA single composition (1.0-7.5%) and DCA 1% single composition.
Figure 4K:
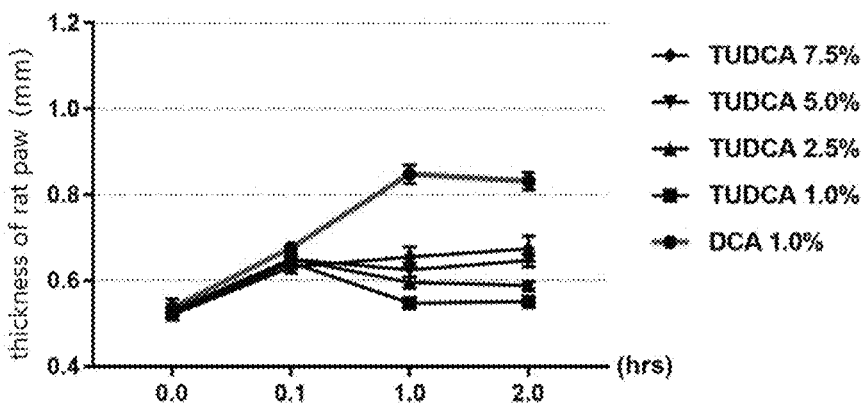
FIG. 4K shows the comparison results of edema after injection of various concentration of TUDCA single composition (1.0-7.5%) and DCA 1% single composition.

The results of the edema evaluation at 2 hours after the administration (when the edema is the most severe) of PPC single composition (PPC 1.25%, 2.50%, 5.0%, 7.5%, 10.0%, 12.5% or 15.0%) were as shown in the following Table 16 that "mild" grade was expanded from PPC 1.25% to 10.0%, "moderate" grade was shown in PPC 12.5% and 15.0%. The edema at 2 hours after the administration of DCA 1.0% was increased to "severe" (FIG. 4A). In conclusion, PPC single composition showed a concentration-dependent edema at high concentration, but PPC 15% single composition, that is the highest concentration, induced edema of significantly lower grade than that of DCA 1.0%.

TABLE 16

| PPC % (w/v) | Immediately after administration | 1 hour after administration | 2 hours after administration |
|---|---|---|---|
| 1.25 | + | + | + |
| 2.50 | + | + | + |
| 5.00 | + | + | + |
| 7.50 | ++ | + | + |
| 10.0 | ++ | + | + |
| 12.5 | ++ | ++ | ++ |
| 15.0 | +++ | ++ | ++ |

The results of edema evaluation at 2 hours after the administration of various concentrations of bile acids (1.0%, 2.5%, 5.0%, 7.5%), when the edema was the most severe, were as shown in the following Table 17 that "mild" grade was shown in TUDCA 1.0%, 2.5%, GCA 1.0% and TCA 1.0%, "moderate" grade was shown in UDCA 1.0%, GDCA 1.0%, CA 1.0%, GCA 2.5-5.0%, TCA 2.5-5.0%, TUDCA 5.0-7.5%, and the remaining various concentrations of bile acids showed edema of "severe" and "extremely severe" (FIGS. 4B to 4K).

TABLE 17

| BA | % (w/v) | Immediately after administration | 1 hour after administration | 2 hours after administration |
|---|---|---|---|---|
| DCA | 1.0 | ++ | +++ | +++ |
| | 2.5 | ++ | ++++ | ++++ |
| | 5.0 | ++ | ++++ | ++++ |
| | 7.5 | ++ | ++++ | ++++ |
| HDCA | 1.0 | ++ | ++ | +++ |
| | 2.5 | ++ | ++ | +++ |
| | 5.0 | ++ | ++++ | ++++ |
| | 7.5 | ++ | ++++ | ++++ |
| UDCA | 1.0 | ++ | ++ | ++ |
| | 2.5 | ++ | +++ | ++++ |
| | 5.0 | ++ | ++++ | ++++ |
| | 7.5 | ++ | ++++ | ++++ |
| TDCA | 1.0 | ++ | +++ | +++ |
| | 2.5 | ++ | +++ | +++ |
| | 5.0 | ++ | ++++ | ++++ |
| | 7.5 | ++ | ++++ | ++++ |
| GDCA | 1.0 | ++ | +++ | ++ |
| | 2.5 | ++ | +++ | +++ |
| | 5.0 | ++ | ++++ | ++++ |
| | 7.5 | ++ | ++++ | ++++ |
| CDCA | 1.0 | ++ | +++ | +++ |
| | 2.5 | ++ | +++ | ++++ |
| | 5.0 | ++ | ++++ | ++++ |
| | 7.5 | ++ | ++++ | ++++ |
| CA | 1.0 | ++ | ++ | ++ |
| | 2.5 | ++ | ++ | +++ |
| | 5.0 | ++ | +++ | ++++ |
| | 7.5 | ++ | ++++ | ++++ |
| GCA | 1.0 | + | + | + |
| | 2.5 | ++ | ++ | ++ |
| | 5.0 | ++ | ++ | ++ |
| | 7.5 | ++ | ++++ | ++++ |
| TCA | 1.0 | ++ | + | + |
| | 2.5 | ++ | ++ | ++ |
| | 5.0 | ++ | ++ | ++ |
| | 7.5 | ++ | +++ | ++++ |
| TUDCA | 1.0 | ++ | + | + |
| | 2.5 | ++ | + | + |
| | 5.0 | ++ | + | ++ |
| | 7.5 | ++ | ++ | ++ |

Figure 4L:
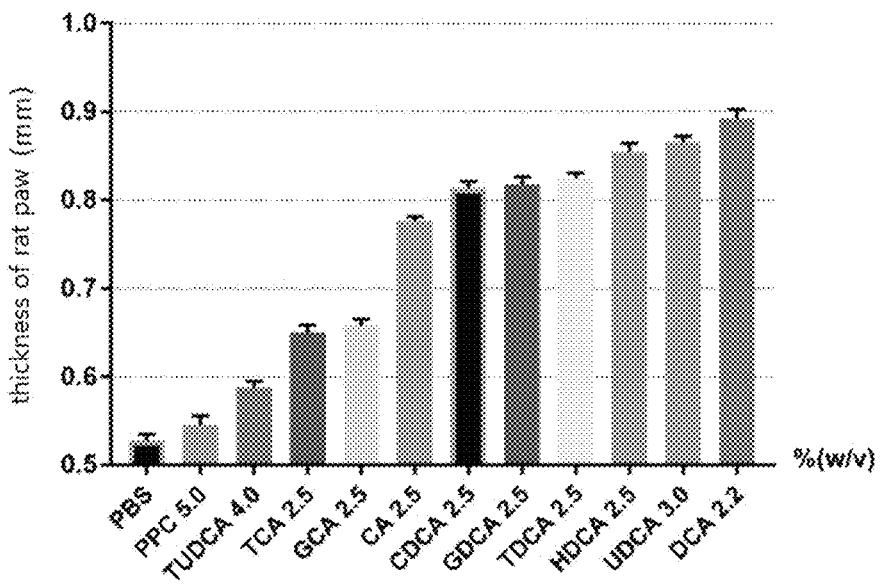
FIG. 4L shows the comparison results of edema at 2 hours after injection of PPC 5.0% single composition and single compositions of bile salts at a concentration need for solubilizing PPC (typically about 2.5%, but 3% for UDCD and 4% for TUDCA is proper).

Specifically, as shown in the results of the in vitro adipocyte viability test described below, PPC 5% showed the ability to reduce adipocyte that is equivalent to that of DCA 1%. Comparing the results based on 2.5% concentration of bile acids that is normally and commonly required to solubilize PPC 5%, the edema degree was "mild" in TUDCA, "moderate" in GCA and TCA, "severe" in HDCA, TDCA, GDCA and CA, and "extremely severe" in DCA, UDCA, CDCA at 2 hours after the administration, as shown in Table 17. FIG. 4L shows the results of comparing edema at 2 hours after the injection of PPC 5.0% single composition, single compositions of each bile acid at a concentration required to solubilize PPC 5.0% (generally about 2.5%, but 3% for UDCA, 4% for TUDCA is proper) or PBS, and the result was similar to the Table 17.

In this regard, in order to confirm the degree of inflammation of PPC complex compositions solubilized with various bile acids, the degree of edema at 2 hours after the administration of the PPC 5.0% complex composition solubilized with each bile acid was compared. As shown in the Table 18, it was confirmed that GCA, TCA and TUDCA showed "no edema", CA showed "moderate" and HDCA, UDCA, TDCA, GDCA and CDCA showed "severe" (FIG. 4M).

TABLE 18

| PPC % (w/v) | BA % (w/v) | Immediately after administration | 1 hour after administration | 2 hours after administration |
|---|---|---|---|---|
| 5.0 | DCA 2.2 | +++ | +++ | +++ |
| 5.0 | HDCA 2.5 | ++ | +++ | +++ |
| 5.0 | UDCA 3.0 | ++ | +++ | +++ |
| 5.0 | TDCA 2.5 | +++ | +++ | +++ |
| 5.0 | GDCA 2.5 | +++ | +++ | +++ |
| 5.0 | CDCA 2.5 | ++ | +++ | +++ |
| 5.0 | CA 2.5 | +++ | +++ | ++ |
| 5.0 | GCA 2.5 | + | − | − |
| 5.0 | TCA 2.5 | + | + | − |
| 5.0 | TUDCA 4.0 | + | + | − |

Figure 4M:
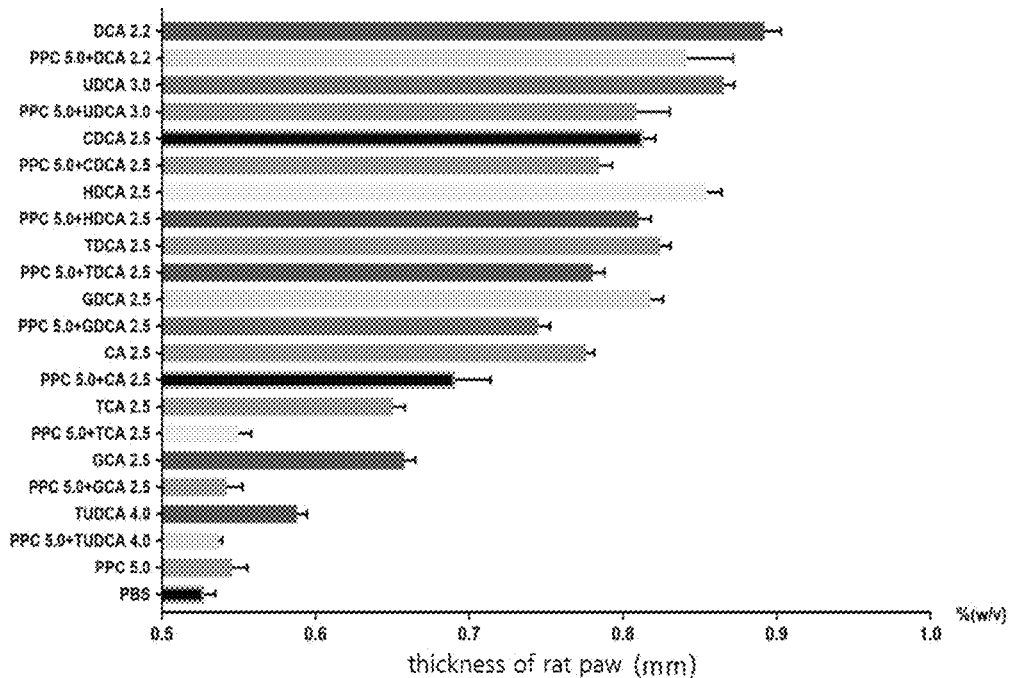
FIG. 4M shows the comparison results of edema at 2 hours after injection of single compositions of bile acids at a concentration need for solubilizing PPC and complex composition of PPC 5.0% solubilized with the above respective bile acids.

A surprising finding was that the degree of edema induced by GCA (2.5%), TCA (2.5%) and TUDCA (5.0%) single compositions was moderate (Table 17), but the degree of edema induced by PPC 5.0% complex composition solubilized with GCA (2.5%), TCA (2.5%) and TUDCA (4.0%) was decreased to no or mild (FIG. 4M).

Figure 4N:
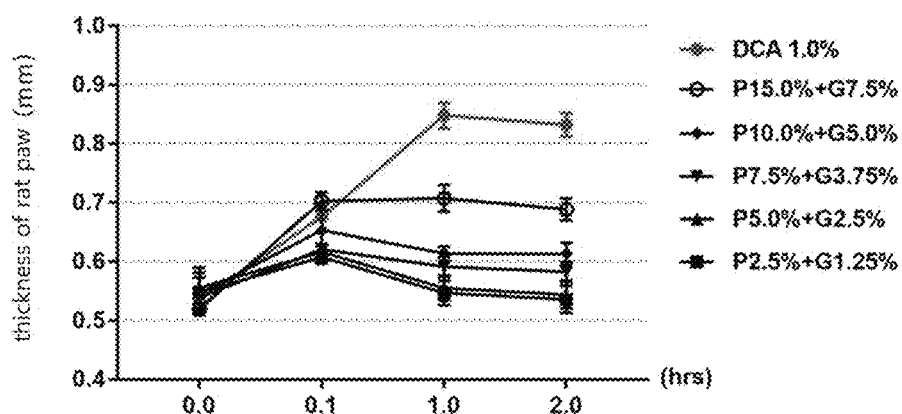
FIG. 4N shows the comparison results of edema after injection of complex composition of PPC (2.5%-15.0%) solubilized with various concentration of GCA (1.25-7.5%) and DCA 1% single composition.
Figure 4O:
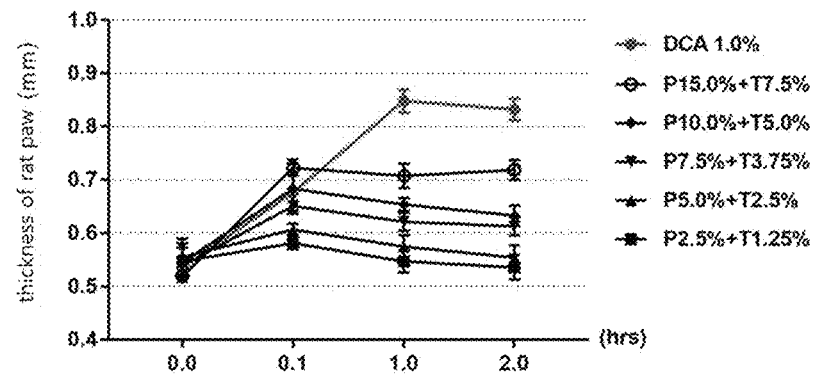
FIG. 4O shows the comparison results of edema after injection of complex composition of PPC (2.5%-15.0%) solubilized with various concentration of TCA (1.25-7.5%) and DCA 1% single composition.

In order to observe edema according to the changes of concentration, time-dependent edema degree of PPC complex compositions solubilized with GCA or TCA was compared. As a result, it was confirmed that the complex compositions corresponding to PPC 2.5-5.0% showed "no edema", the complex compositions corresponding to PPC 7.5-10.0% showed "mild", and the complex compositions corresponding to PPC 15.0% showed "moderate" at 2 hours after the administration, as shown in Table 19 and 20 (FIGS. 4N to 4O).

TABLE 19

| PPC % (w/v) | GCA % (w/v) | Immediately after administration | 1 hour after administration | 2 hours after administration |
|---|---|---|---|---|
| 2.50 | 1.25 | + | − | − |
| 5.00 | 2.50 | + | − | − |
| 7.50 | 3.75 | + | + | + |
| 10.0 | 5.00 | + | + | + |
| 15.0 | 7.50 | ++ | ++ | ++ |

TABLE 20

| PPC % (w/v) | TCA % (w/v) | Immediately after administration | 1 hour after administration | 2 hours after administration |
|---|---|---|---|---|
| 2.50 | 1.25 | + | − | − |
| 5.00 | 2.50 | + | + | − |
| 7.50 | 3.75 | ++ | + | + |
| 10.0 | 5.00 | ++ | + | + |
| 15.0 | 7.50 | ++ | ++ | ++ |

Figure 4P:
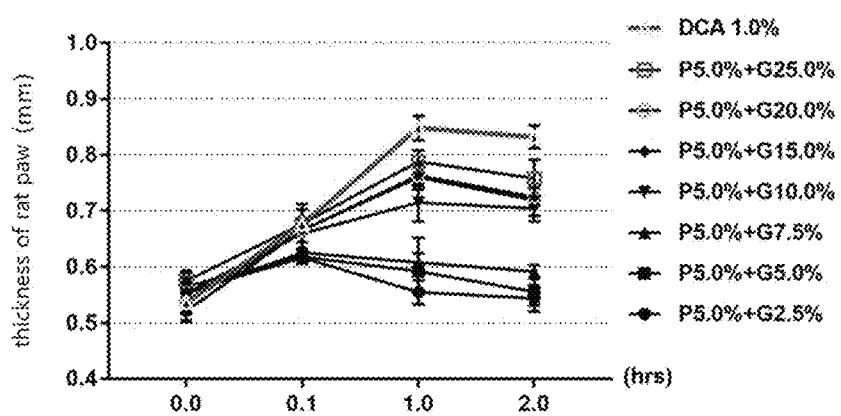
FIG. 4P shows the comparison results of edema after injection of complex composition of PPC 5.0% solubilized with various concentration of GCA (2.5-25%).
Figure 4Q:
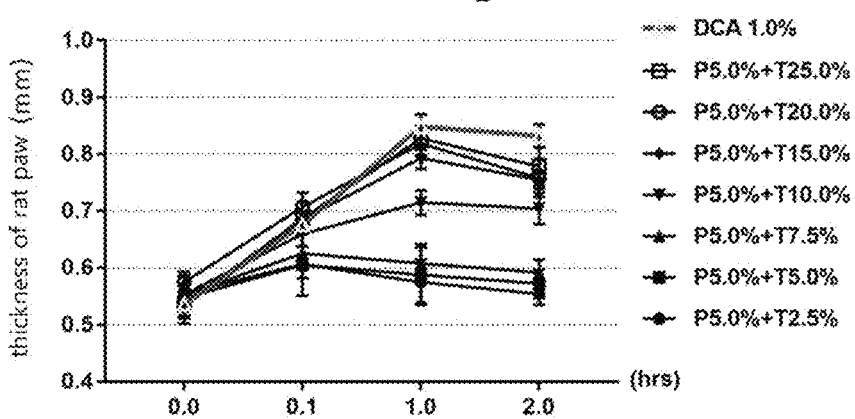

In the PPC complex composition solubilized with bile acids, the preparing time for obtaining a stable clear solution is shortened as the concentration of the bile acids to be added is increased. For this reason, edema was evaluated with compositions in which the concentration of GCA or TCA capable of solubilizing PPC 5.0% is increased. The test materials were complex compositions of PPC 5.0% mixed with 2.5%, 5.0%, 7.5%, 10.0%, 5.0%, 20.0% or 25.0% of GCA or TCA, respectively. As shown in Table 21 and Table 22, the preferred molar ratio of GCA/PPC with no edema or mild edema was 2.60 mol/mol or less, and in the molar ratio of 3.47 mol/mol or less from the above value, edema was mild and moderate, and severe edema was shown in the molar ratio of more than 3.47 mol/mol, In addition, the preferred molar ratio of TCA/PPC with no edema or mild edema was 2.35 mol/mol or less, and in the molar ratio of 3.13 mol/mol or less from the above value, edema was mild and moderate, and severe edema was shown in the molar ratio of more than 3.13 mol/mol (FIGS. 4P and 4Q).

TABLE 21

| PPC % (w/v) | GCA % (w/v) | GCA/PPC molar ratio (mol/mol) | Immediately after administration | 1 hour after administration | 2 hours after administration |
|---|---|---|---|---|---|
| 5.00 | 2.50 | 0.87 | + | − | − |
| | 5.00 | 1.73 | + | + | − |
| | 7.50 | 2.60 | + | + | + |
| | 10.0 | 3.47 | + | ++ | ++ |
| | 15.0 | 5.20 | ++ | +++ | ++ |
| | 20.0 | 6.94 | ++ | +++ | ++ |
| | 25.0 | 8.67 | ++ | ++ | ++ |

TABLE 22

| PPC % (w/v) | TCA % (w/v) | TCA/PPC molar ratio (mol/mol) | Immediately after administration | 1 hour after administration | 2 hours after administration |
|---|---|---|---|---|---|
| 5.00 | 2.50 | 0.78 | + | + | − |
| | 5.00 | 1.57 | + | + | + |

TABLE 22-continued

| PPC % (w/v) | TCA % (w/v) | TCA/PPC molar ratio (mol/mol) | Immediately after administration | 1 hour after administration | 2 hours after administration |
| --- | --- | --- | --- | --- | --- |
| | 7.50 | 2.35 | + | + | + |
| | 10.0 | 3.13 | + | ++ | ++ |
| | 15.0 | 4.70 | ++ | +++ | +++ |
| | 20.0 | 6.26 | ++ | +++ | ++ |
| | 25.0 | 7.83 | ++ | +++ | +++ |

Taken together the results of in vivo edema test, PPC 1.25-10.0% single composition showed "mild" edema at 2 hours after the administration, when the edema was the most severe, as shown in Table 16 to 22 and FIG. 4 (FIG. 4A to 4Q). Of the bile acids (BA) selected to solve the limitation of industrial use due to low formulation stability of PPC single composition, DCA 2.5%, UDCA 2.5%, CDCA 2.5%, HDCA 2.5%, TDCA 2.5%, GDCA 2.5% and CA 2.5% showed "severe" and "extremely severe" edema, and GCA 2.5%, TCA 2.5% and TUDCA 5.0% showed "moderate" edema. But, PPC 5.0% complex composition solubilized with GCA, TCA or TUDCA showed "no" or "mild" edema. As a result of observation of edema changes according to the concentrations and mixing amount, the PPC 2.5-10.0% complex composition solubilized with 1.25-5.0% of GCA or TCA showed "no" or "mild" edema. GCA/PPC molar ratio of 3.47 mol/mol or less, preferably 2.60 mol/mol or less, and TCA/PPC molar ratio of 3.13 mol/mol or less, preferably 2.35 mol/mol or less showed "no" or "mild" edema. According to the results of previous studies and in vitro results of adipocyte viability test (see Test 2 described below) TUDCA was found to be not a suitable solubilizing agent due to the effect of inhibiting the apoptosis, which is the adipocyte lysis mechanism of PPC.

1-2: Measurement of Skin Lesion (Erythema)

In order to observe harmful cases related to skin after injection of the test compositions, skin lesions were observed by photographing the sole of the rat paws (using a 4 cm×4 cm scale) when measuring the paw thickness in the Test Example 1-1. The grades of skin lesion were evaluated as 0 to 4 grades. The grades of skin lesion immediately after injection, and 1 or 2 hours after the injection was evaluated compared to before the injection in which the grades were defined as no erythema (−), very slight erythema [(barely identifiable visually), mild (+)], marked erythema (moderate, ++), slightly severe erythema (severe, +++), and severe erythema (extremely severe, ++++).

Figure 5A:
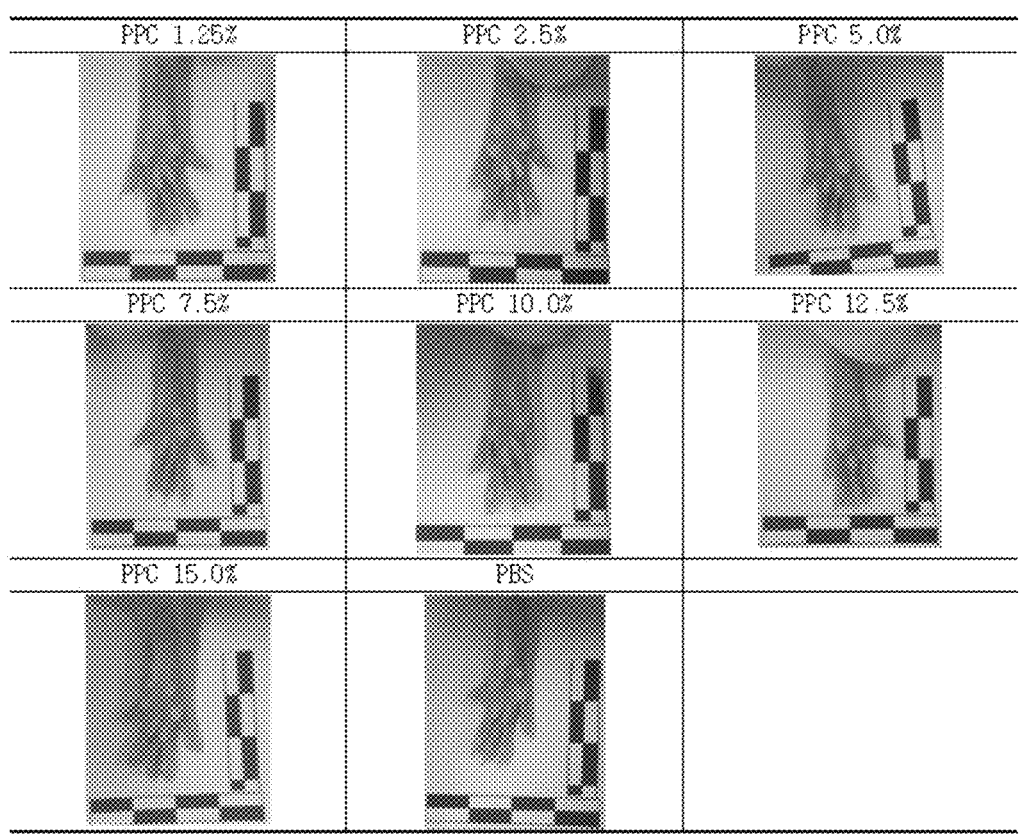
FIGS. 5A to 5F show a series of images of site of administration, wherein the images were taken at 2 hours after injecting 1.0 ml of PPC (1.25-15.0%) single composition and PBS (FIG. 5A), single compositions of various kinds of bile salts (DCA, HDCA, UDCA, TDCA, GDCA, CDCA, CA, GCA, TCA and TUDCA) at concentrations of 1.0-7.5% (FIGS. 5B and 5C), PPC 5.0% complex compositions solubilized with various kind of bile salts (FIG. 5D), PPC (2.5-15.0%) complex compositions solubilized with GCA (1.25-7.5%)(FIG. 5E) or PPC (5.0%) complex compositions solubilized with GCA (2.5-20.0%)(FIG. 5F) to the paws of rats. The paw images were taken using a 4×4 cm scale.

Firstly, there was no erythema at all in all concentration groups of PPC (1.25-15.0%) single composition as shown in the Table 23 (FIG. 5A).

TABLE 23

| PPC % (w/v) | Immediately after administration | 1 hour after administration | 2 hours after administration |
| --- | --- | --- | --- |
| 1.25 | − | − | − |
| 2.50 | − | − | − |
| 5.00 | − | − | − |
| 7.50 | − | − | − |
| 10.0 | − | − | − |
| 12.5 | − | − | − |
| 15.0 | − | − | − |

Figure 5B:
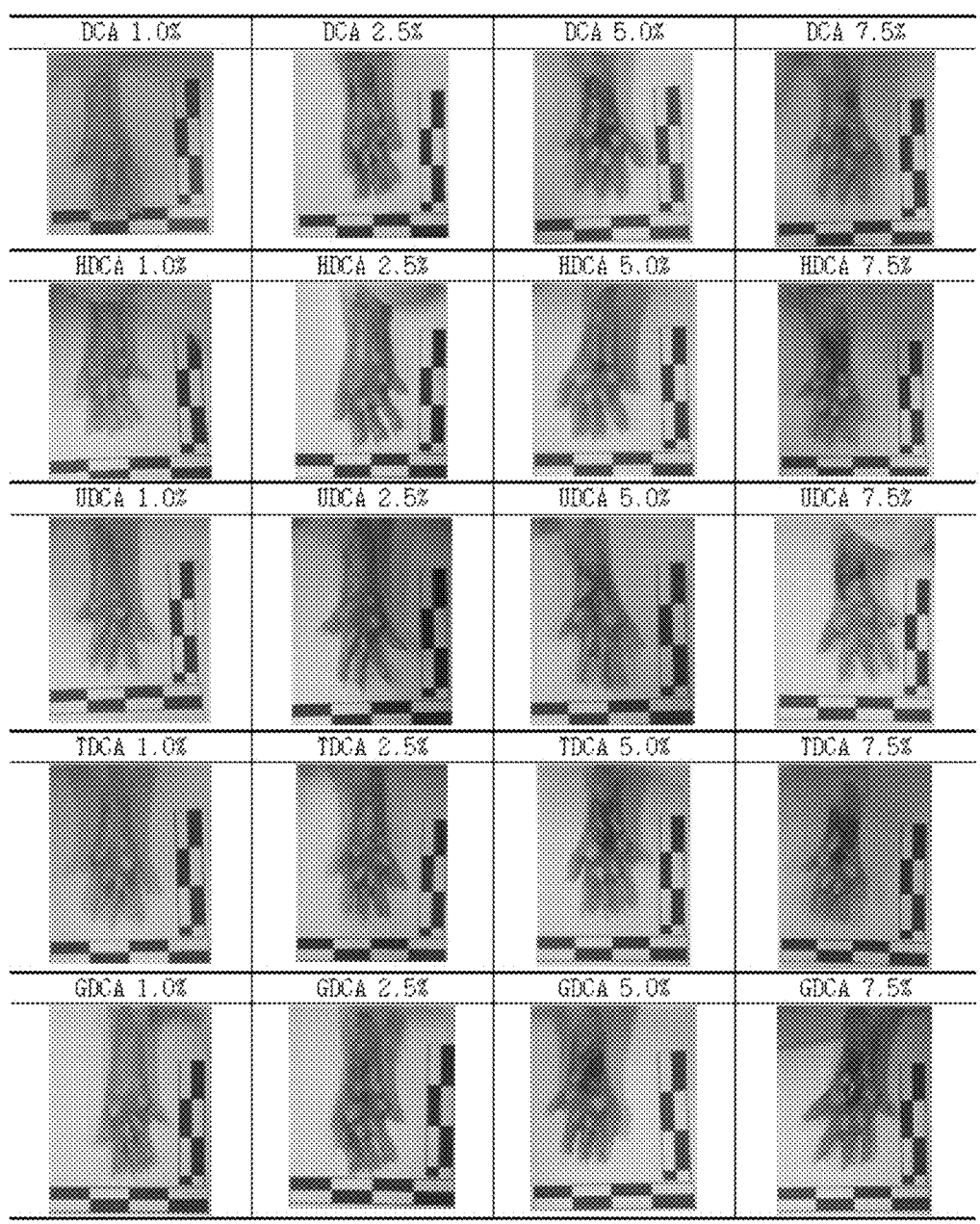
Figure 5C:
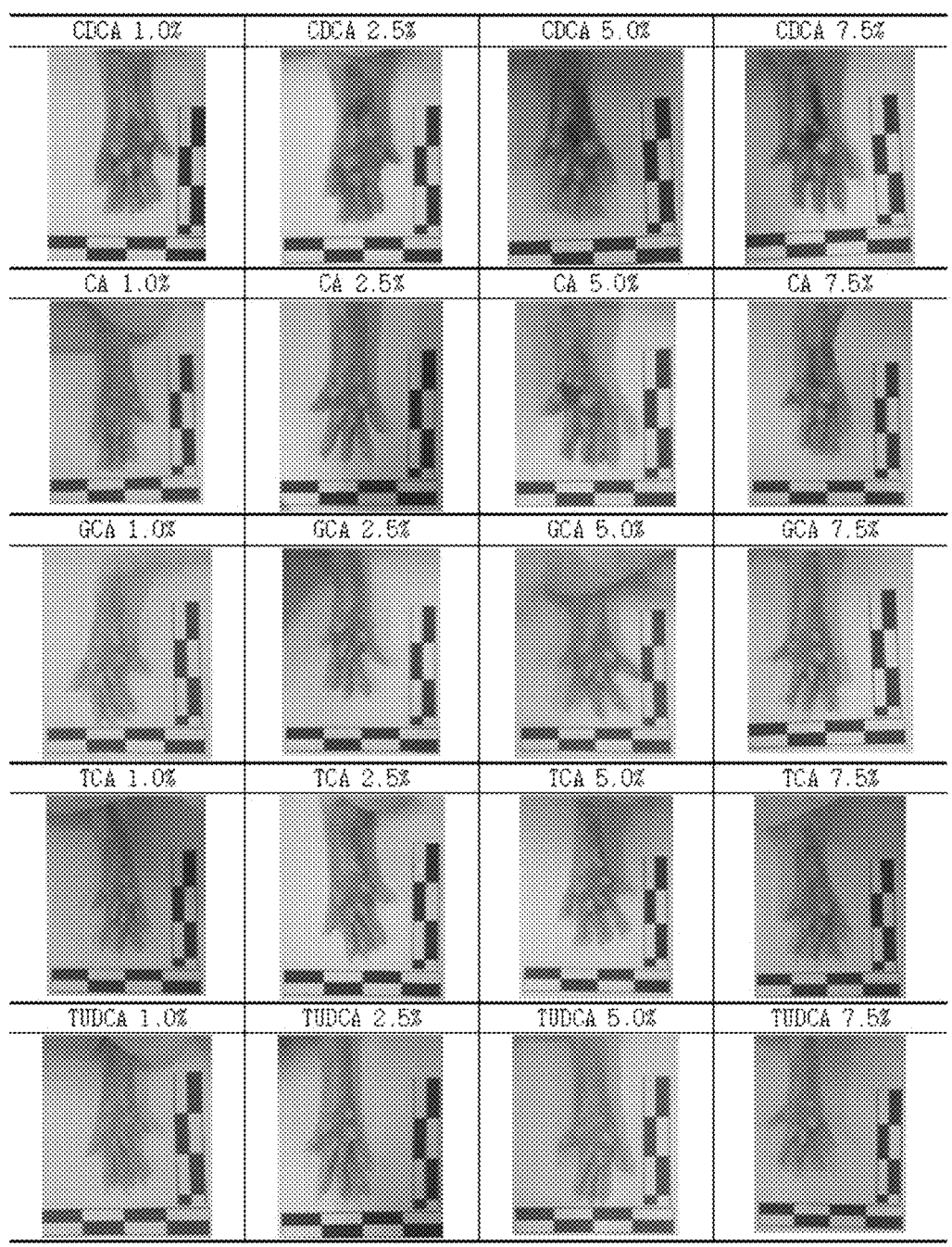

Next, the results of skin lesion of the single compositions of various concentrations (BA 1.0%, 2.5%, 5.0% and 7.5%) were as shown in Table 24 that 2.5% or more of DCA, HDCA, UDCA, GDCA, TDCA and CDCA, and 5.0% or more of CA showed severe and extremely severe erythema. And it was confirmed that 5.0% or less of GCA and TCA showed no or mild erythema, and TUDCA showed no erythema (FIGS. 5B and 5C).

TABLE 24

| BA | % (w/v) | Immediately after administration | 1 hour after administration | 2 hours after administration |
| --- | --- | --- | --- | --- |
| DCA | 1.0 | ++ | ++ | ++ |
| | 2.5 | ++ | ++++ | +++ |
| | 5.0 | ++ | ++++ | ++++ |
| | 7.5 | ++ | ++++ | ++++ |
| HDCA | 1.0 | + | + | + |
| | 2.5 | + | +++ | +++ |
| | 5.0 | + | ++++ | ++++ |
| | 7.5 | ++ | ++++ | ++++ |
| UDCA | 1.0 | + | ++ | ++ |
| | 2.5 | ++ | ++ | +++ |
| | 5.0 | ++ | ++++ | ++++ |
| | 7.5 | ++ | ++++ | ++++ |
| TDCA | 1.0 | + | +++ | ++ |
| | 2.5 | ++ | +++ | +++ |
| | 5.0 | ++ | ++++ | ++++ |
| | 7.5 | ++ | ++++ | ++++ |
| GDCA | 1.0 | ++ | ++ | ++ |
| | 2.5 | ++ | ++++ | ++++ |
| | 5.0 | ++ | ++++ | ++++ |
| | 7.5 | ++ | ++++ | ++++ |
| CDCA | 1.0 | + | ++ | ++ |
| | 2.5 | ++ | ++++ | ++++ |
| | 5.0 | ++ | ++++ | ++++ |
| | 7.5 | ++ | ++++ | ++++ |
| CA | 1.0 | − | + | + |
| | 2.5 | − | ++ | ++ |
| | 5.0 | ++ | +++ | +++ |
| | 7.5 | ++ | ++++ | ++++ |
| GCA | 1.0 | − | − | − |
| | 2.5 | + | + | + |
| | 5.0 | + | + | + |
| | 7.5 | + | ++ | ++ |
| TCA | 1.0 | − | − | − |
| | 2.5 | + | + | + |
| | 5.0 | + | + | + |
| | 7.5 | + | ++ | ++ |
| TUDCA | 1.0 | − | − | − |
| | 2.5 | − | − | − |
| | 5.0 | − | − | − |
| | 7.5 | − | − | − |

Figure 5D:
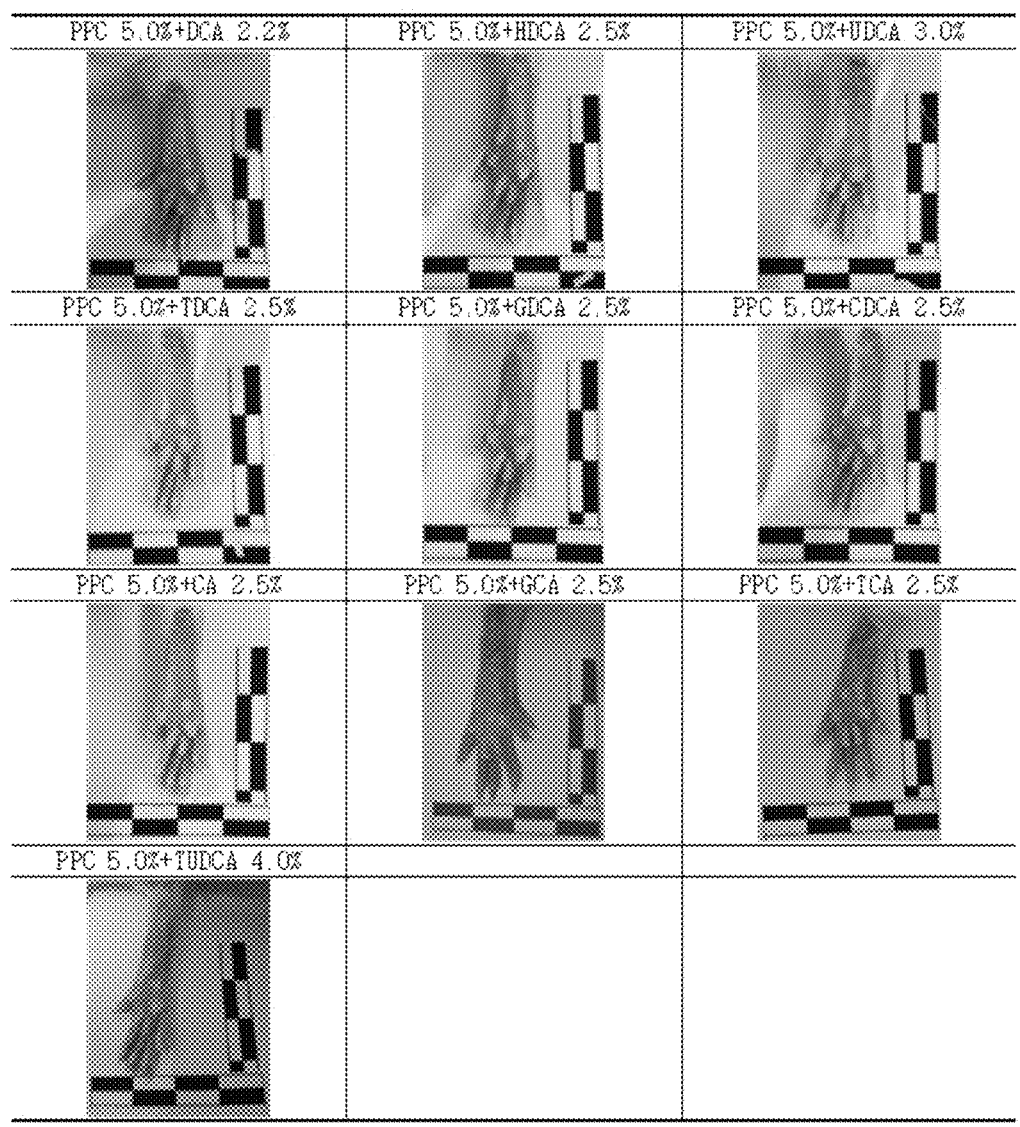

The skin lesion results of PPC 5.0% complex compositions solubilized with various bile acids were as shown in Table 25 that PPC 5.0% complex composition solubilized with DCA, HDCA, UDCA or CDCA showed severe erythema, PPC 5.0% complex composition solubilized with TDCA, GDCA or CA showed moderate erythema, and PPC 5.0% complex composition solubilized with GCA, TCA and TUDCA showed no erythema at 2 hours after the administration (FIG. 5D).

TABLE 25

| PPC % (w/v) | BA % (w/v) | Immediately after administration | 1 hour after administration | 2 hours after administration |
|---|---|---|---|---|
| 5.0 | DCA 2.2 | + | +++ | +++ |
| 5.0 | HDCA 2.5 | + | +++ | +++ |
| 5.0 | UDCA 3.0 | + | +++ | +++ |
| 5.0 | TDCA 2.5 | + | ++ | ++ |
| 5.0 | GDCA 2.5 | + | ++ | ++ |
| 5.0 | CDCA 2.5 | + | +++ | +++ |
| 5.0 | CA 2.5 | − | ++ | ++ |
| 5.0 | GCA 2.5 | − | − | − |
| 5.0 | TCA 2.5 | − | − | − |
| 5.0 | TUDCA 4.0 | − | − | − |

Figure 5E:
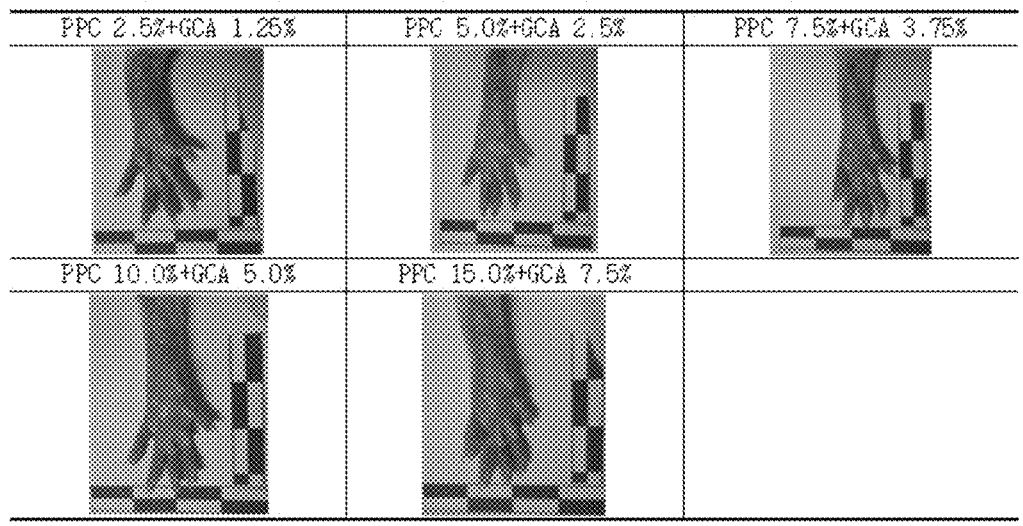

In order to observe the lesion according to the concentration change, the degree of lesion was compared with various concentrations of the PPC complex composition solubilized with GCA. As shown in Table 26, lesions were not observed in PPC 10.0%+GCA 5.0% or less, and mild lesions were observed in PPC 15.0%+GCA 7.5% (FIG. 5E).

TABLE 26

| PPC % (w/v) | GCA % (w/v) | Immediately after administration | 1 hour after administration | 2 hours after administration |
|---|---|---|---|---|
| 2.50 | 1.25 | − | − | − |
| 5.00 | 2.50 | − | − | − |
| 7.50 | 3.75 | − | − | − |
| 10.0 | 5.00 | − | − | − |
| 15.0 | 7.50 | + | + | + |

Figure 5F:
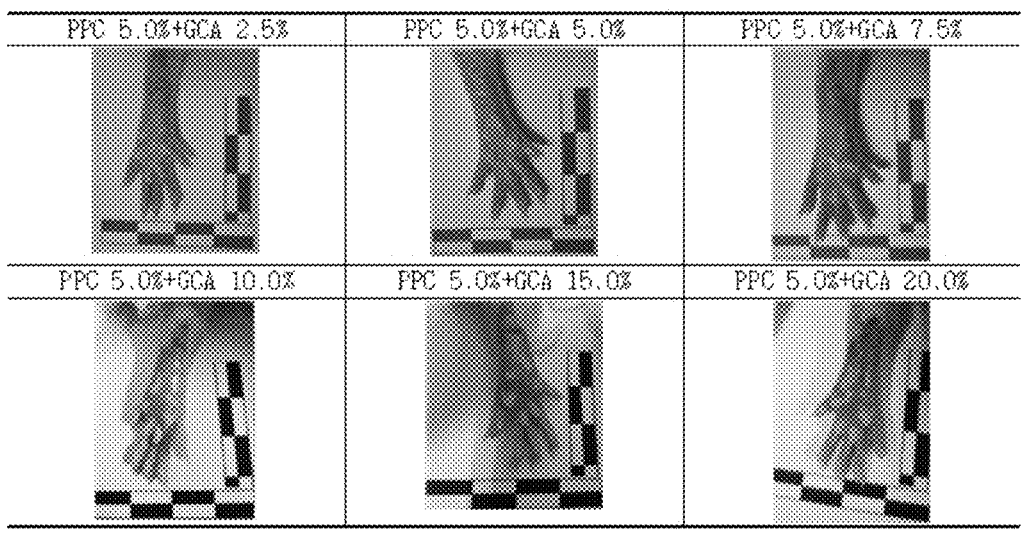

The lesions were evaluated for compositions of increased concentration of GCA capable of solubilize PPC 5.0%. As shown in Table 27, the preferable molar ratio of GCA/PPC without lesion or mild was 2.60 mol/mol or less, and the lesion was severe or extremely severe at a molar ratio of 3.47 mol/mol or more (FIG. 5F).

TABLE 27

| PPC % (w/v) | GCA % (w/v) | GCA/PPC molar ratio (mol/mol) | Immediately after administration | 1 hour after administration | 2 hours after administration |
|---|---|---|---|---|---|
| 5.00 | 2.50 | 0.87 | − | − | − |
|  | 5.00 | 1.73 | − | − | − |
|  | 7.50 | 2.60 | − | + | + |
|  | 10.0 | 3.47 | + | +++ | +++ |
|  | 15.0 | 5.20 | +++ | ++++ | ++++ |
|  | 20.0 | 6.94 | +++ | ++++ | ++++ |
|  | 25.0 | 8.67 | ++++ | ++++ | ++++ |

Taken together the results of in vivo lesion test, as shown in Table 23 to 27 and FIG. 5, PPC 1.25-10.0% single composition showed no lesion. Of the bile acids (BA) selected to solve the limitation of industrial use due to low formulation stability of PPC single composition, DCA 2.5%, UDCA 2.5%, CDCA 2.5%, HDCA 2.5%, TDCA 2.5%, GDCA 2.5% and CA 5.0% or more showed "severe" and "extremely severe" lesion, and 5.0% or less of GCA and TCA showed no or mild lesion, and TUDCA showed no lesion. In case of the PPC 5.0% complex compositions solubilized with additional bile acids, PPC 5.0% complex compositions solubilized with DCA, HDCA, UDCA or CDCA showed severe lesion, PPC 5.0% complex compositions solubilized with TDCA, GDCA or CA showed moderate lesion, but PPC 5.0% complex compositions solubilized with GCA, TCA or TUDCA showed no lesion. As the results of the lesion changes according to the concentration and mixing amount, PPC 2.5-10.0% complex composition solubilized with GCA 1.25-5.0% showed no lesion, PPC 15.0% complex composition solubilized with GCA 7.5% showed mild lesion. In addition, it was confirmed that GCA/PPC molar ratio of 2.60 mol/mol or less showed no or mild lesion.

1-3: The H&E Staining Histological Test (Inflammation)

The rats were sacrificed at 3 hours after completion of the Test Examples 1-1 and 1-2 to evaluate the degree of inflammation after injection of the test compositions. The tissues of the injected area were dissected, fixed with 10% formalin, and then the specimen was prepared and images were captured using an optical microscope. The degree of inflammation was evaluated as follows.

The no inflammation (−) indicates that the functional tissues such as sweat glands, blood vessels, and adipose tissue are well maintained and the inflammatory cells are not visible. Mild (+) indicates that the form of functional tissues (sweat glands, blood vessels, adipose tissue, etc.) are well maintained and infrequently inflammatory cells appear. Moderate (++) indicates that the morphology of functional tissues (sweat glands, blood vessels, adipose tissue, etc.) is impaired and inflammatory cells appear in tissues. Severe (+++) indicates that the morphology of functional tissues is impaired and inflammatory cells are increased, and inflammatory cells such as neutrophils, mononuclear cells, and the like migrate to tissues around the blood vessels. Extremely severe (+++) indicates that the morphology of the functional tissue is impaired by edema and inflammation, and the inflammatory cells such as neutrophils, mononuclear cells, and the like are not only increased but also spread to the papillary dermis, and the tissue damage is obviously observed.

Figure 6A:
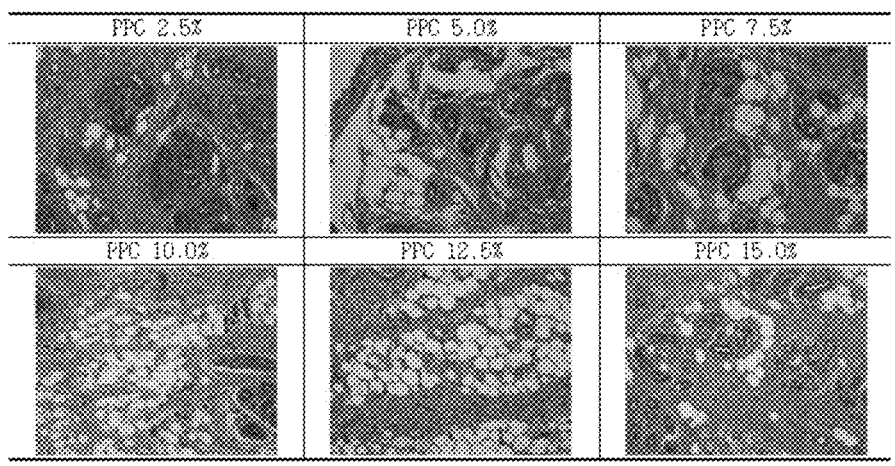

Firstly, as results of inflammation evaluation for all the concentrations of PPC (1.25-15.0%) single compositions, PPC 2.50-7.50% showed "no" inflammation, PPC 10.0-12.5% showed "mild", and PPC 15.0% showed "moderate", as shown in following Table 28 (FIG. 6A).

TABLE 28

| PPC % (w/v) | GCA % (w/v) | GCA/PPC molar ratio (mol/mol) | Inflammation reaction | PPC (w/v) % | BA (w/v) % | Inflammation reaction |
|---|---|---|---|---|---|---|
| 2.50 | 0.0 | | − | 5.0 | DCA 2.2 | ++++ |
| 5.00 | 0.0 | | − | | HDCA 2.5 | ++++ |
| 7.50 | 0.0 | | − | | UDCA 3.0 | ++++ |
| 10.0 | 0.0 | | + | | TDCA 2.5 | +++ |
| 12.5 | 0.0 | | + | | GDCA 2.5 | +++ |
| 15.0 | 0.0 | | ++ | | CDCA 2.5 | ++++ |
| 2.50 | 1.25 | 0.87 | − | | CA 2.5 | ++ |
| 5.00 | 2.50 | | − | | GCA 2.5 | − |
| 7.50 | 3.75 | | − | | TCA 2.5 | − |
| 10.0 | 5.00 | | + | | TUDCA 4.0 | − |
| 15.0 | 7.50 | | ++ | | | |
| 5.0 | 2.5 | 0.87 | − | | | |
| | 5.0 | 1.73 | − | | | |
| | 7.5 | 2.60 | − | | | |
| | 10.0 | 3.47 | + | | | |
| | 15.0 | 5.20 | ++++ | | | |
| | 20.0 | 6.94 | ++++ | | | |
| | 25.0 | 8.67 | ++++ | | | |

Figure 6B:
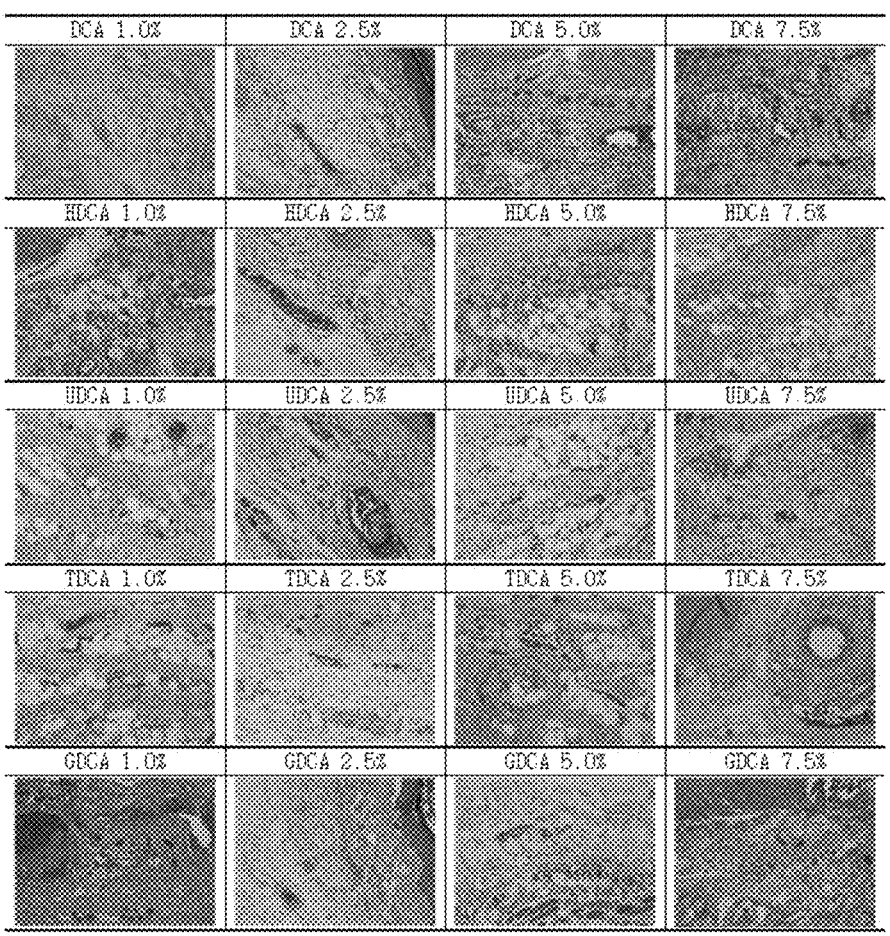
Figure 6C:
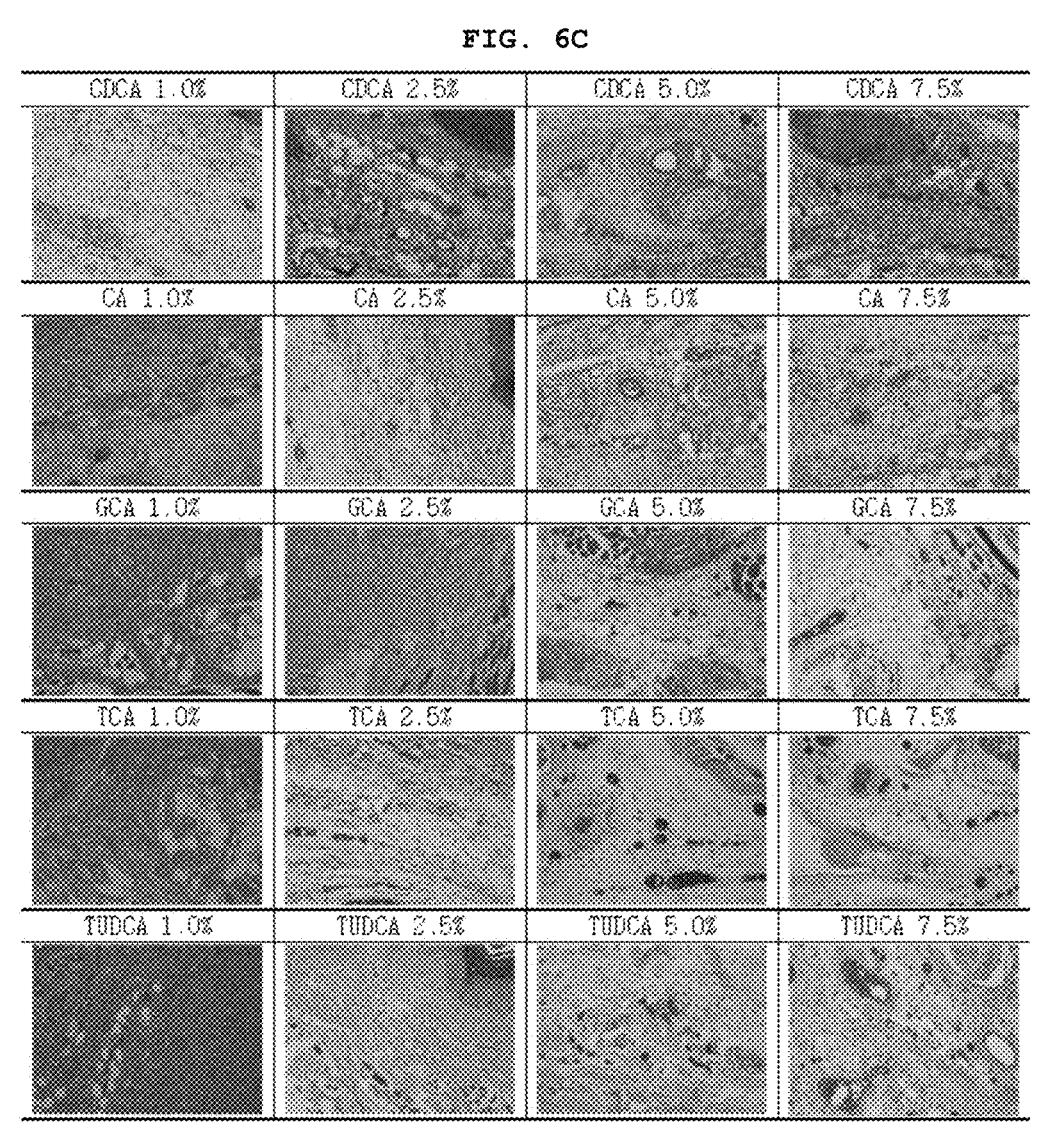

Next, as results of inflammation evaluation for bile acids of various concentrations (BA 1.0%, 2.5%, 5.0% and 7.5%), 1.0% or more of DCA, HDCA and UDCA showed severe and extremely severe inflammation, 2.5% or more of TDCA, GDCA, CDCA and CA showed severe and extremely severe inflammation. And 2.5% or more of GCA and TCA showed moderate inflammation, and high concentration of TUDCA only showed mild inflammation (FIGS. 6B and 6C).

TABLE 29

| | BA % (w/v) | | | |
|---|---|---|---|---|
| | 1.0 | 2.5 | 5.0 | 7.5 |
| DCA | +++ | ++++ | ++++ | ++++ |
| HDCA | +++ | ++++ | ++++ | ++++ |
| UDCA | +++ | ++++ | ++++ | ++++ |
| TDCA | ++ | ++++ | ++++ | ++++ |
| GDCA | ++ | +++ | ++++ | ++++ |
| CDCA | ++ | +++ | +++ | ++++ |
| CA | ++ | +++ | ++++ | ++++ |
| GCA | + | ++ | ++ | ++ |
| TCA | + | ++ | ++ | ++ |
| TUDCA | − | − | − | + |

In order to test the degree of inflammation of PPC complex compositions solubilized with bile acids, PPC 5.0% complex compositions solubilized with various bile acids were prepared and inflammation was measured. As shown in the Table 29, the PPC complex compositions solubilized with DCA, HDCA UDCA or CDCA showed "extremely severe", the PPC complex compositions solubilized with TDCA or GDCA showed "severe", and the PPC complex composition solubilized with CA showed "moderate". On the other hand, the PPC complex composition solubilized with GCA, TCA or TUDCA uniquely showed no inflammation. And it was surprising findings that the GCA 2.5% and TCA 2.5% single composition showed moderate inflammation, but the PPC 5.0% complex compositions solubilized with GCA 2.5% or TCA 2.5% showed no inflammation (FIG. 6D).

Figure 6E:
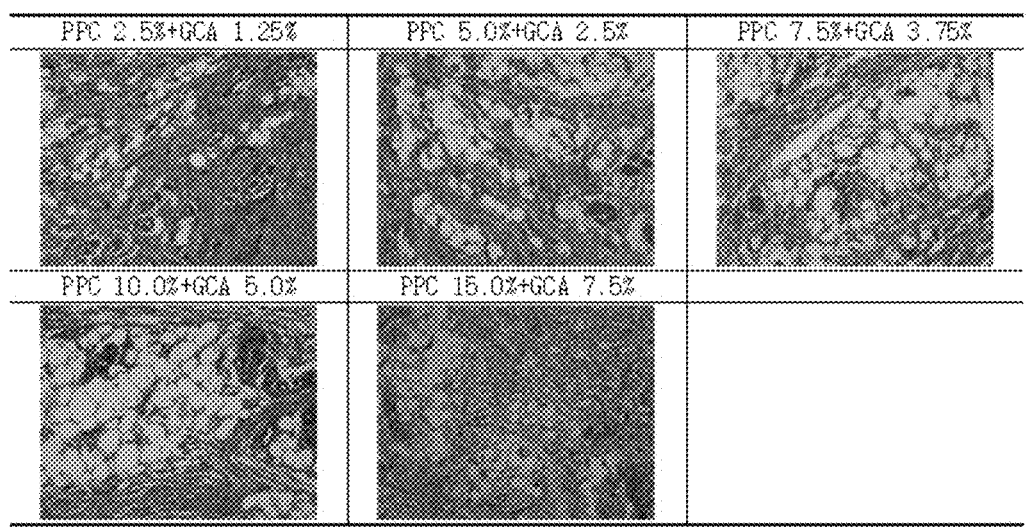

In order to examine the degree of inflammation according to the concentration change, the degree of inflammation of various PPC complex compositions solubilized with GCA was compared. As a result, PPC 7.5%+GCA 3.75% or less showed "no" inflammation, PPC 10.0%+GCA 5.0% showed mild inflammation, and PPC 15.0%+GCA 7.50% showed moderate inflammation (FIG. 6E).

Figure 6F:
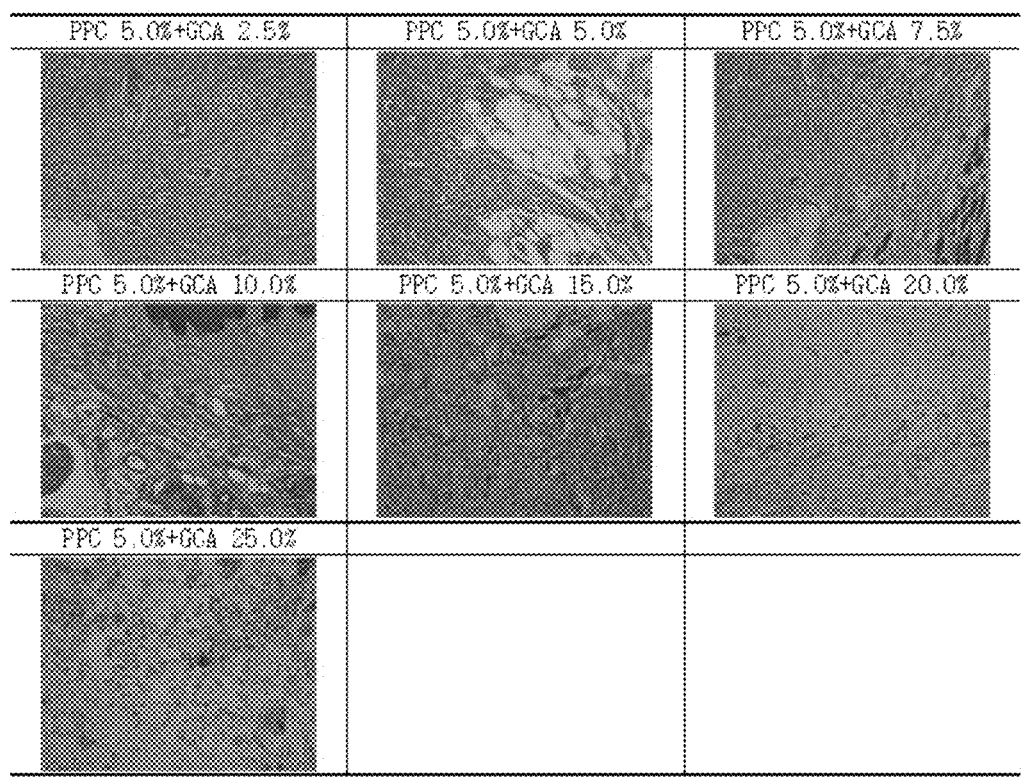

In order to examine the degree of inflammation according to the increase in the mixing amount of solubilizing agent, compositions comprising increased concentration of GCA capable of solubilizing PPC 5.0% were prepared and inflammation was evaluated. As shown in the Table. 28, the preferable molar ratio of GCA/PPC which show no or mild inflammation was 3.47 mol/mol or less, and it was confirmed that molar ratio of 3.47 mol/mol or more showed extremely severe inflammation (FIG. 6F).

The summary of the in vivo test results of edema, lesion and inflammation caused by subcutaneous injection for reducing localized fat is as follows. In order to prepare PPC 5.0%, which has an equivalent adipocyte reducing efficacy to DCA 1.0%, as a stable composition, bile acids should be mixed at a concentration of 2.5% in general, but it was confirmed that DCA, HDCA, UDCA, TDCA, GDCA, CDCA and CA caused severe and extremely severe edema and lesion caused by inflammation at 2.5% concentration. In addition, PPC 5.0% complex compositions formulated with the above-mentioned bile acids induced significant pain and edema. Therefore, those bile acids were not suitable as solubilizing agents to be incorporated in the PPC-based localized fat reducing injectable composition of the present invention. On the other hand, GCA+PPC preparations and TCA+PPC preparations didn't cause pain, edema and lesions, and these findings were incredible findings that were unpredictable from the PPC, GCA or TCA single composition.

In summary, it was found that the GCA+PPC complex preparations and the TCA+PPC complex preparations of the present invention preferably have a molar ratio of bile acid to PPC (that is, GCA/PPC molar ratio or TCA/PPC molar ratio) of 0.7 to 3.0. When the molar ratio (mol/mol) was less than 0.7, the formulation stability decreased because the formation of stable micelles was difficult. Therefore, it is preferable to have a molar ratio of at least 0.7 or more, more preferably, when the molar ratio is 0.76 or more, it is the most advantageous in terms of stability and process time. When the molar ratio exceeded 3.04, the side effects such as inflammation, edema and skin lesions were considerably induced, and the possibility of necrosis was increased rather than giving a positive effect on adipocyte apoptosis and lipolysis. At a molar ratio of 3.0 or less, such side effects and pain were significantly reduced. In particular, when the molar ratio was 2.60 or less within the above range, the side effects and the pain were reduced to substantially no such side effects and pain. Most preferably, when the molar ratio was 1.73 or less, it is confirmed that an excellent fat-reducing composition free from all of inflammation, edema and lesion was produced. The results of the confirmation of the pain are further described in the following test examples.

In addition, it was confirmed to be more advantageous in terms of pain, edema and side effects that the absolute content of PPC may preferably be 12.5% (w/v) or less, and more preferably 10.0% (w/v) or less in the total composition.

Test Example 2: The Comparison of Cell Reducing Effect 2-1: The Comparison of Adipocyte (3T3-L1) Reducing Effect Tests were performed to compare the adipocyte reducing activity of the PPC single composition and the PPC composition solubilized with bile acids. Differentiated 3T3L-1 adipocyte lines were used to observe adipocyte reduction activity, and cell viability was monitored by MTT assay. The following results were obtained by comparing the adipocyte viability for each test materials. Specifically, the mixed composition of TUDCA, GCA or TCA, which were solubilizing agent selected from the in vivo test results, with PPC affected adipocyte viability in the following in vitro test result with unexpected mixing ratio, and the following data demonstrate such unexpected discovery. Materials and methods employed in the following experiments are described below. In the following, % of the composition refers to % (w/v).

The specific test methods are as follows. Differentiated 3T3-L1 adipocytes were cultured at 85-92% cell confluence. The cells were treated with each of the following test compositions and cultured at 37° C. for 0 to 96 hours: PPC single composition (PPC 0.3125%, 0.625%, 1.25%, 2.5%, 5.0%, 7.5%, 10.0%, 15.0%), DCA single composition (DCA 1.0%, 1.1%, 2.2%), GCA single composition (GCA 1.25%, 2.5%, 5.0%), PPC complex composition solubilized with GCA (PPC 0.3125%+GCA 0.1563%, PPC 0.625%+GCA 0.3125%, PPC 1.25%+GCA 0.625%, PPC 2.5%+GCA 1.25%, PPC 5.0%+GCA 2.5%, PPC 7.5%+GCA 3.75%, PPC 10.0%+GCA 5.0%, PPC 15.0%+GCA 7.5%, PPC 5.0%+GCA, 3.75%, PPC 5.0%+GCA 5.0%, PPC 5.0%+GCA 6.25%, PPC 5.0%+GCA 7.5%, PPC 5.0%+GCA 8.75%), PPC complex composition solubilized with TCA (PPC 0.3125%+TCA 0.1563%, PPC 0.625%+TCA 0.3125%, PPC 1.25%+TCA 0.625%, PPC 2.5%+TCA 1.25%, PPC 5.0%+TCA 2.5%, PPC 7.5%+TCA 3.75%, PPC 10.0%+TCA 5.0%, PPC 15.0%+TCA 7.5%), PPC complex composition solubilized with TUDCA (PPC 0.3125%+TUDCA 0.25%, PPC 0.625%+TUDCA 0.5%, PPC 1.25%+TUDCA 1.0%, PPC 2.5%+TUDCA 2.0%, PPC 5.0%+TUDCA 4.0%, PPC 7.5%+TUDCA 6.0%, PPC 10.0%+TUDCA 8.0%, PPC 15.0%+TUDCA 12.0%), PPC complex composition solubilized with DCA (PPC 2.5%+DCA 1.1%, PPC 5.0%+DCA 2.2%, PPC 10.0%+DCA 4.4%) or PPC complex composition solubilized with other bile acids (PPC 5.0%+HDCA 2.5%, PPC 5.0%+UDCA 3.0%, PPC 5.0%+TDCA 2.5%, PPC 5.0%+GDCA 2.5%, PPC 5.0%+CDCA 2.5%, PPC 5.0%+CA 2.5%). The cells were washed twice with PBS, treated with MTT reagent (50 μl) and left at 37° C. for 2 hours. After removing the supernatant, MTT formazan crystals were dissolved in DMSO and the absorbance was measured at 540 nm using a microplate reader.

As a result, as shown in FIGS. 7A to 7D, the PPC single composition and the PPC+GCA complex composition exhibited similar adipocyte-reducing activity in a time and concentration-dependent manner. And the PPC+TCA composition showed lower adipocyte reducing effect than PPC single and PPC+GCA composition at the same concentration. However, treatment with PPC+TUDCA composition did not decrease adipocyte viability (FIGS. 7A to 7D).

Figure 7A:
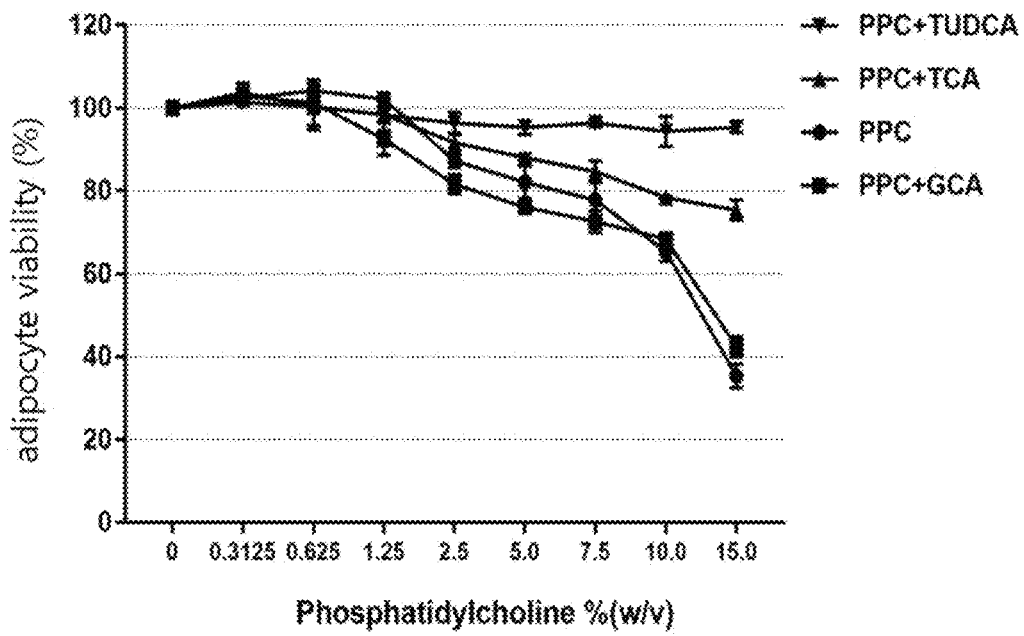
FIGS. 7A to 7I show a series of images demonstrating the decrease in viability of 3T3-L1 adipocytes treated with the test materials. Adipocyte viability was measured by 3-(4,5-dimethyltazol-2-yl)-2,5-diphenyltetrazolium bromide (MTT) assay. The experiment was repeated 3 times per treatment and the results were expressed as the total percentage of viable cells versus untreated control. At 24 hours (FIG. 7A), 48 hours (FIG. 7B), 72 hours (FIG. 7C) and 96 hours (FIG. 7D) after treatment of PPC (0.3125-15.0%) single composition, PPC (0.3125-15.0%) complex composition solubilized with TUDCA (0.25-12.0%), PPC (0.3125-15.0%) complex composition solubilized with TCA (0.1563-7.5%) or PPC (0.3125-15.0%) complex composition solubilized with GCA (0.1563-7.5%) into differentiated 3T3-L1 adipocytes, the adipocyte viability was measured.
Figure 7B:
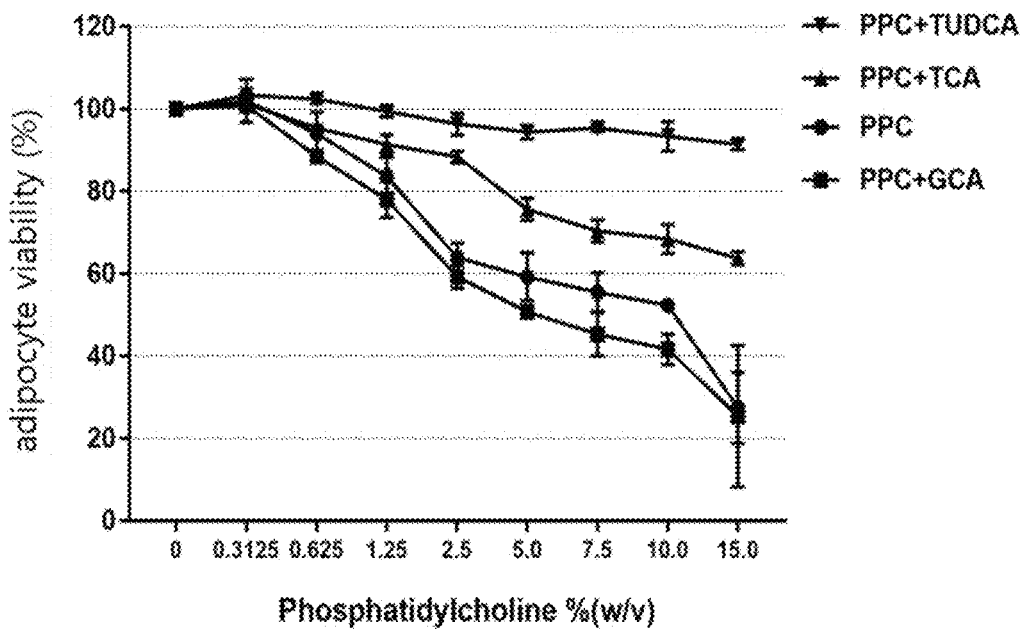
Figure 7C:
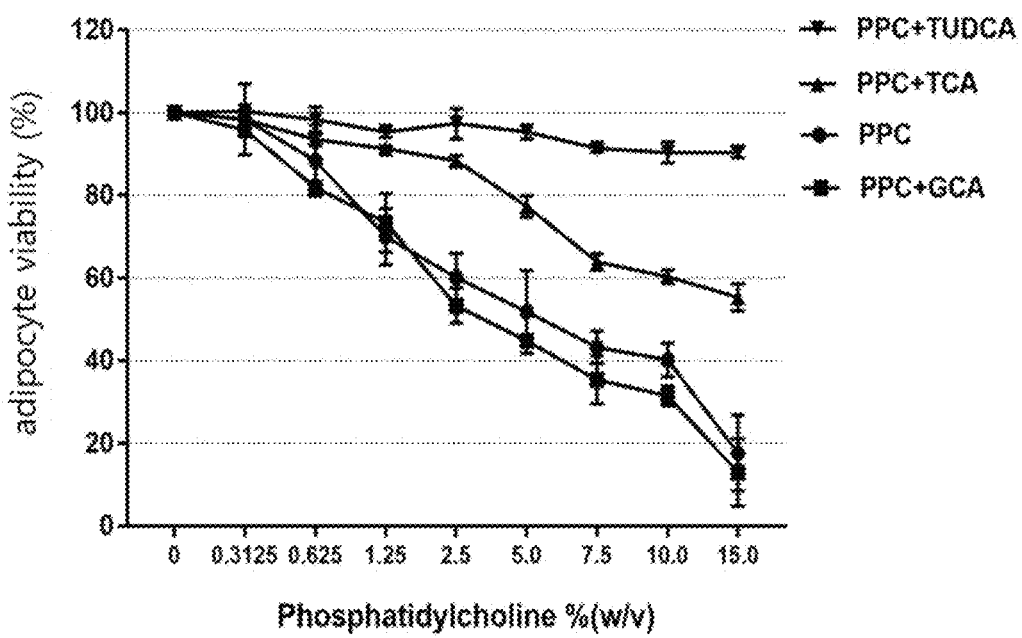
Figure 7D:
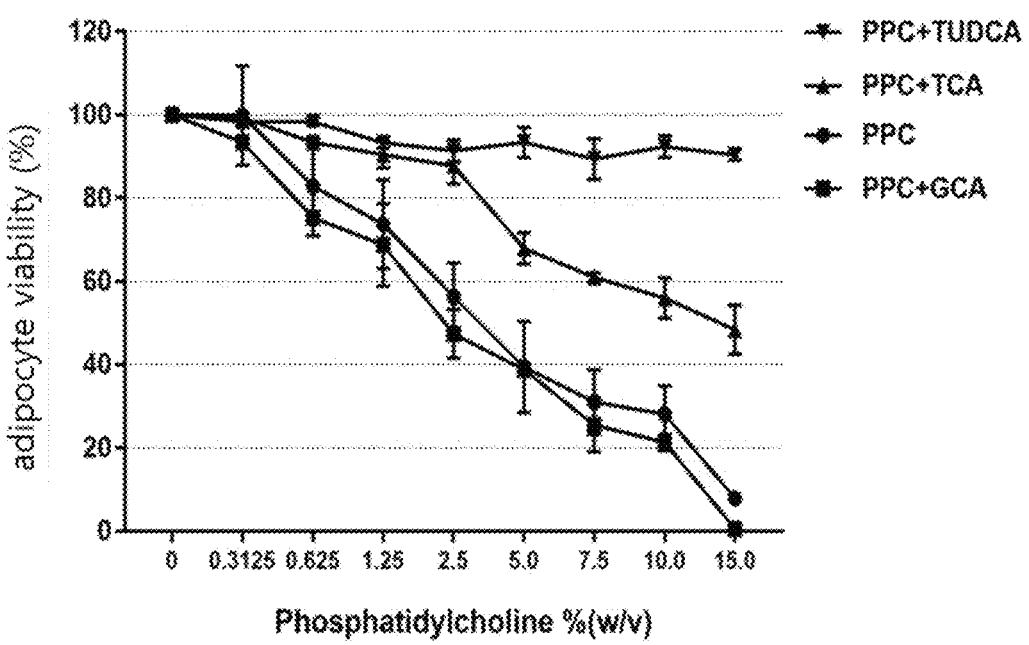
Figure 7E:
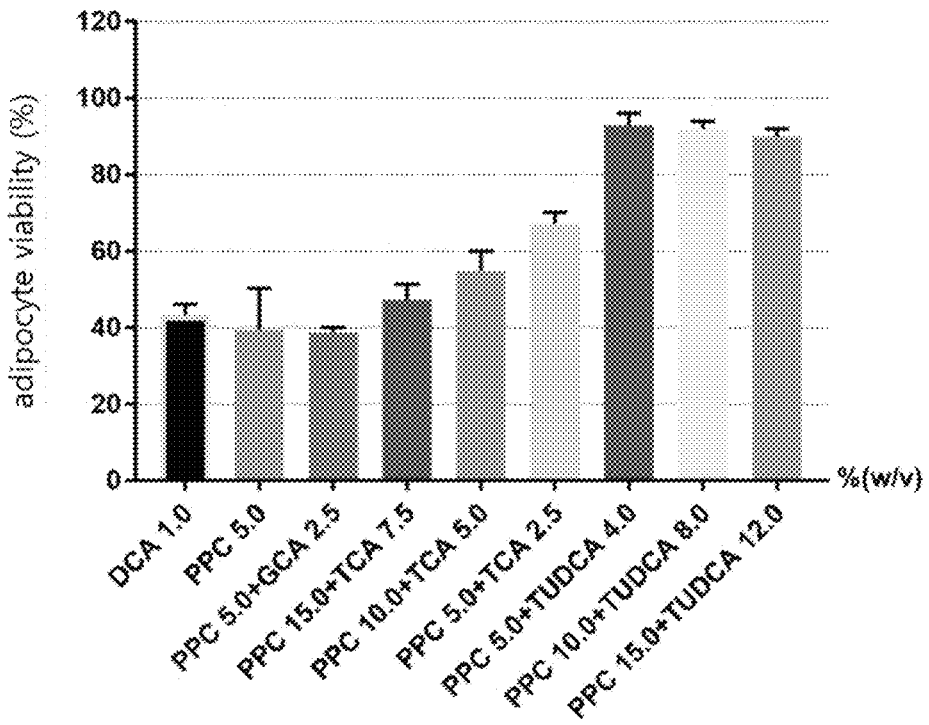

In addition, as shown in FIG. 7E, PPC 5.0% single composition, PPC 5.0%+GCA 2.5%, and PPC 15.0%+TCA 7.5% showed similar adipocyte-reducing activity to DCA 1.0% single composition at 96 hours. That is, preparations with the same adipocyte-reducing activity as Kybella (DCA 1.0%) approved by the FDA as an appearance improving cell lysing agent were PPC 5.0% single composition and complex composition of PPC 5.0%+GCA 2.5% and more. There was no statistically significant difference between those test groups (FIG. 7E).

The PPC single composition showed time and concentration-dependent adipocyte-reducing effect and PPC+GCA complex composition showed similar effect at the same concentration (this means test groups with the same PPC concentration). In comparison, PPC+TCA showed lower adipocyte-reducing effect at the same concentration, suggesting that TCA inhibits the adipocyte-reducing effect of PPC. Because of this, the 'PPC+TCA' formulation should be treated at very high doses to achieve the adipocyte-reducing effect similar to that of existing commercial products. That is, as shown in FIG. 7E, in order to obtain the adipocyte-reducing effect similar to that of a existing preparation such as Kybella (DCA 1.0%), it is necessary that PPC+TCA preparation is applied at a level of PPC 15.0%+TCA 7.5%. But, the PPC 15% composition solubilized with TCA 7.5% has a problem that it is difficult to administer multiple doses with a 30G injection needle due to a high viscosity of 20 cP or more. In summary, the 'PPC+TCA' preparation is considered to have some advantages in terms of side effects. However, considering the industrial economic feasibility and other additional concerns related to high dose administration, TPC+GCA' preparations are superior to TPC+TCA' preparations.

In addition, PPC solubilized with TUDCA was found to have no adipocyte-reducing effect even at high concentrations, which was also the case with very high doses (PPC 15%+TUDCA 12%). Thus, TUDCA was observed to inhibit adipocyte apoptosis and degradation. In this regard, studies on inhibition of cell apoptosis by TUDCA have been reported (Andrew L. Rivard, Administration of Tauroursodeoxycholic acid reduced apoptosis following myocardial infarction in rat, The American Journal of Chinese Medicine, Vol. 2, 279-295, 2007). These results suggest that PPC has a different effect on adipocyte reduction depending on the selection of solubilizing agent, and may act differently on cell necrosis and apoptosis.

Figure 7F:
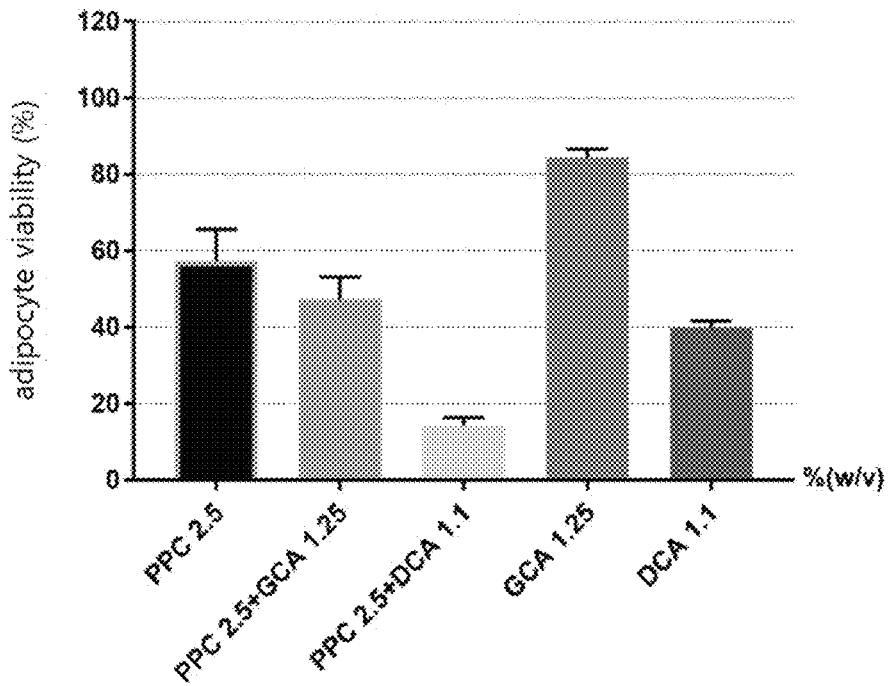
Figure 7G:
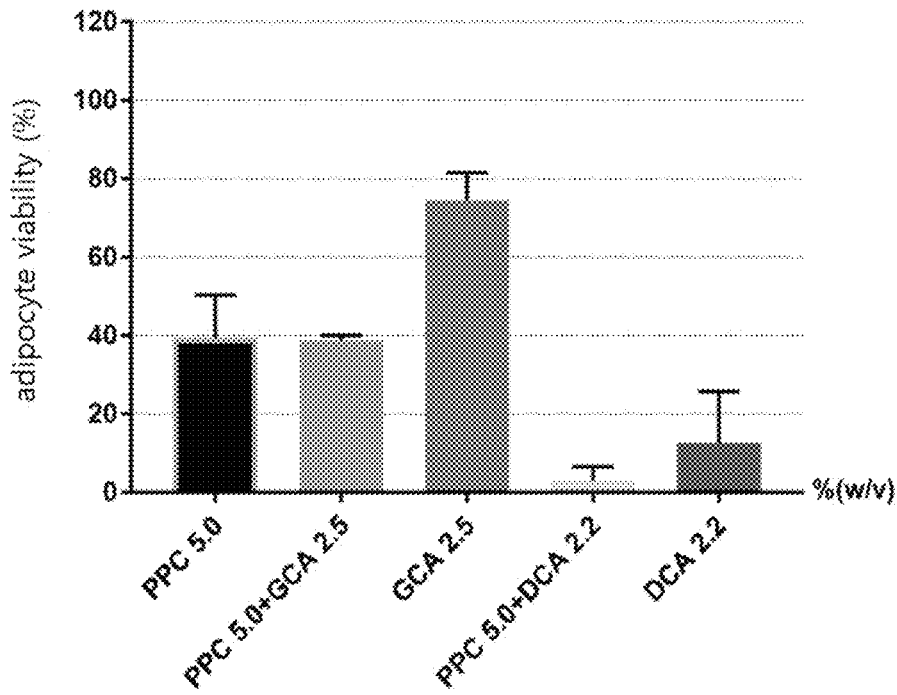
Figure 7H:
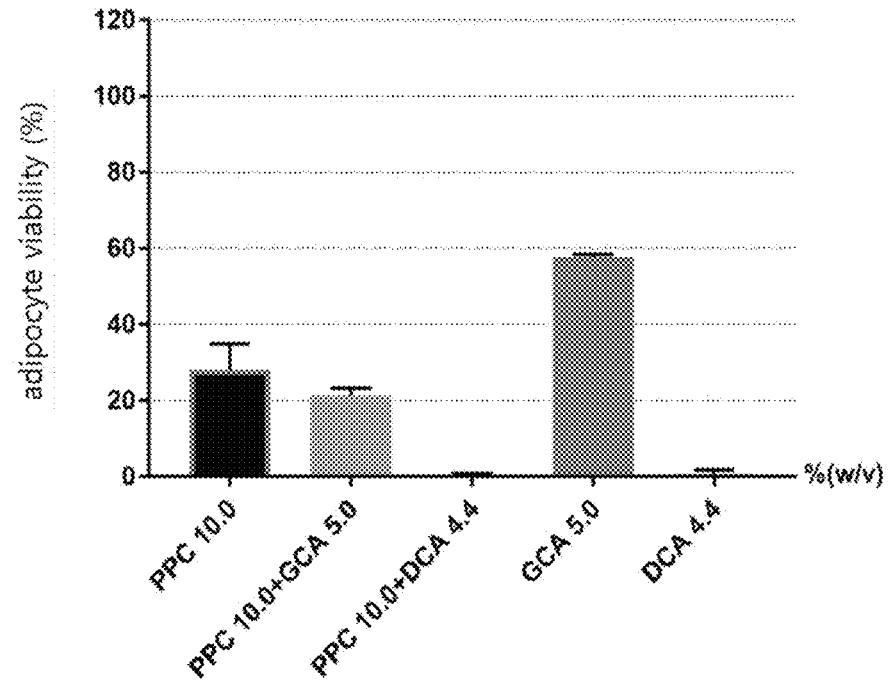

With regard to the PPC complex composition solubilized with GCA (PPC+GCA), that was selected preferably from the result of the above tests, and PPC complex composition solubilized with DCA (PPC+DCA), that is an existing commercial product, the effect of GCA and DCA selected as solubilizing agents on the adipocyte-reducing activity was observed other than the adipocyte-reducing activity of PPC single composition itself. The test results are shown in FIGS. 7F to 7H. After 96 hours, PPC single and PPC+GCA showed similar level of adipocyte-reducing effect at the same concentration (this means test groups with the same PPC concentration), but GCA single showed a lower adipocyte-reducing effect than PPC+GCA.

Figure 8A:
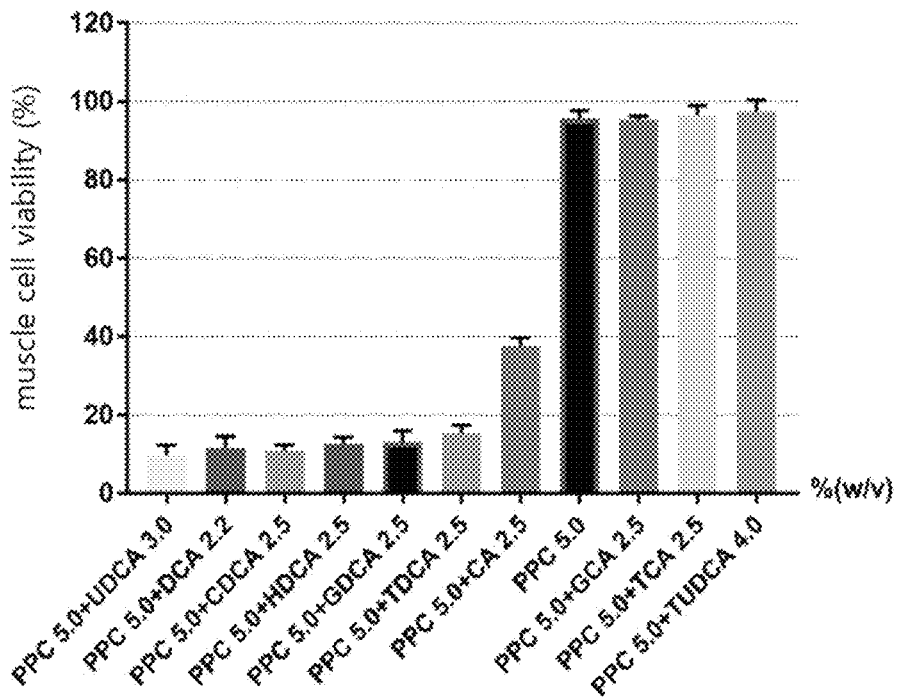
FIGS. 8A to 8D show a series of images demonstrating the decrease in viability of skeletal muscle cells (FIG. 8A), normal fibroblasts (FIG. 8B), vascular endothelial cells (FIG. 8C) and 3T3-L1 adipocytes (FIG. 8D) treated with PPC 5.0% single composition and PPC complex compositions solubilized with bile acids (PPC 5.0%+GCA 2.5%, PPC 5.0%+TCA 2.5%, PPC 5.0%+TUDCA 4.0%, PPC 5.0%+DCA 2.2%, PPC 5.0%+HDCA 2.5%, PPC 5.0%+UDCA 3.0%, PPC 5.0%+TDCA 2.5%, PPC 5.0%+GDCA 2.5%, PPC 5.0%+CDCA 2.5% and PPC 5.0%+CA 2.5%). Cell viability was measured by 3-(4,5-dimethyltazol-2-yl)-2,5-diphenyltetrazolium bromide (MTT) assay. The experiment was repeated 3 times per treatment and the results were expressed as the total percentage of viable cells versus untreated control.
Figure 8B:
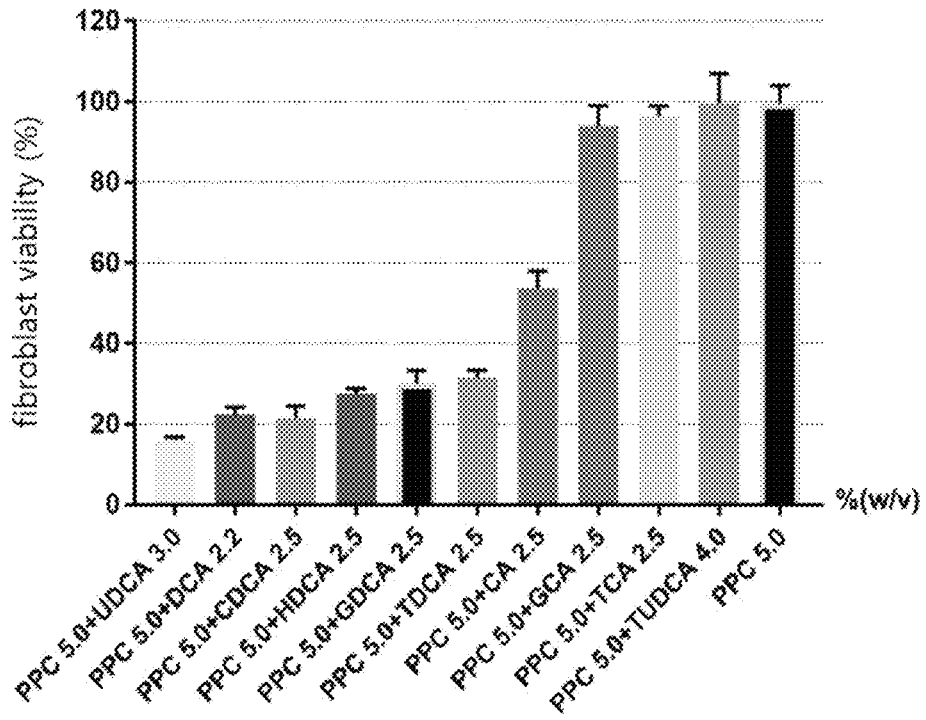
Figure 8C:
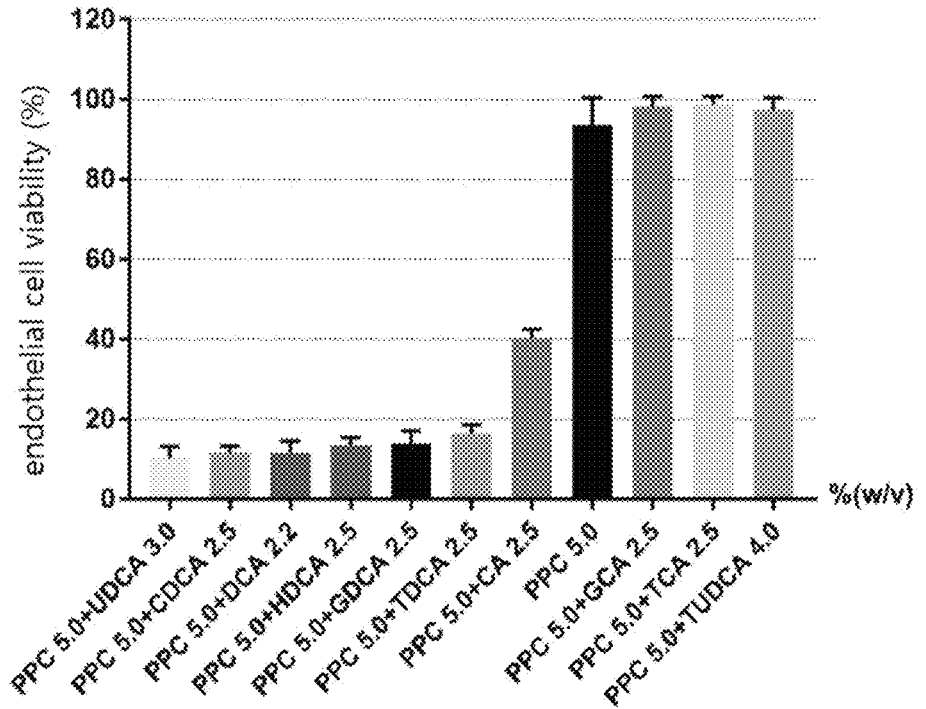
Figure 8D:
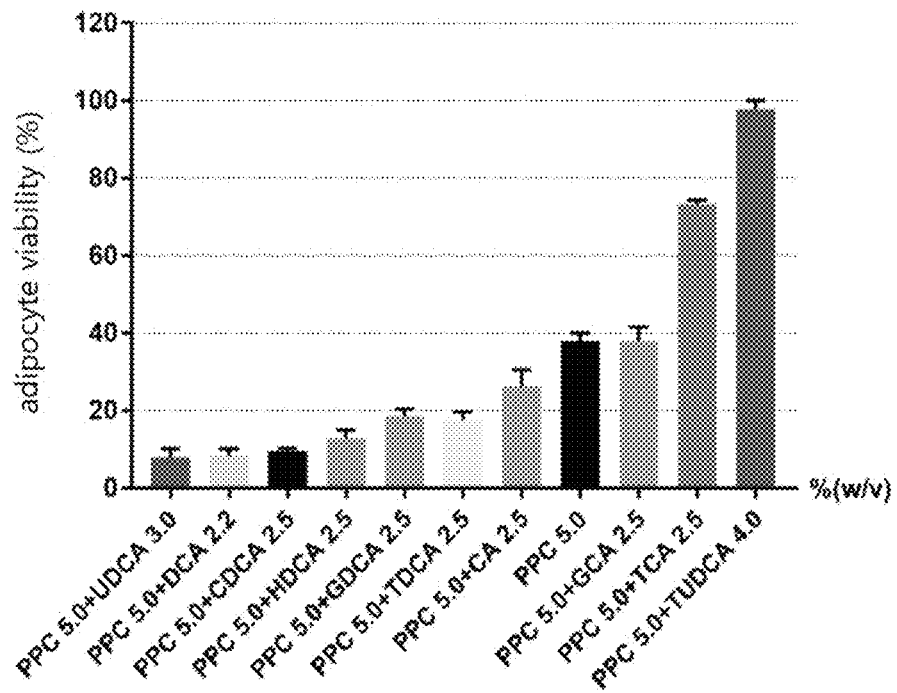
Figure 10A:
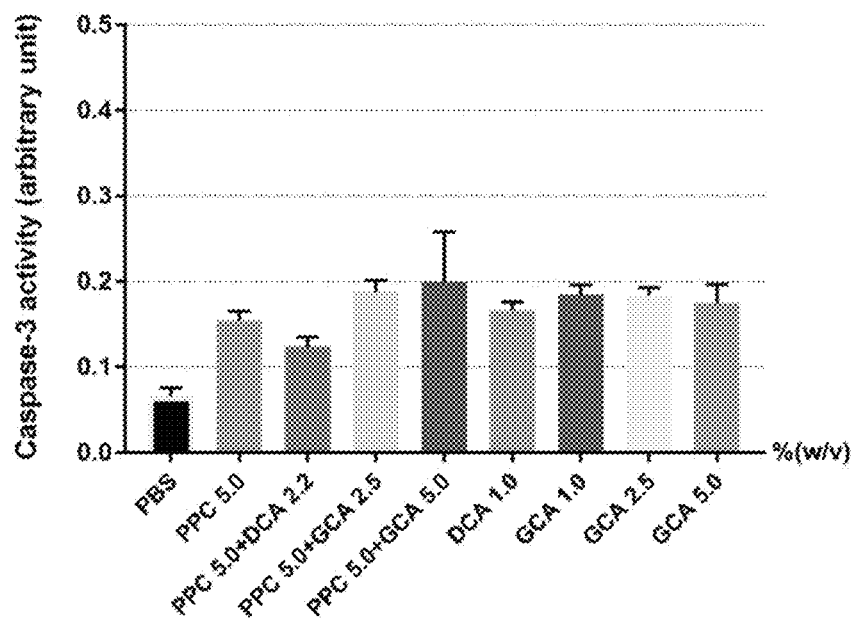
FIGS. 10A to 10D show a series of images demonstrating the result that the injectable composition of the present invention specifically has apoptosis effect, not necrosis of adipocytes, through caspase 3 activity assay and lipolysis effects through measuring the release of glycerol.
Figure 10B:
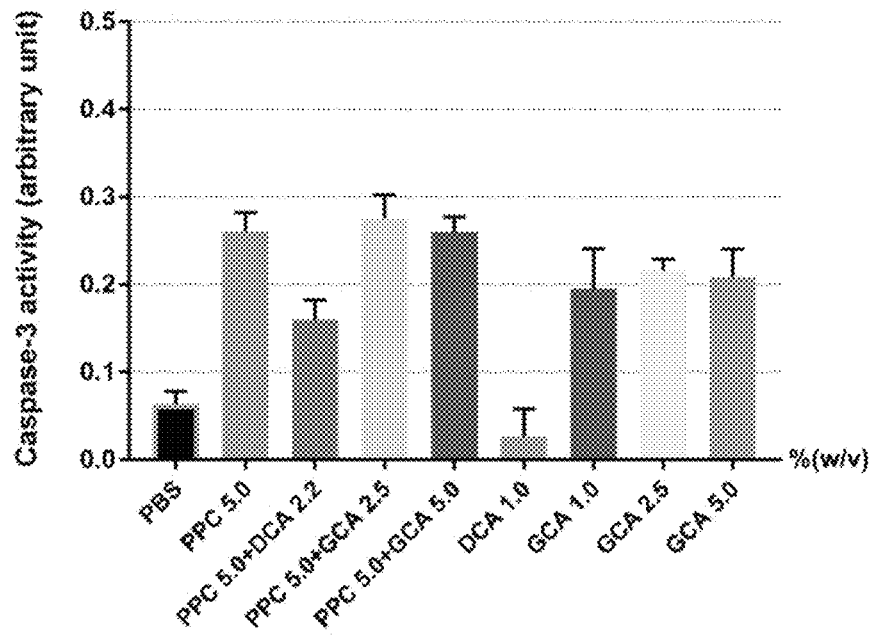

The PPC+DCA showed higher adipocyte-reducing effect at the same concentration as compared with PPC single, and showed higher adipocyte-reducing effect than DCA single (FIGS. 7F to 7H), but as shown in the following Test Example 2-3, such effect was attributed to cell necrosis (FIGS. 10A and 10B). In addition, HDCA, UDCA, CDCA, TDCA, GDCA and CA, which are other bile acids that have been found to be toxic similar to DCA in the above test examples (i.e., in edema, lesions and inflammation tests after in vivo subcutaneous injection), were also found to have the effect of decreasing adipocytes in a manner of inducing cell necrosis rather than adipocyte apoptosis and degradation, which are inherent mechanisms of PPC (FIG. 8D). Thus, these kinds of bile acid are not suitable solubilizing agents because they cause pain, edema and side effects, although the adipocyte-reducing effect may seem to be somewhat high.

The minimum molar ratio of GCA to PPC (GCA/PPC) required to prepare clear mixed micelles of PPC that is stably injectable is 0.76 mol/mol, and it requires 12 hours or more of stirring and 2 days of working time. For this reason, increasing the amount of GCA input can shorten the manufacturing time. However, excessive doses of additive may lead to negative effects on PPC-inherent pharmacological activity of adipocyte apoptosis and degradation as well as safety, so PPC concentration (5.0%) was fixed and GCA concentration (2.5%-8.75%) was increased to observe effects on adipocyte reuction.

Figure 7I:
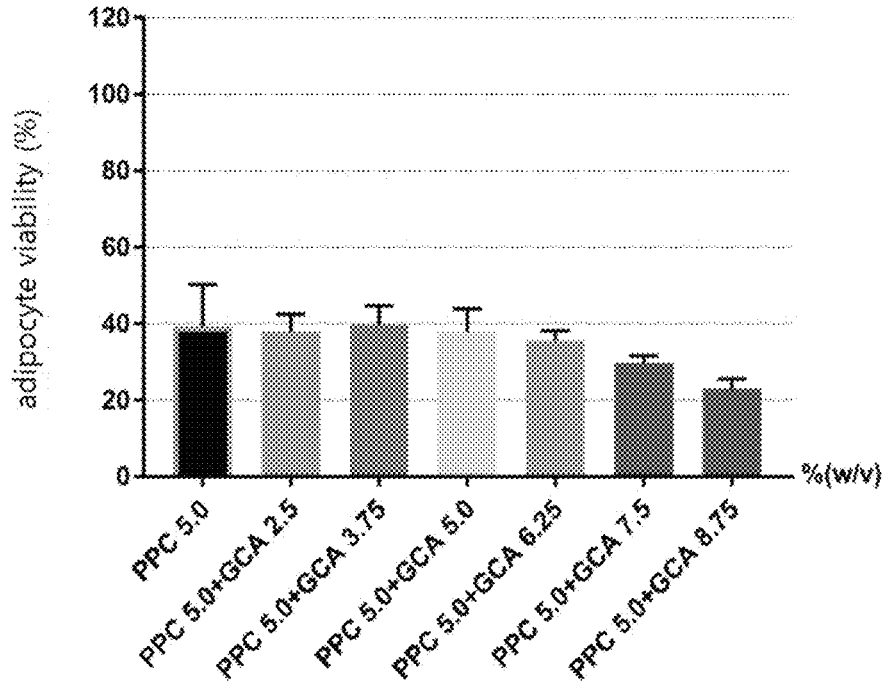

As a result, as shown in FIG. 7I, when the PPC 5.0% single composition and the PPC+GCA complex composition were compared, there was no statistically significant difference in the adipocyte viability between the test groups when the molar ratio of GCA to PPC (GCA/PPC) was 2.60 mol/mol (PPC 5.0%+GCA 7.50%) or less, and there was statistically significant difference in the adipocyte viability between the experimental groups when the molar ratio of GCA to PPC (GCA/PPC) was 3.04 mol/mol (PPC 5.0%+GCA 8.75%) or more. That is, when the GCA/PPC molar ratio is 3.04 mol/mol (PPC 5.0%+GCA 8.75%) or more, the possibility of adverse effects on the PPC-inherent positive activity is increased.

2-2: The Comparison of Adipocyte, Fibroblast, Skeletal Muscle Cell and Vascular Endothelial Cell Viability with PPC Complex Composition Solubilized with Bile Acids_ the Adipocyte Specificity of the Present Invention According to the previous reports, DCA or the PPC composition solubilized with DCA has been reported to cause serious clinical side effects due to lysing not only adipocytes but also fibroblasts, skeletal muscle cells, and vascular endothelial cells. In this respect, the effect of the PPC+GCA complex composition of the present invention was evaluated.

The specific method and materials of the test were as follow:

The cell viability was measured by MTT assay at 72 hours after treating 3T3-L1 adipocytes, normal fibroblasts, skeletal muscle cells and endothelial cells with PPC complex compositions (PPC 5.0%+GCA 2.5%, PPC 5.0%+TCA 2.5%, PPC 5.0%+TUDCA 4.0%, PPC 5.0%+DCA 2.2%, PPC 5.0%+HDCA 2.5%, PPC 5.0%+UDCA 3.0%, PPC 5.0%+TDCA 2.5%, PPC 5.0%+GDCA 2.5%, PPC 5.0%+CDCA 2.5% or PPC 5.0%+CA 2.5) respectively, and the results were calculated as the total percentage of viable cells compared to the untreated control group.

Figure 9A:
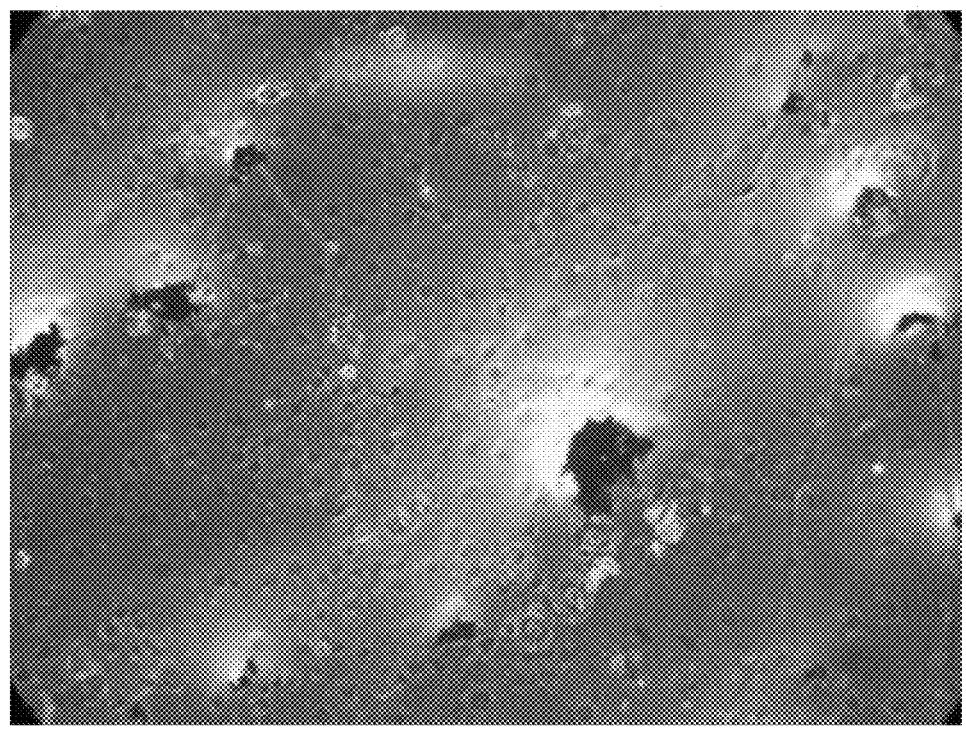
FIGS. 9A and 9B show the state before (FIG. 9A) and after (FIG. 9B) differentiation of 3T3-L1 adipocytes. Differentiation of 3T3-L1 precursor adipocytes (left image) was induced using differentiation medium. Differentiated adipocytes (right image) were stained using oil red staining method and stained with 200× magnification.
Figure 9B:
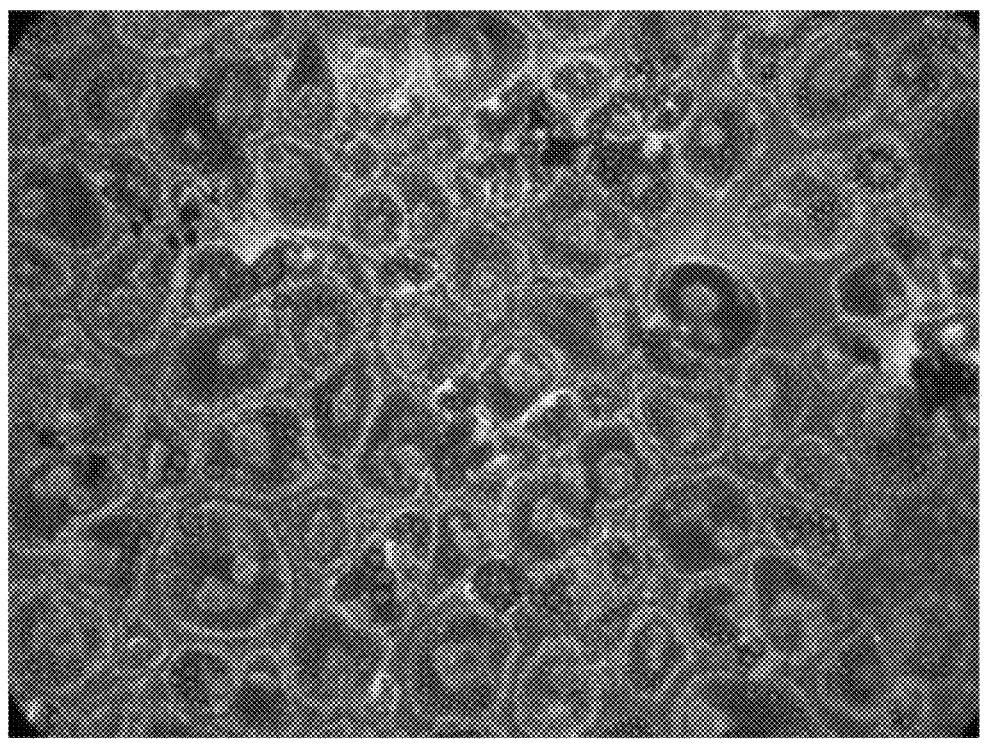

The 3T3-L1 adipocyte (ATCC) was cultured in Dulbecco's modified eagle medium (DMEM) (Invitrogen) supplemented with 10% fetal bovine serum, 100 units/ml penicillin and 100 μg/ml streptomycin under the condition of 5% $CO_2$ and 37° C. Adipocyte differentiation was continued for 2 or 4 days until the cell confluency reaches 100%, and the differentiation was induced for 3 days in DMEM medium containing 1 μg/ml insulin, 500 μM methyl-isobutyl-xanthine, and 250 nM dexamethasone (Pre-differentiation and post-differentiation adipocytes are shown in FIGS. 9A and 9B). Subsequently, the medium was replaced with DMEM medium containing 1 μg/ml insulin (Sigma), and the culture medium was maintained and changed every 2 to 3 days until the degree of differentiation reaches maximum. If it took more than 7 days, the cells were kept in normal DMEM culture medium until starting the tests. After 72 hours of incubation with treating test materials, the MTT solution was diluted to 1 mg/ml in PBS, and 50 μL, of MTT (Sigma) solution was added to the wells from which each culture medium had been removed. After the cells were incubated for 3 hours under the condition of 37° C. and 5% $CO_2$, the MTT solution was removed. After dissolving by treating 200 μL DMSO (Sigma), MTT assay (measured at 570 nm) was performed.

The fibroblasts (CCD-986sk, human fibroblast, based on Passage No. 2) were cultured up to 85% confluency, and then the culture medium (IMDM, 10% FBS, 1% antibiotics mix) was removed. After mixing and treating of the test material into a new culture medium, the culture medium was removed at the predetermined treatment time and MTT assay (measurement at 570 nm) was performed.

The skeletal muscle cells (C2C12; mouse myocyte, based on Passage No. 2) were cultured up to 80% confluency, and then the culture medium (DMEM, 10% FBS, 1% antibiotics mix) was removed. And the cells were cultured for 4 days in DMEM containing 2% horse serum. The elongated shape of the cells was observed at 80% or more, and the test materials were mixed and treated in a new culture medium, the culture medium was removed at the predetermined treatment time and MTT assay (measurement at 570 nm) was performed.

The vascular endothelial cells (HUVEC: human endothelium, based on Passage No. 3) were left at room temperature for 1 day in a culture dish coated with 1% gelatin. Then, the culture medium (EGM-Plus, 10% FBS, 1% antibiotics mix) was removed after culturing up to 80% confluency in the coated culture dish. After mixing and treating the test materials in a new culture medium, the culture medium was removed at the predetermined treatment time, and MTT assay (measured at 570 nm) was performed. (Note: Discard if cells pass Passage No. 6 or more).

As a result of observing the viability of various cells, as shown in FIGS. 8A to 8D, the PPC complex compositions solubilized with GCA or TCA were found to selectively reduce only adipocytes unlike the PPC complex compositions solubilized with DCA, UDCA, HDCA, CDCA, TDCA, GDCA or CA. This suggests that when the composition of the present invention, PPC+GCA, is applied to an actual person, it can specifically reduce only adipocytes without adversely affecting human tissues around adipocytes.

2-3: The Caspase 3 Activity Assay

The Caspase 3 activity assay was performed with the test materials to determine whether the cell death in the result of MTT assay was due to necrosis or apoptosis. The Caspase 3 specifically increases when apoptosis occurs and is a marker of apoptosis. The Caspase 3 Assay Kit (Colorimetric) from Abcam was used according to the manufacturer's manual, and the method of the test was as follows: The 1×10⁵ cells of 3T3-L1 adipocytes were distributed to each well, and preparations comprising PPC 5.0%, PPC 5.0%+DCA 2.2%, PPC 5.0%+GCA 2.5%, PPC 5.0%+GCA 5.0%, DCA 1.0%, GCA 1.0% or GCA 5.0%, and PBS were treated, followed by incubating for 0-48 hours at 37° C. The cells were then treated with 50 ul of cell lysis buffer (10 mM Tris-HCl, 10 mM $NaH_2PO_4$/$NaHPO_4$, pH 7.5, 130 mM NaCl, 1% Triton X-100 and 10 mM sodium pyrophosphate) and left at 4° C. for 10 mM. The supernatant was collected by centrifugation at 1000× rpm for 1 minute, and protein quantification was performed by BCA method. The 50 µl of reaction buffer (4 mM HEPES, pH 7.5, 10% glycerol, 2 mM dithiothreitol) and 0.5 µl of 4 mM DEVD-p-NA were added to each sample and reacted at 37° C. for 1 hour. Then wavelength was measured with a Spectrofluorometry at 405 nm.

As a result, as shown in FIGS. 10A and 10B, PBS did not induce caspase-3 activity in adipocytes. PPC single composition and PPC+GCA complex composition showed a time-dependent effect of inducing caspase-3 activity to a considerable extent. However, the PPC+DCA complex composition inhibited capase-3 activity compared to PPC or PPC+GCA. Interestingly, DCA 1.0% showed some caspase-3 activity up to 24 hours, but after 48 hours, caspase-3 activity returned to pretreatment levels. This phenomenon is considered to be due to the action of cell apoptosis until 24 hours after the treatment of the DCA single composition, and then to a reaction in which the cells become necrotic by the subsequent inflammatory reaction. The Caspase-3 activity was observed in GCA treated group, but there was no time or concentration-dependent change. On the other hand, it was confirmed that the Caspase-3 activity was shown to be high in the GCA+PPC complex preparation in a time and concentration dependent manner. When PPC was mixed with DCA, the activity of caspase-3, which is induced by PPC single composition, was significantly reduced. These results indicate that the apoptosis-specific effect of PPC single composition is inhibited by DCA, and that the PPC preparation added with DCA induces more necrosis of adipocytes which is concerned with inflammation, and the like.

2-4: The Lipolysis Assay

The glycerol activity assay was performed with the test materials to determine whether the cell death in the MTT assay was due to necrosis or lipolysis. Glycerol is a specific marker that increases when fat breaks down. Abcam Lipolysis Assay Kit (Colorimetric) was used according to the manufacturer's manual, and the method of the test was as follows: The 1×10⁵ cells of 3T3-L1 adipocytes were distributed to each well, and preparations comprising PPC 5.0%, PPC 5.0%+DCA 2.2%, PPC 5.0%+GCA 2.5%, PPC 5.0%+ GCA 5.0%, DCA 1.0%, GCA 1.0% or GCA 5.0%, and PBS were treated, followed by incubating for 0-48 hours at 37° C. And then the lysis was induced. The 30 ul of lipolysis assay buffer (137 mM NaCl, 5 mM KCl, 4.2 mM $NaHCO_3$, 1.3 mM $CaCl_2$, 0.5 mM $KH_2PO_4$, 0.5 mM MgCl2, 0.5 mM $MgSO_4$, 5 mM Glucose, 20 mM Hepes (pH 7.4), 1% BSA, 1 uM Isoproterenol) was added to the culture medium adjusting the total volume to 50 ul, and it was incubated for 20 minutes. After adding the glycerol assay complex (50 µl) thereto, the solution was incubated at room temperature for 30 minutes. Absorbance was measured at OD 570 (using standard curve for absolute determination).

Figure 10C:
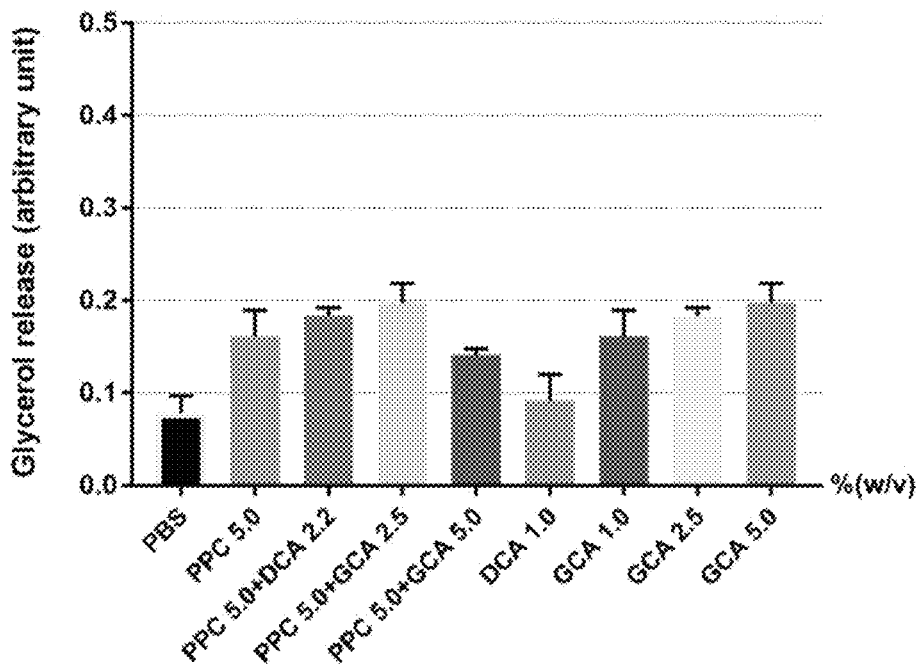
Figure 10D:
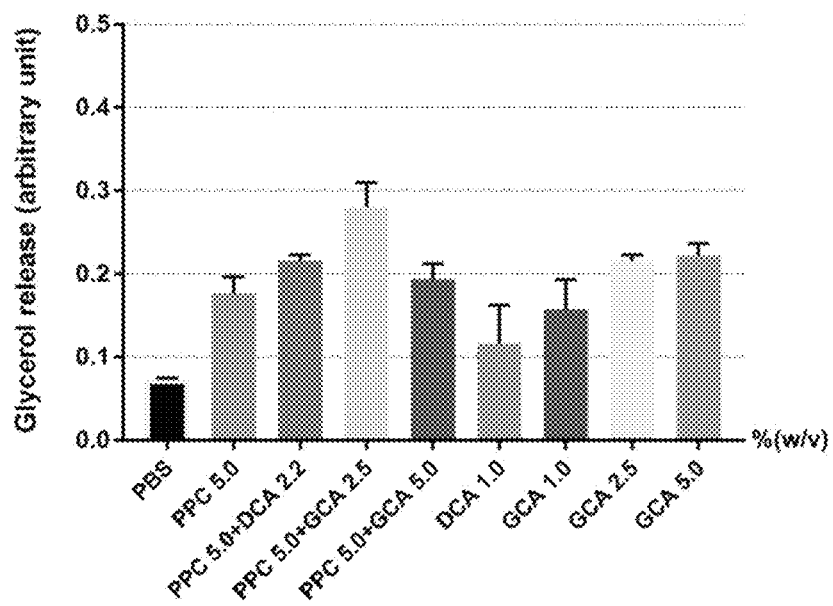

As a result, as shown in FIGS. 10C and 10D, PBS did not induce glycerol secretion in adipocytes. At 24 hours, except for DCA 1.0% and PPC 5.0%+GCA 5.0%, the test materials similarly induced glycerol secretion. At 48 hours, PPC single, PPC+DCA, DCA single and GCA single groups showed slightly higher cytolytic activity than that of 24 hours. In particular, the PPC+GCA group showed a much higher cell-apoptotic effect than the PPC single composition.

Test Example 3: The Evaluation of Efficacy and Side Effect of Injectable Preparations in Mouse Obesity Model Induced by High-Fat Diet Male C57BL/6 mice (4 weeks old) were purchased. A high fat diet (Research diet, 60% kcal lipid) was provided to make them highly obese for 12 weeks. After then, single compositions of PPC (2.5%, 5.0%, 10.0% and 15.0%), PBS (negative control), Isuprel (positive control), DCA 1.0% and GCA 2.5%, and complex compositions of PPC 5.0%+DCA 2.2%, PPC 5.0%+HDCA 2.5%, PPC 5.0%+UDCA 3.0%, PPC 5.0%+TDCA 2.5, PPC 5.0%+GDCA 2.5%, PPC 5.0%+ CDCA 2.5%, PPC 5.0%+CA 2.5%, PPC 5.0%+TUDCA 4.0%, PPC 5.0%+TCA 2.2% and PPC (2.5-10.0%)+GCA (1.25-5.0%) were directly administered into the fat tissue of inguinal region (subcutaneous fat tissue) of mouse obesity model induced by high-fat diet, respectively, and in vivo fat reduction was observed. Each test material was administered once. 0.2 ml of each test material was subcutaneously injected into the inguinal fat pad of the mice. Finally, mice were sacrificed at 8 days post-injection. The inguinal fat pad of the sacrificed mice was dissected and the subcutaneous fat was quickly removed and fixed in 4% formaldehyde solution. After fixation, the fat pad was washed and dehydrated, treated with paraffin solution to make a paraffin block, stained with hematoxylin and eosin, and observed with an optical microscope.

Figure 11A:
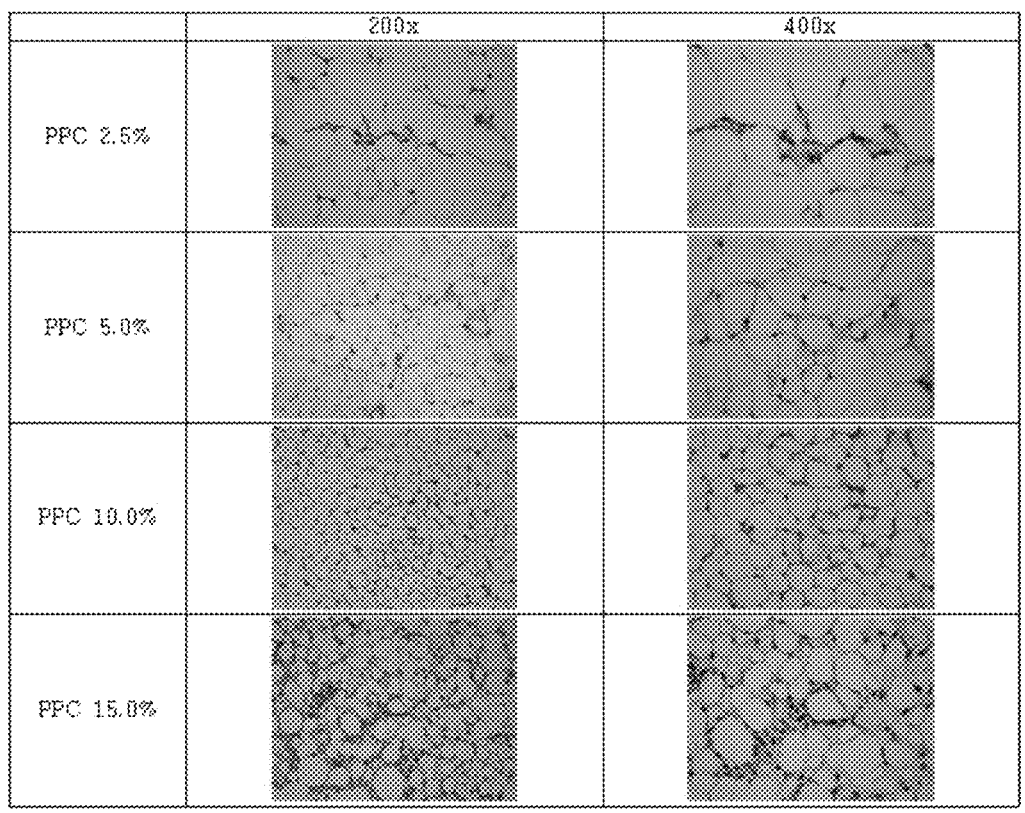

First, in the tissue injected with the PPC single composition, adipocyte apoptosis and degradation were induced in a concentration-dependent manner at a concentration range of 2.5% to 10%, and the size of the adipocytes in the fat tissue was reduced. Some of the reduced adipocytes were stuck together, the region of dead cells was clear, and adipocytes seemed to be enlarged due to the fusion of the degraded adipocytes. At 15.0% concentration, not only reduced adipocyte, but also the development of macrophages was confirmed around adipocytes (FIG. 11A).

Figure 11C:
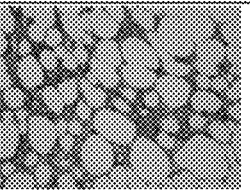
Figure 11C:
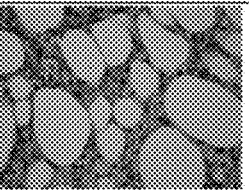
Figure 11C:
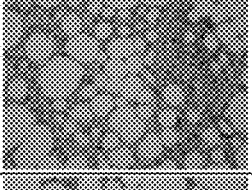
Figure 11C:
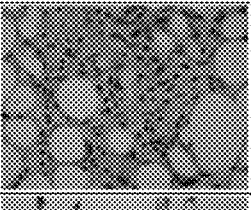
Figure 11C:
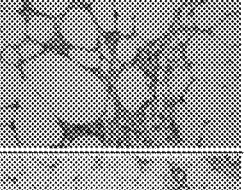
Figure 11C:
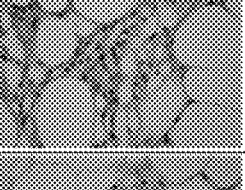
Figure 11C:
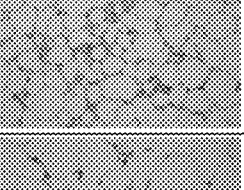
Figure 11C:
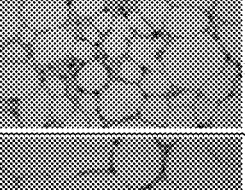
Figure 11C:
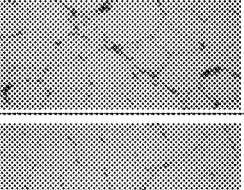
Figure 11C:
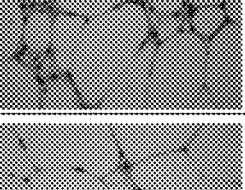
Figure 11C:
Figure 11C:

Next, in the case of the PPC complex compositions solubilized by bile acids, adipocyte apoptosis was clearly observed, small-adipocyte was shown, and macrophage-mediated phagocytosis was evident around adipocytes in the fat tissues injected with the PPC complex compositions solubilized with DCA, CDCA, HDCA, UDCA, GDCA, TDCA or CA. In the fat tissues injected with Isuprel, the negative control group, the size of the adipocytes was reduced, the configuration of cell apoptosis was observed, and infiltration of cells other than adipocytes for clearing the apoptotic-cell was observed. In the fat tissues injected with the DCA single composition or the PPC compositions solubilized with DCA, the severe inflammation was induced at the site of the administration of the compositions, and the cell was lysed by necrosis, and remarkable destruction was induced. The DCA single composition showed severe inflammation even though DCA was contained at a low concentration of 1%, and the inflammation inducing action was greater than that of the PPC single composition and the PPC+GCA complex compositions. Relatively, in the fat tissues injected with PBS (negative control) or PPC 5.0%+ TUDCA 4.0% had a clear cell membrane boundary and a well-formed cell shape, and consisted only of adipocytes in the tissues. In the fat tissues injected with PPC 5.0%+TCA 2.5%, the size of adipocytes reduced as a whole and infiltration of cells other than adipocytes for clearing apoptotic-cells was observed in small area. In the fat tissues injected with PPC 5.0%+GCA 2.5% of the present invention, inflammation wasn't induced, the size of adipocytes was reduced, the region of apoptosis was clear, and the adipocytes seemed to be enlarged due to the fusion of the degraded adipocytes (FIGS. 11B and 11C).

As shown in FIG. 11D, as a result of examining the effect of the PPC+GCA complex composition of the present invention on not only adipocytes but also dermis and epidermis after injection into a fat pad of a rat, after the PBS injection, the dermal and epidermal tissues were well preserved and there were no inflammatory cells such as neutrophils. And there were clear cell membrane boundary and a well-formed cell shape in fat tissues, and the fat tissues consisted only of adipocytes. After injection of PPC 5.0% single composition, the dermal and epidermal tissues were well preserved and there were no inflammatory cells such as neutrophils. In fat tissue, the size of adipocytes was reduced, and some of the cell membranes were degraded, and some adipocytes seemed to be enlarged due to the fusion of the degraded adipocytes. After injection of PPC 2.5%+GCA 1.25% complex composition, the dermal and epidermal tissues were well preserved and there were no inflammatory cells such as neutrophils. In fat tissue, the size of adipocytes was reduced, and some of the cell membranes were degraded, and some adipocytes seemed to be enlarged due to the fusion of the degraded adipocytes. After injection of PPC 5.0%+GCA 2.5% complex composition, the dermal and epidermal tissues were well preserved and there were no inflammatory cells such as neutrophils. In fat tissue, the size of adipocytes was reduced, and the region of apoptosis was clear, and some adipocytes seemed to be enlarged due to the fusion of the degraded adipocytes. After injection of PPC 10.0%+GCA 5.0% complex composition, the dermal and epidermal tissues were slightly damaged and there were some inflammatory cells and slight edema was observed. In fat tissue, the size of adipocytes was reduced, and there was phagocytosis of macrophages in the region of apoptosis and debris of nucleic acid due to apoptosis, and some adipocytes seemed to be enlarged due to the fusion of the degraded adipocytes. After injection of GCA 2.5% single composition, the dermal and epidermal tissues were slightly damaged, and there were inflammatory cells dispersed such as neutrophil and the like, so the inflammation was clearly observed. And there were clear cell membrane boundary and a well-formed cell shape in fat tissues, and the fat tissues consisted only of adipocytes. From the above results, it was confirmed that the inflammatory reactions on the adipocyte, dermis, and epidermis were more significantly induced when GCA single composition was treated than GCA and PPC complex preparations.

In summary, in the fat tissue injected with DCA single or with PPC complex composition solubilized with DCA, HDCA, UDCA, CDCA, TDCA, GDCA or CA, severe inflammation was induced at the site of administration and the cells were lysed by necrosis, and significant destruction was induced. However, in the fat tissue injected with the PPC+GCA complex composition of the present invention, the size of the adipocyte was reduced and the region of apoptosis was clear. And some adipocyte became larger due to the fusion of degraded adipocytes. Although the concentration-dependent inflammation was slightly induced, morphological features of damage to the adipocyte membrane appeared.

Test Example 4: The Evaluation of Toxicity of PPC Injectable Preparations Solubilized with GCA Toxic effects of PPC 5.0% injectable preparation solubilized with GCA 2.8% were evaluated with a single subcutaneous administration to beagle dogs. Specifically, all animals were checked for tattoo numbers, and their general condition, body weight, and body temperature were measured upon arrival. During 12 days of quarantine and adaptation period after arrival, general symptoms were observed once a day body weight was measured once a week, and health status of animals was checked at the end of quarantine and adaptation period. After the termination of quarantine and adaptation period, one male and one female of the control group, and two male and two female of each test group animals were separated on the basis of body weight. The test animals were total of 14 beagle dogs (male: 5~6 months, 7.05~8.16 kg/female: 5~6 months, 5.83~7.14 kg) in each of 7 male and 7 female dogs, and the administration doses per individual animal were calculated based on the body weight on the day of administration, and nape was epilated before administration. The test materials were subcutaneously administered into left and right side of nape using disposable syringe (10 ml, 23G). The test groups were set as low dose group (dose: PPC 90 mg/kg+GCA 50.4 mg/kg, amount of injection: 1.8 ml/kg, maximum amount of injection per site: 0.8 ml/site), medium dose group (dose: PPC 180 mg/kg+GCA 100.8 mg/kg, amount of injection: 3.6 ml/kg, maximum amount of injection per site: 1.6 ml/site), high dose group (dose: PPC 360 mg/kg+GCA 201.6 mg/kg, amount of injection: 7.2 ml/kg, maximum amount of injection per site: 3.2 ml/site) and control group (saline, amount of injection: 7.2 ml/kg, maximum amount of injection per site: 3.2 ml/site). Detailed test results are described below.

1) the presence or absence of death; During the test period, no deaths were observed in all test and control groups.

2) general symptoms; During the test period, no symptoms were observed in all test and control groups.

3) Weight change; During the test period, no abnormal changes were observed in all test and control groups.

4) autopsy; No abnormal changes were observed in all test and control groups.

Figure 12A:
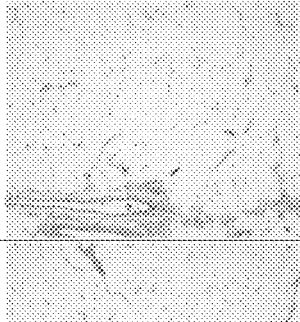
FIGS. 12A to 12C show the images of results of a single-dose subcutaneous administration of PPC+GCA complex composition to a dog, beagle, in order to observe the toxic reaction. After 14 days of administration, autopsy was carried out for histopathological examination, and images were taken after H&E staining.
Figure 12A:
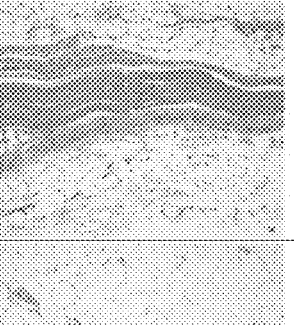
Figure 12A:
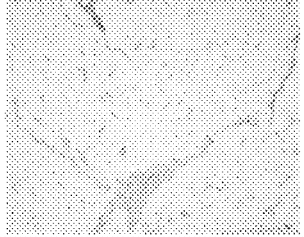
Figure 12A:
Figure 12B:
Figure 12B:
Figure 12B:
Figure 12B:
Figure 12C:
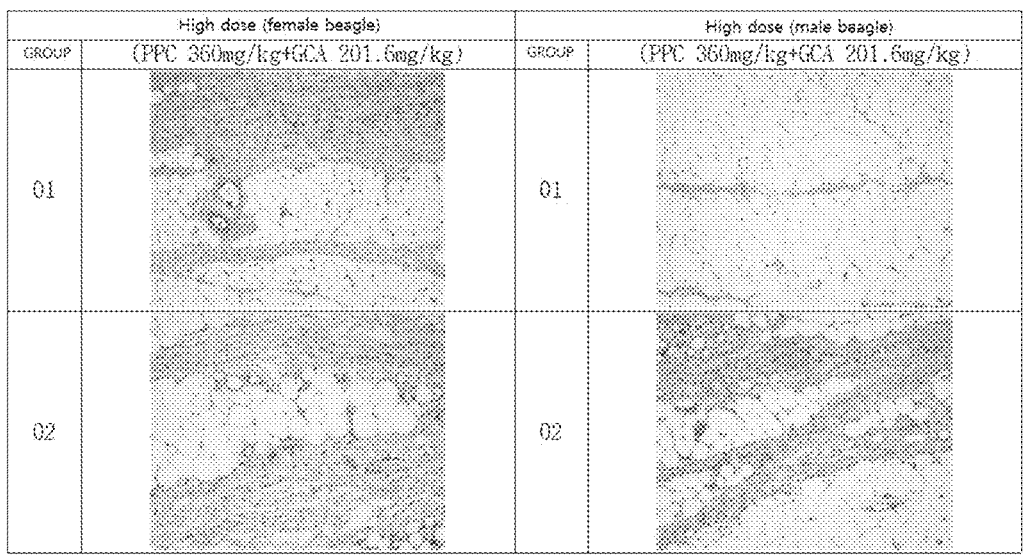

5) histopathological examination; Little to slight degree of granulomatous inflammation was observed in the subcutaneous tissues of the male and female high dose groups (see FIGS. 12A to 12C). As described above, very slight inflammation was observed only in the high dose group injected with the injectable preparation of the present invention. However, from the viewpoint of the setting the appropriate dose concentration upon administration to humans and other animals, such degree of inflammation can be considered as no side effects.

Test Example 5: The Comparison of In Vivo Pain

The following results were obtained by evaluating the degree of pain induced by single composition of DCA, GCA or PPC, and complex composition of PPC solubilized with bile acid by measuring the moving distance and the moving speed of the animal in vivo. In the following, % of the composition means % (w/v).

Specifically, edema was observed after injecting 100 ul of single composition (DCA 1.0%, PPC 5.0% or GCA 2.5%) or complex composition (PC 5.0%+DCA 2.2%, PPC 5.0% HDCA 2.5%, PPC 5.0%+UDCA 3.0%, PPC 5.0%+TDCA 2.5%, PPC 5.0%+GDCA 2.5%, PPC 5.0%+CDCA 2.5%, PPC 5.0%+CA 2.5%, PPC 5.0%+GCA 2.5%, PPC 5.0%+TCA 2.5% or PPC 5.0%+TUDCA 4.0%) to mouse paw. After the edema was confirmed to be the most at 2 hours after administration, the moving distance (cm) and the moving speed (cm/s) for 5 minutes were compared using Noldus Video Traking system.

Figure 13A:
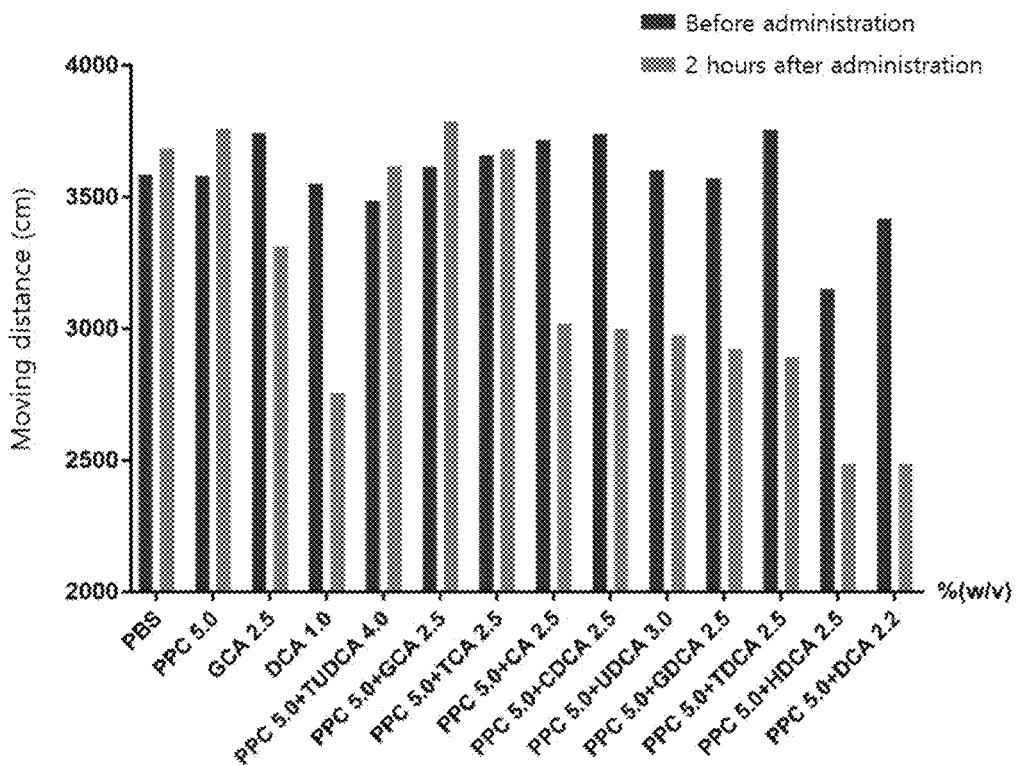
FIGS. 13A and 13B show the results of evaluating the degree of in vivo pain induction by measuring the moving distance (cm) and the moving speed (cm/s) of experimental animals. Specifically, 100 μl of each test material was injected into the floor of the paws of the rats, and edema was observed. As a result, it was confirmed that the most severe edema was observed at 2 hours after injection, and this time point was set for maximum pain. The movement before and after injection of the test material was compared through distance and time. The movement before and after injection was measured using Noldus Video Traking system and compared with moving distance (FIG. 13A) and moving speed (FIG. 13B).
Figure 13B:
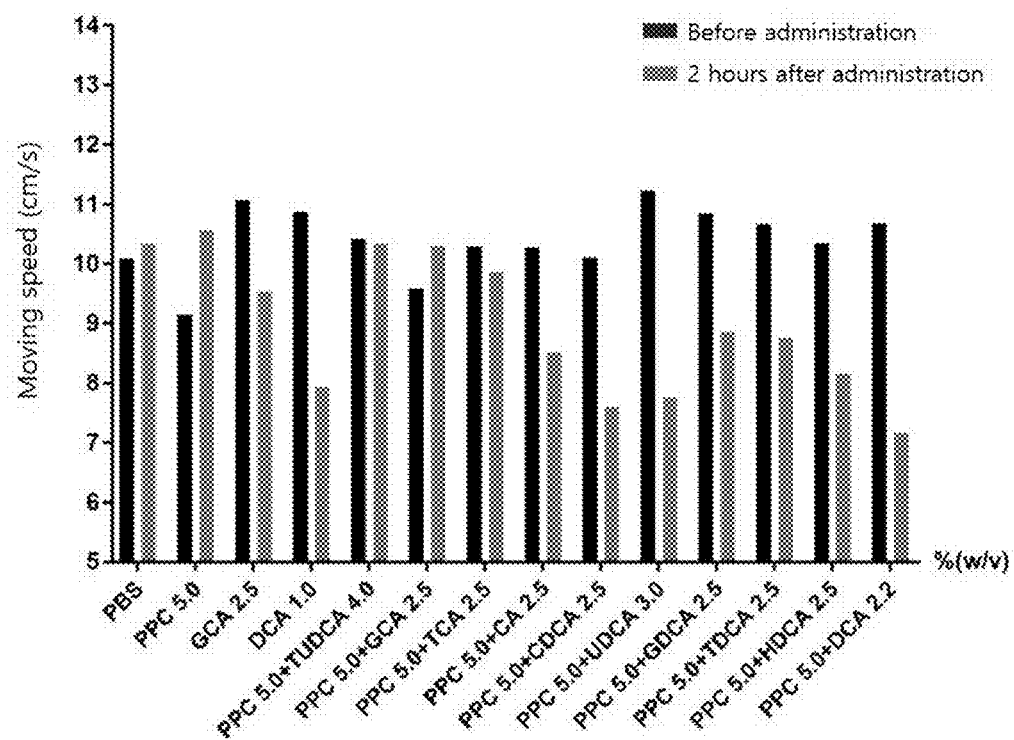

As shown in FIGS. 13A and 13B, the moving distance and moving speed of PPC 5.0% single composition, PPC 5.0%+TUDCA 4.0%, PPC 5.0%+GCA 2.5% and PPC 5.0%+TCA 2.5% group wasn't changed or was slightly increased. On the other hand, the moving distance and moving speed of PC 5.0%+DCA 2.2%, PPC 5.0%+HDCA 2.5%, PPC 5.0%+UDCA 3.0%, PPC 5.0%+TDCA 2.5%, PPC 5.0%+GDCA 2.5%, PPC 5.0%+CDCA 2.5% and PPC 5.0%+CA 2.5% group was decreased by about 20%, and these results were judge to be due to decreased activity due to pain. This suggests that the injectable preparation of the present invention is significantly less painful (substantially no pain) than the existing commercial products.

Test Example 6: The Clinical Evaluation of PPC Compositions Solubilized with GCA 6-1: The Clinical Evaluation Regarding Efficacy of Fat Reduction Among the compositions of the present invention, the PPC 5.0% injectable composition solubilized with GCA 2.8% was administered to patients having localized submental fat deposition. Specifically, after topical anesthesia with 9.6% lidocaine cream for 30 minutes or more, a 5-cc syringe was loaded with 13 mm 30G injection needle and the composition was injected 6 times at intervals of 4 weeks into the submental fat (total of 50 points, 0.2 cc per point and total of 10 ml, 1.0 cm interval and in 6-8 mm depth). After 12 weeks, standard clinical photographs, CT (computed tomography) imaging, the improvements reported by the researchers, the improvements reported by the subjects and the satisfaction of the subjects were evaluated.

The clinical photographs were taken before and 12 weeks after the final administration, and the frontal, left perspective view, right perspective view, and left and right sides of the subjects were photographed under the following conditions: In the frontal photographs, the subject gazed at the camera in a posture in which the Frankfort horizontal plane, which is the plane where the tragion of both ears of the subject and the lowermost part of the orbital palate meet, was horizontal. In the perspective view photographs, after turning the subject's body for 45 degrees, the subject gazed at the camera in a posture in which the face was positioned so as to be in line with the nose tip and the edge of the ball, and the Frankfort horizontal plane was horizontal. In the side photographs, the subject's body was rotated for 90 degrees from the frontal position so as to be in line with the nose tip and the chin. At this point, it was confirmed that the opposite eyebrows were not visible, and that the posture was correct so that the body didn't lean to the side, bend or stretch. And then the subject gazed at the camera in a posture in which the line connecting the back of the subject and the back of the head was adjusted to be vertical and the Frankfort horizontal plane was horizontal. The camera used for photographing was a Nikon DSLR-camera D5200 with a 60 mm short focus lens.

The CT images were taken before and 12 weeks after the last administration, and the thickness and area of the submental fat were measured. The subject suffered from swallowing saliva according to the announcement while lying comfortably after wearing the specified top and headband.

The CT images were taken before and 12 weeks after the final administration, and the thickness and area of the submental fat were measured. The subject suppressed swallowing saliva according to the announcement while lying comfortably after wearing the specified top and headband. At this time, the pillow for CT imaging was NECK type, and the head of the subject was fixed to the laser guide line which passed through the forehead, nose, chin, and middle of the clavicle. The imaging parameters of the CT imaging were the scan range (from the ear canal to bottom of the clavicle), slice (5.0 mm), FOV with skin, matrix size 512×512, rotation time of 0.5 sec and beam collimation 64×0.6 mm. The device were from GE Medical systems, and the image was analyzed using Xelis 1.0 6.0 BN 6 3D from Infinity.

Figure 14A:
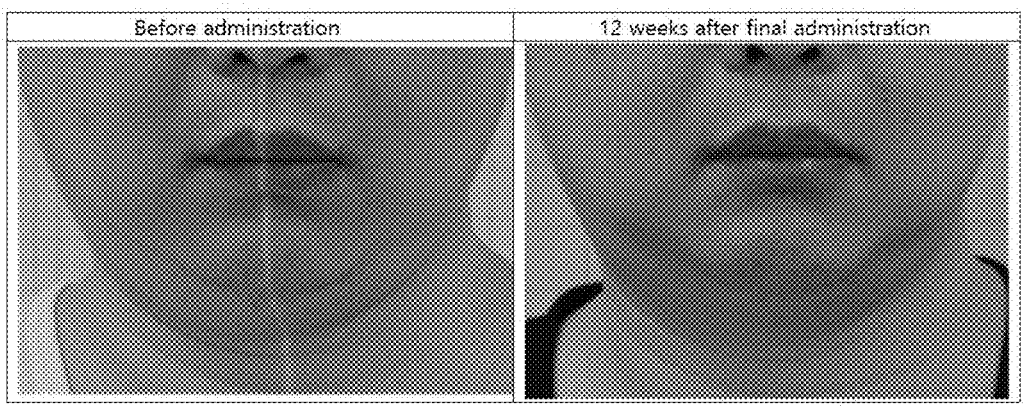

The clinical efficacy of the injectable composition of the present invention is well shown in FIGS. 16A and 16B. FIG. 14A is a photograph showing a clinical image of a subject before the administration and 12 weeks after the final administration, wherein the PPC complex composition solubilized with GCA of the present invention was administered 6 times at intervals of 4 weeks at a dose of 0.2 cc per point, total of 50 points, total of 10 ml to the subject, and the reduction of submental fat was observed even with the naked eyes. The level of satisfaction reported by the subject was 4 out of 5, and the improvement evaluated after comparing the images of before the administration was 1.5 grade. Interestingly, the subject was a patient who had previously received a PPC injectable composition solubilized with DCNa (commercially available as Lipobean i.v.), and the subject described a significant surprise that the compositions of the present invention were painless upon administration, immediately after administration, and over time.

In addition, FIG. 14B shows the result of the quantitative evaluation of the amount of locally deposited fat reduction through CT. The thickness of the pre-platysmal submental fat located 3 cm below the mandibular end point of the CT sagittal plane passing through the median chin was decreased by 30.36% from 5.6 mm before the administration to 3.9 mm after 12 weeks of the final administration.

6-2: The Clinical Evaluation Regarding a Pain, Edema and Side Effect

Six male and female patients who had received PPC injectable composition solubilized with DCA (previously commercialized) were subjected to clinical evaluation of pain, edema and side effect after administration of the PPC injectable composition solubilized with GCA of the present invention. Specifically, after topical anesthesia with 9.6% lidocaine cream for 30 minutes or more, 10 ml of the compositions of the present invention (PPC 5.0% injectable preparation solubilized with GCA 2.8% (the molar ratio of GCA to PPC is 0.97) or PPC 5.0% injectable preparation solubilized with GCA 4.0% (the molar ratio of GCA to PPC is 1.39)) were administered to the subjects who had received a 10 ml of composition in which Lipobean i.v. (5 ml) was diluted with injectable saline solution (5 ml) at a ratio of 1:1 (that is, PPC 2.5%+DCNa 1.2%) with syringes loaded with 13 mm 30G injection needle into abdomen and flank (1.5 cm interval, 10-12 mm depth, 0.5 cc per point, and total of from 50 ml to 100 ml per administration) or into the submental fat (1.0 cm interval, 6-8 mm depth, 0.2 cc per point, and total of 10 ml per administration), with the same administration methods. After the administration, subjects were given questionnaire, 10 cm ruler and blue oil pens for VAS (Visual Analogue Scale) pain evaluation, and a pain, edema, swelling, hematoma, bruise, erythema, anesthesia, induration, paresthesia, nodule and pruritus were evaluated upon administration, 1, 3, 7 and 10 days after administration. The pain was evaluated by using a 10 cm ruler and a planetary pen with a 10-cm long line to record no pain at the left end and the most severe pain imaginable at the right end. In the case of edema and swelling, after pressing the site of administration and the other site using the 10 cm ruler while looking at the mirror, and the subject recorded as 0. None, 1. Mild (2 mm or less), 2. Moderate (2-4 mm), 3. Severe (4-6 mm) and 4. Extremely severe (6-8 mm). In the case of hematoma, bruise and erythema, the subject recorded the degree as 0. None, 1. Mild, 2. Moderate, 3. Severe and 4. Extremely severe by comparing with the attached example images. In the case of anesthesia, induration, paresthesia, nodule and pruritus which are subjective symptoms, the subject recorded the degree as 0. None, 1. Mild, 2. Moderate, 3. Severe and 4. Extremely severe, after pressing the entire site of administration.

Figure 15B:
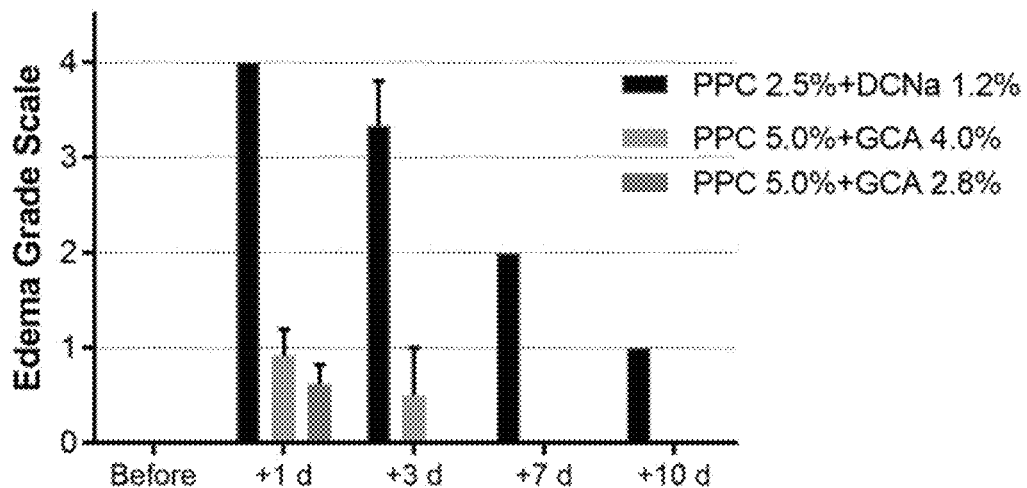
Figure 15C:
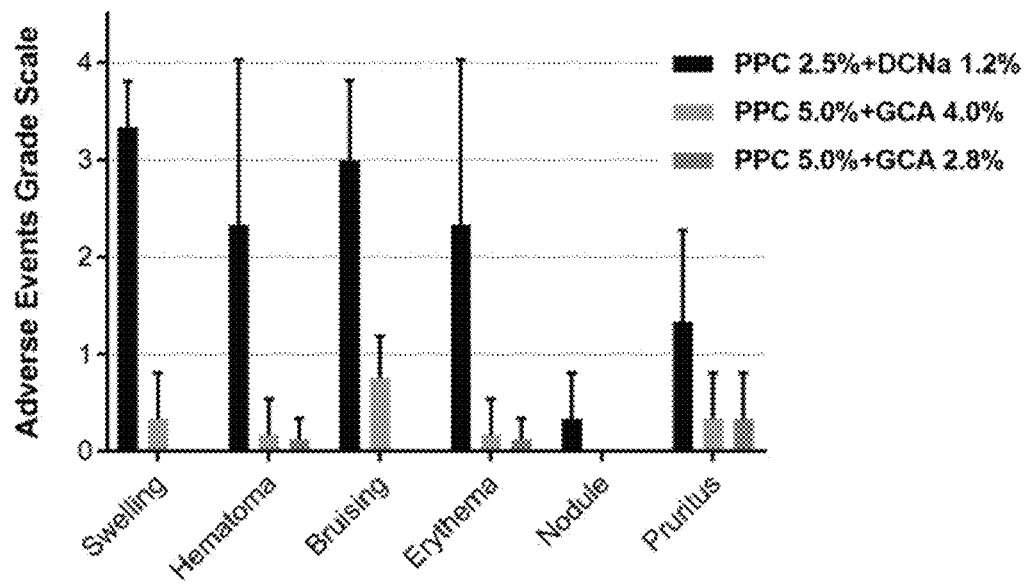
Figure 16:
FIG. 16 shows the images comparing the skin lesion (erythema, bruising and hematoma) after administration of the solution in which Lipobean i.v. (PPC 50.0 mg+DCNa 24.0 mg in 1 ml) was diluted with injectable 0.9% saline solution at a ratio of 1:1 (that is, PPC 25.0 mg+DCNa 12.0 mg in 1 ml of the solution) or PPC complex composition solubilized with GCA (PPG 50 mg+GCA 40 mg in 1 ml). After the topical anesthesia with 9.6% lidocaine ointment at the site of administration (under the chin) for 30 minutes, 50 ml of each test material was administered into subcutaneous fat layer of flank (total of 100 points, 0.5 cc per point, 1.5 cm interval, a 10-12 mm depth, and using a 30 G 13 mm injection needle). The images were taken 2 days after the administration. At the administration site of the PPC injectable preparation solubilized with DCA, skin lesions such as erythema, bruising, and hematoma were observed along the drug-dispersing region. However, the PPC complex composite injectable preparation solubilized with GCA of the present invention showed only hematoma and bruise caused by invasion of needle.
Figure 16:
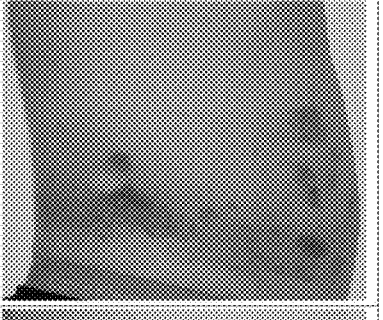
Figure 16:
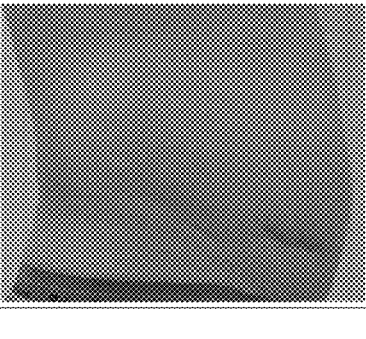
Figure 16:
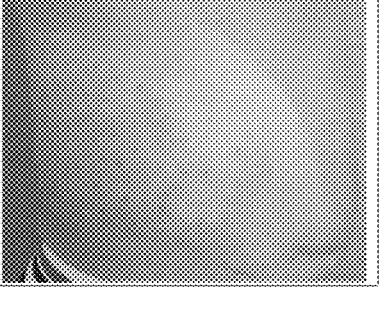

As shown in FIG. 15 (FIG. 15C) and FIG. 16, the subjects who had received administration of the PPC injectable composition solubilized with DCNa particularly complained of pain and edema at the time of administration and 10 days after administration, and the subject reported skin lesions such as erythema, hematoma and bruise, and localized adverse events such as induration, nodule, pruritus and burning sensation. However, surprisingly, the subjects receiving the administration of PPC injectable preparations solubilized with GCA of the present invention showed mild levels, that was practically absent, of pain (FIG. 15A) and edema (FIG. 15B), especially. In particular, as shown in FIG. 15A, it is very unusual that the PPC+GCA complex composition of the present invention has almost no pain even at the time of injection. Considering the facts comprehensively that the PPC injectable preparation solubilized with DCNa (a sodium salt of DCA) which is a conventional preparation and was used as a comparative example has the similar particle characteristics (micelles, particle size, etc.) to the compositions of the present invention, and those injectable preparations are administered at a pH similar to that of the human body, such effect of the composition of the present invention is unique effect that is difficult to predict from previously known techniques.

In addition, as shown in FIG. 16, the hematoma and erythema caused by the test materials were reduced after administration of the composition of the present invention to no or mild level except for the bruise caused by the injection needle itself or hematoma caused by vascular damage at the time of injection. Specifically, as shown in FIG. 15C, there was no side effect of nerve injury such as anesthesia, extensive swelling, hematoma caused by drug, bruising, erythema, induration, paresthesia, nodule, pruritus, burning sensation (warmth), dysphagia, and the like. Considering the test result of in vivo, in vitro and single dose toxicity, the adipocyte apoptosis and fat degradation effects of the PPC compositions solubilized with GCA can be clinically demonstrated in human with safety and high efficacy.

INDUSTRIAL APPLICABILITY

As described above, the present invention relates to a composition useful to reduce fat non-surgically without a pain, edema, and side effect in a subject having localized fat deposition using pharmaceutically active phosphatidylcholine and a method for preparing the same. More specifically, a composition and preparation for reducing localized fat with a reduced pain and side effect (especially, necrosis of muscle cells, fibroblasts and vascular endothelial cells other than adipocytes; edema; anesthesia of administration sites; extensive swelling; erythema; induration; paresthesia; nodule; pruritus; burning sensation; nerve injury; or dysphagia), the composition comprising: (i) phosphatidylcholine; and (ii) at least one selected from the group consisting of glycocholic acid (GCA), taurocholic acid (TCA) and salt thereof, wherein a molar ratio of (ii) to (i) in the composition is in a range of 0.7 to 3.0, a kit comprising the same, a method for preparing the same, and a method for non-surgically removing localized fat deposition with a reduced pain and side effect using the composition or preparation.

Single compositions of deoxycholic acid (DCA) or complex compositions of phosphatidyl choline (PPC) and deoxycholic acid (DCA), the conventional injectable preparations for reducing localized fat, is reported to induce side effects caused by necrosis of adipocyte and cytolysis of fibroblast, endothelial cell and skeletal muscle cell such as anesthesia, extensive swelling, hematoma caused by drug, bruising, erythema, induration, paresthesia, nodule, pruritus, burning sensation (warmth), dysphagia, and the like. However, since the injectable preparation for reducing localized fat of the present invention reduces localized fat by selectively inducing lipolysis and apoptosis of only adipocyte, the composition of the present invention not only shows significant effect on reducing adipocytes, but also demonstrates significantly reduced pain and side effects which are accompanied by conventional cytolytic injectable compositions. Thereby, the medication compliance of subjects is remarkably improved, and ultimately, the quality of life of the subjects who want to reduce localized fat is improved. Therefore, industrial applicability is high.

The invention claimed is:

1. A method for removing localized fat deposition with a reduced pain and side effect in a subject, the method comprising administering an effective amount of a composition or preparation consisting essentially of phosphatidylcholine; and at least one solubilizing agent of phosphatidylcholine selected from the group consisting of glycocholic acid, taurocholic acid and salt thereof to the subject having localized fat deposition, wherein a molar ratio of the solubilizing agent of phosphatidylcholine to the phosphatidylcholine in the composition or preparation is in a range of 0.7 to 3.0, and wherein the phosphatidylcholine is contained in the composition or preparation in a concentration of 0.3125 to 10% (w/v).

2. The method of claim 1, wherein the localized fat deposition is non-surgically removed.

3. The method of claim 1, wherein the side effect is at least one selected from the group consisting of edema; necrosis of muscle cells, fibroblasts and vascular endothelial cells other than adipocytes; anesthesia of administration sites; extensive swelling; erythema; induration; paresthesia; nodule; pruritus; burning sensation; nerve injury; and dysphagia.

4. The method of claim 1, wherein the step of administration comprises a subcutaneous injection.

5. A method for non-surgically removing localized fat deposition with a reduced pain and side effect in a subject having localized fat deposition, the method comprising administering a composition or preparation consisting essentially of (i) phosphatidylcholine; and (ii) at least one selected from the group consisting of glycocholic acid, taurocholic acid and salt thereof to the subject having localized fat deposition, wherein a molar ratio of (ii) to (i) in the composition or preparation is in a range of 0.7 to 3.0, and wherein the phosphatidylcholine is contained in the composition or preparation in a concentration of 0.3125 to 10% (w/v).

6. The method of claim 5, wherein the composition or preparation is in a form of an injectable composition or preparation.

7. The method of claim 5, wherein the side effect is at least one selected from the group consisting of edema; necrosis of muscle cells, fibroblasts and vascular endothelial cells other than adipocytes; anesthesia of administration sites; extensive swelling; erythema; induration; paresthesia; nodule; pruritus; burning sensation; nerve injury; and dysphagia.

8. The method of claim 5, wherein the step of administration comprises a subcutaneous injection.

* * * * *